(12) United States Patent
Babish et al.

(10) Patent No.: US 7,815,944 B2
(45) Date of Patent: *Oct. 19, 2010

(54) ANTI-INFLAMMATORY PHARMACEUTICAL COMPOSITIONS FOR REDUCING INFLAMMATION AND THE TREATMENT OF PREVENTION OF GASTRIC TOXICITY

(75) Inventors: John G. Babish, Brooktondale, NY (US); Matthew L. Tripp, Gig Harbor, WA (US); Jeffrey S. Bland, Fox Island, WA (US); Terrence Howell, Lansing, NY (US); Gary K. Darland, Gig Harbor, WA (US); Robert H. Lerman, Gig Harbor, WA (US); Daniel O. Lukaczer, Gig Harbor, WA (US)

(73) Assignee: Metaproteomics, LLC, San Clemente, CA (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/355,306

(22) Filed: Feb. 15, 2006

(65) Prior Publication Data

US 2006/0141082 A1    Jun. 29, 2006

Related U.S. Application Data

(60) Division of application No. 10/774,048, filed on Feb. 4, 2004, now abandoned, which is a continuation-in-part of application No. 10/689,856, filed on Oct. 20, 2003, now Pat. No. 7,270,835, which is a continuation-in-part of application No. 10/464,410, filed on Jun. 18, 2003, which is a continuation-in-part of application No. 10/400,293, filed on Mar. 26, 2003, now abandoned, and a continuation-in-part of application No. 10/401,283, filed on Mar. 26, 2003, now abandoned, application No. 11/355,306, which is a continuation-in-part of application No. 10/464,834, filed on Jun. 18, 2003, which is a continuation-in-part of application No. 10/400,293, filed on Mar. 26, 2003, now abandoned, and a continuation-in-part of application No. 10/401,283, filed on Mar. 26, 2003, now abandoned, application No. 11/355,306, which is a continuation-in-part of application No. 09/885,721, filed on Jun. 20, 2001, now Pat. No. 7,205,151.

(60) Provisional application No. 60/450,237, filed on Feb. 25, 2003, provisional application No. 60/420,383, filed on Oct. 21, 2002.

(51) Int. Cl.
*A01N 65/00* (2009.01)
(52) U.S. Cl. .................................................... 424/725
(58) Field of Classification Search ................ None
See application file for complete search history.

(56) References Cited

U.S. PATENT DOCUMENTS

| | | | |
|---|---|---|---|
| 3,451,821 A | 6/1969 | Todd et al. |
| 3,552,975 A | 1/1971 | Worden |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzner et al. |
| 4,644,084 A | 2/1987 | Cowles et al. |
| 4,692,280 A | 9/1987 | Spinelli |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |

(Continued)

FOREIGN PATENT DOCUMENTS

CN    1203268    12/1998

(Continued)

OTHER PUBLICATIONS

Bermejo, et al. Rev. Esp. Enferm. Dig. 95: 621-624 and 625-628 (2003).

(Continued)

*Primary Examiner*—Michael V Meller
(74) *Attorney, Agent, or Firm*—McDermott Will & Emery LLP

(57) ABSTRACT

The invention provides hops (*Humulis lupulus*) extracts or derivatives thereof for use in treating a patient prophylactically and/or therapeutically for ulcerogenic-type disorders of the stomach and/or intestines. The ulcerogenic disorders can be of the type chemically induced, environmentally-induced, infection-induced, and/or stress-induced. The invention also provides a pharmaceutical composition comprising an active amount of hops extracts or derivatives thereof, in combination with an analgesic compound and/or an anti-inflammatory compound. The invention further provides for use of hops extracts or derivatives thereof, significantly reducing and/or therapeutically treating ulcerogenic-type disorders of the stomach and/or intestines.

12 Claims, 20 Drawing Sheets

U.S. PATENT DOCUMENTS

| | | | |
|---|---|---|---|
| 5,041,300 A | 8/1991 | Todd et al. | |
| 5,073,396 A | 12/1991 | Todd, Jr. | |
| 5,082,975 A | 1/1992 | Todd, Jr. et al. | |
| 5,155,276 A | 10/1992 | Paul | |
| 5,166,449 A | 11/1992 | Todd, Jr. et al. | |
| 5,264,236 A | 11/1993 | Ogasahara et al. | |
| 5,286,506 A | 2/1994 | Millis et al. | |
| 5,296,637 A | 3/1994 | Stegink et al. | |
| 5,370,863 A | 12/1994 | Barney et al. | |
| 5,387,425 A | 2/1995 | Hsu et al. | |
| 5,604,263 A | 2/1997 | Tobe et al. | |
| 5,641,517 A | 6/1997 | Eskeland et al. | |
| 5,827,895 A | 10/1998 | Nutter et al. | |
| 5,866,162 A | 2/1999 | Grattan | |
| 5,919,813 A | 7/1999 | De Juan | |
| 5,968,539 A | 10/1999 | Beerse et al. | |
| 6,020,019 A | 2/2000 | Ting et al. | |
| 6,129,907 A | 10/2000 | Sreenivasan et al. | |
| 6,200,594 B1 | 3/2001 | Ernest et al. | |
| 6,291,483 B1 | 9/2001 | Upadhyay et al. | |
| 6,383,527 B1 | 5/2002 | Artman et al. | |
| 6,391,346 B1 | 5/2002 | Newmark et al. | |
| 6,440,465 B1 | 8/2002 | Meisner | |
| 6,447,762 B1 | 9/2002 | Galcerá | |
| 6,482,456 B1 | 11/2002 | Yokoo et al. | |
| 6,583,322 B1 | 6/2003 | Shahlai et al. | |
| 6,689,388 B2 | 2/2004 | Kuhrts | |
| 6,790,459 B1 | 9/2004 | Cheng et al. | |
| 6,801,860 B1 | 10/2004 | Dessen et al. | |
| 7,144,590 B2 * | 12/2006 | Kuhrts | 424/725 |
| 7,195,785 B2 | 3/2007 | Babish et al. | |
| 7,205,151 B2 | 4/2007 | Babish et al. | |
| 7,270,835 B2 | 9/2007 | Tripp et al. | |
| 7,279,185 B2 | 10/2007 | Babish et al. | |
| 7,332,185 B2 | 2/2008 | Babish et al. | |
| 7,431,948 B2 | 10/2008 | Tripp et al. | |
| 2002/0028852 A1 | 3/2002 | Ghai et al. | |
| 2002/0076452 A1 | 6/2002 | Babish et al. | |
| 2002/0077299 A1 | 6/2002 | Babish et al. | |
| 2002/0086062 A1 | 7/2002 | Kuhrts | |
| 2002/0086070 A1 | 7/2002 | Kuhrts | |
| 2002/0156087 A1 | 10/2002 | Nuss et al. | |
| 2003/0003212 A1 | 1/2003 | Chien et al. | |
| 2003/0077313 A1 | 4/2003 | Schwartz et al. | |
| 2003/0096027 A1 | 5/2003 | Babish et al. | |
| 2003/0113393 A1 | 6/2003 | Babish et al. | |
| 2003/0133958 A1 | 7/2003 | Kuno et al. | |
| 2003/0180402 A1 | 9/2003 | Jia et al. | |
| 2003/0228369 A1 | 12/2003 | Kuhrts | |
| 2004/0072900 A1 | 4/2004 | Artman et al. | |
| 2004/0086580 A1 | 5/2004 | Tripp et al. | |
| 2004/0115290 A1 | 6/2004 | Tripp et al. | |
| 2004/0137096 A1 | 7/2004 | Kuhrts | |
| 2004/0151792 A1 | 8/2004 | Tripp et al. | |
| 2004/0219240 A1 | 11/2004 | Babish et al. | |
| 2005/0042317 A1 | 2/2005 | Babish et al. | |
| 2005/0129791 A1 | 6/2005 | Babish et al. | |
| 2005/0192356 A1 | 9/2005 | Babish et al. | |
| 2006/0127511 A1 | 6/2006 | Tripp et al. | |
| 2006/0127512 A1 | 6/2006 | Tripp et al. | |
| 2006/0127513 A1 | 6/2006 | Tripp et al. | |
| 2006/0127514 A1 | 6/2006 | Tripp et al. | |
| 2006/0127515 A1 | 6/2006 | Tripp et al. | |
| 2006/0127516 A1 | 6/2006 | Tripp et al. | |
| 2006/0127517 A1 | 6/2006 | Tripp et al. | |
| 2006/0193933 A1 | 8/2006 | Tripp et al. | |
| 2007/0003646 A1 | 1/2007 | Kuhrts | |
| 2007/0020352 A1 | 1/2007 | Tripp et al. | |
| 2007/0160692 A1 | 7/2007 | Tripp et al. | |
| 2007/0166418 A1 | 7/2007 | Tripp et al. | |
| 2007/0172532 A1 | 7/2007 | Babish et al. | |
| 2007/0184133 A1 | 8/2007 | Tripp et al. | |
| 2009/0118373 A1 | 5/2009 | Tripp et al. | |

FOREIGN PATENT DOCUMENTS

| | | |
|---|---|---|
| DE | 2212148 | 9/1972 |
| DE | 3931147 | 3/1991 |
| DE | 19841615 | 3/2000 |
| EP | 0606599 A1 | 7/1994 |
| EP | 0681029 A2 | 11/1995 |
| GB | 2330076 | 4/1999 |
| JP | 363211219 | 9/1988 |
| JP | 04202138 | 7/1992 |
| JP | 6312924 | 11/1994 |
| JP | 07194351 | 8/1995 |
| JP | 8073369 | 3/1996 |
| JP | 9067245 | 3/1997 |
| JP | 410025247 | 1/1998 |
| JP | 10152428 | 6/1998 |
| JP | 2002-12550 | 1/2002 |
| RU | 2045955 | 10/1995 |
| SU | 1247011 | 7/1986 |
| WO | WO99/4462 | 9/1999 |
| WO | WO 9961038 | 12/1999 |
| WO | WO 00/68356 | 11/2000 |
| WO | WO00/74696 | 12/2000 |
| WO | WO02/02582 | 1/2002 |
| WO | WO03/082249 | 10/2003 |
| ZA | 200000857 | 8/2001 |

OTHER PUBLICATIONS

Brown, et al. J. Chem. Soc. 545 (1959).
Byrne, et al. J. Chem. Soc. (C):2810 (1971).
Carroccio, et al. Clin. Chem. 49:861-867 (2003).
Carson, J. Am. Chem. Soc. 73:1850-1851 (1951).
Charlier, et al. Eur. J. Med. Chem. 38:645-659 (2003).
Chou, et al. Adv Enzyme Regul 22:27-55 (1984).
Chou, et al. Eur. J. Biochem. 115:207-216 (1981).
Chou, et al. J. Biol. Chem. 252:6438-6442 (1977).
Chou, et al. J. Theor. Biol. 35:285-297 (1972).
Chou, J. Theor. Biol. 59:253-276 (1976).
Chou, et al. Trends Pharmacol. Sci. 4:450-454 (1983).
Costa,et al. Digest. Liver Dis. 35:642-647 (2003).
Ding, et al. Biochem. Biophy. Res. Comm. 261:218-223 (1999).
Goldstein, et al. Am. J. Gastroenterol. 96:1019-1027 (2001).
Halter, et al. Gut 49:443-453 (2001).
Hammberg, et al. J. Bio. Chem. 246:6713-6721 (1971).
Kanematsu, et al. J Bone Miner Res 12(11):1789-1796 (1997).
Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Thomas M. Newmark and Paul Schulick, Beyond Aspirin Nature's Answer to Arthritis, Cancer & Alzheimer's Disease, Hohm Press (2000) (this is a general reference to a book which has not been provided).
Pairet, et al. Inflamm. Res 47, Supplement 2S93-S101 (1998).
Panglisch, Monafsschrift fuer Brauwissen Schaft, 1990, 43(1), 4-16.
Ringbom, et al. J. Nat Prod 61:1212-1215 (1998).
Pippa,et al. Scand. J. Gastroenterol. Suppl. 167:32-35 (1989).
Poullis ,et al. J. Gastroenterol. Hepatol. 18:756-762 (2003).
Røseth, Digest. Liver Dis. 35:607-609 (2003).
Shah, et al. Gut 48:339-346 (2001).
Schjerven, et al. Br. J. Dermatol. 149:484-491 (2003).
Shureiqi, et al. Cancer Res. 61:6307-6312 (2001).
Sivri, Fundam. Clinic. Pharmacol. 18:23-31 (2004).
Subbaramaiah, et al. Cancer Res. 60:2399-2404 (2000).
Suh, et al. Cancer Res 58:717-723 (1988).
Tagashira, et al., Biosci, Biotech. Biochem. 59(4):740-742 (1996).
Tibble, et al. Drugs Today 37:85-96 (2001).
Tibble, et al. Gut 45:362-366 (1999).
Tobe, et al. Biosci. Biotech. Biochem 61(1):158-159 (1997).
Yui, et al. Biol. Pharm. Bull. 26:753-760 (2003).
Wang, et al. Free Radical Biology & Medicine 27:612-616 (1999).

Warner, et al. Proc Natl Acad Sci USA 96:7563-7568 (1999).
Yamamoto, FEBS Letters 465:103-106 (2000).
"Information on a book titled Beyond Aspirin", by Thomas Newmark, et al., Release 7/00; pp. 147-151, 248.
Germany, "The Absolutely German Drink," contents of beer, 2004, 5 pages.
Parts Per Million, 1 page.
Q & A, 3 pages, 2004.
"Information on ArthroTrim™ product", downloaded from Internet Aug. 30, 2002.
"Information on Zyflamend and Zyflamend PM", downloaded from Internet Aug. 30, 2002.
Albal, M.V., et al., "Clinical evaluation of berberine in mycotic infections." Indian J. Ophthalmol 34:91-2 (1986).
Anto, et al. Pharm. Pharmacol. Comm. 4:103-106 (1998).
Bermejo, et al. Rev. Esp. Enferm. Dig. 95(9): 625-628 (2003).
Byrne. et al. J. Chem. Soc. (c):2810-2813 (1971).
Carroccio, et al. Clin. Chem. 49(6):861-867 (2003).
Carson, J., Am. Chem. Soc. 73:1850-1851 (1951).
Chandra, et al. Indian J. Medical Research 60(1):138-142 (1972).
Chou et al. Eur. J. Biochem. 115:207-216 (1981).
Chou, et al. Adv enzyme regul 22:27-55 (1983).
Chon, et al. J. Biol. Chem. 252(18):6438-6442 (1977).
Cohen, Protein Kinases—the major drug targets of the twenty-first century? Nature Reviews, 1: 309-315 (2002).
Davies, WL. Abstract—Fertiliser, Feeding Stuffs and Farm Supplies J. 11:694 (1926).
De Keukeleire, et al., Quimica Nova, vol. 23, No. 1, pp. 108-112 (2000).
Exercise as Treatment for Arthritis, Rheumatic and Immunologic Diseases, Cleveland Clinic, www.clevelandclinic.org. Mar. 14, 2000.
Friedman, et al. J Cutan Med. Surg. 6(5):449-459 (2002).
Gerhauser, Beer Constituents as Potential Cancel Chemopreventive Agents, EP Journal of Cancer 41: 1941-1954: (2005).
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96(4):1019-1027 (2001).
Hamberg, et al. J. Bio. Chem. 246(22):6713-6721 (1971).
Huang, et al. Cancer Res. 51:813-819 (1991).
International Search Report for PCT/US06/30920. Aug. 3, 2007. 3 pages.
International Search Report for PCT/US02/19617.
International Search Report for PCT/US04/16043.
International Search Report for PCT/US06/47196.
Jach, Przegl Dermatol 65(4):379-381 (1978).
Kaltner, D., Technische Universitat Munchen, (Nov. 30, 2000), pp. 1-193. plus Tabs. AH1-AH31.
Kaltner, Investigation of formation of Hops Aroma and technological Measures for Products of Hops-Aromatic Beers, Technical University of Munich, 7 pp.
Kanematsu, et al. J Bone Miner Res 12:1789-1796 (1997).
Lopes, Curr. Med Res Opin. 8(3):145-149 (1982).
Newmark, et al., "Beyond Aspirin nature's answer to arthritis, cancer & Alzheimer's disease," hohm press (2000) release 7; pp. 147-151, 248.
Pairet, et al. Inflamm. Res 47(2), s93-s101 (1998).
Pippa, et al. Scand. J. Gastroenterol. 32-35 (1989).
Plewig, et al, J Invest. Dermatol. 65(6):532-536 (1975).
Poullis, et al. J. Gastroenterol. Hepatol. 18:756-762 (2003).
Provital Group, Rosemary-cco Botany, 2007, 9 pages.
Q&A, 3 pages (2004).
Rahman, M.M., et al.. "Conjugated linoleic acid inhibits osteoclast differentiation of RA W264.7 cells by modulating RANKL signaling" J. Lipid Res., 47(8): 1739-1748, (2006).
Shimamura, et al. Biochem. Biophys. Res. Comm 289:220-224 (2001).
Smith, et al., Natural Foam Stabilizing and Bittering Compounds Derived From Hops, Journal of the American Society of Brewing Chemists, vol. 56, No, 2, 1998, pp. 52-57.
Stevens, Xanthohumol and related Prenylflavonoids from Hops and Beer: To Your Good Health, Science Direct, 2pp (2004).
Suh, et al. Cancer Res. 58:717-723 (1988).
Supplementary Partial European Search Report for related European Patent Application No. 05723895.8, 5 pages (2007).
Tagashira, et al., Biosci. Biotech. Biochem. 59(4):740-742 (1996).
The national. 3 pages (1999).
Tibble, et al. Drugs Today 37(2):85-96 (2001).
US News and world report, 10 pages (2008).
Van Montfrans et al. Inflammatory Signal Transduction in Crohn's Disease and Novel Therapeutic Approaches. Science Direct, Jun. 2, 2002, 20 pages. Biochemical Pharmacology, vol. 64, issues 5-6.
Vanhoenacker, et al., Journal of Chromatography, vol. 1035, No. 1, (Apr. 30, 2004), pp. 53-61.
Wang, et al. Free Radical Biology & Medicine 27(5/6):612-616 (1999).
Ward. et al., Therapeutic Potential of Phosphoinositide 3-Kinase Inhibitors, Chemistry & Biology, vol. 10, 207-210, Mar. 2003.
Yamamoto, et al, Abstract—Prostaglandiols & Other Lipid Mediators 59:1-235 (1999).
Yui, et al. Biol. Pharm. Bull. 26(6):753-760 (2003).

* cited by examiner

ANTI-INFLAMMATORY PHARMACEUTICAL COMPOSITIONS FOR REDUCING INFLAMMATION AND THE TREATMENT OF PREVENTION OF GASTRIC TOXICITY

This patent application is a divisional of U.S. application Ser. No. 10/774,048, filed on Feb. 4, 2004, now abandoned, which is a continuation-in-part of U.S. application Ser. No. 10/689,856, filed Oct. 20, 2003, now U.S. Pat. No. 7,270,835, which is a continuation-in-part of U.S. application Ser. No. 10/464,410, filed Jun. 18, 2003, which is a continuation-in-part of U.S. application Ser. No. 10/400,293, filed Mar. 26, 2003, now abandoned, and a continuation-in-part of U.S. application Ser. No. 10/401,283, filed Mar. 26, 2003, now abandoned, both of which claim the benefit under 35 U.S.C. §119(e) to provisional application No. 60/450,237, filed on Feb. 25, 2003, and provisional application No. 60/420,383, filed on Oct. 21, 2002; and is a continuation-in-part of U.S. patent application Ser. No. 10/464,834, filed Jun. 18, 2003, which is a continuation-in-part of U.S. application Ser. No. 10/400,293, filed Mar. 26, 2003, now abandoned, and a continuation-in-part of U.S. application Ser. No. 10/401,283, filed Mar. 26, 2003, now abandoned, both of which claim the benefit under 35 U.S.C. §119(e) to provisional application No. 60/450,237, filed on Feb. 25, 2003, and provisional application No. 60/420,383, filed on Oct. 21, 2002. The U.S. patent application Ser. No. 10/464,834 is also a continuation-in-part of U.S. application Ser. No. 09/885,721, filed Jun. 20, 2001, now U.S. Pat. No. 7,205,151. The contents of each of these earlier applications are hereby incorporated by reference as if recited herein in their entirety.

BACKGROUND OF THE INVENTION

This invention relates to pharmaceutical compositions containing hops (*Humulus lupulus*) extracts or derivatives thereof. The present invention also relates to methods of using compositions obtained or derived from hops to treat, prevent or attenuate gastropathy, and particularly but not exclusively that caused by non-steroidal anti-inflammatory drugs.

Prostaglandins (PGs) are ubiquitous hormones that function as both paracrine and autocrine mediators to affect a myriad of physiological changes in the immediate cellular environment. The varied physiological effects of PGs include inflammatory reactions such as rheumatoid arthritis and osteoarthritis, blood pressure control, platelet aggregation, induction of labor and aggravation of pain and fever. The discovery 30 years ago that aspirin and other non-steroidal analgesics inhibited PG production identified PG synthesis as a target for drug development. There are at least 16 different PGs in nine different chemical classes, designated PGA to PGI. PGs are part of a larger family of 20-carbon-containing compounds called eicosanoids; they include prostacyclins, thromboxanes, and leukotrienes. The array of PGs produced varies depending on the downstream enzymatic machinery present in a particular cell type. For example, endothelial cells produce primarily $PGI_2$, whereas platelets mainly produce $TXA_2$.

Arachidonic acid serves as the primary substrate for the biosynthesis of all PGs. Cyclooxygenase (prostaglandin endoperoxide synthase, EC 1.14.991, COX) catalyzes the rate-limiting step in the metabolism of arachidonic acid to prostaglandin $H_2$ ($PGH_2$), which is further metabolized to various prostaglandins, prostacyclin and thromboxane A2 (see FIG. 1). In the early 1990s, it was established that COX exists in two isoforms, commonly referred to as COX-1 and COX-2. It was subsequently determined that the COX-1 and COX-2 proteins are derived from distinct genes that diverged well before birds and mammals. PGs generated via the COX-1 and COX-2 pathways are identical molecules and therefore have identical biological effects. COX-1 and COX-2, however, may generate a unique pattern and variable amounts of eicosanoids; therefore, relative differences in the activation of these isozymes may result in quite dissimilar biological responses. Differences in the tissue distribution and regulation of COX-1 and COX-2 are now considered crucial for the beneficial as well as adverse effects of COX inhibitors.

The generally held concept (COX dogma) is that COX-1 is expressed constitutively in most tissues whereas COX-2 is the inducible enzyme triggered by pro-inflammatory stimuli including mitogens, cytokines and bacterial lipopolysaccharide (LPS) in cells in vitro and in inflamed sites in vivo. Based primarily on such differences in expression, COX-1 has been characterized as a housekeeping enzyme and is thought to be involved in maintaining physiological functions such as cytoprotection of the gastric mucosa, regulation of renal blood flow, and control of platelet aggregation. COX-2 is considered to mainly mediate inflammation, although constitutive expression is found in brain, kidney and the gastrointestinal tract.

Prostaglandins (PG) are believed to play an important role in maintenance of human gastric mucosal homeostasis. Current dogma is that COX-1 is responsible for PG synthesis in normal gastric mucosa in order to maintain mucosal homeostasis and that COX-2 is expressed by normal gastric mucosa at low levels, with induction of expression during ulcer healing, following endotoxin exposure or cytokine stimulation. It now appears that both COX-1 and COX-2 have important physiological roles in the normal gastric mucosa.

Compounds that inhibit the production of PGs by COX have become important drugs in the control of pain and inflammation. Collectively these agents are known as non-steroidal anti-inflammatory drugs (NSAIDs) with their main indications being osteoarthritis and rheumatoid arthritis. However, the use of NSAIDs, and in particular aspirin, has been extended to prophylaxis of cardiovascular disease. Over the last decade, considerable effort has been devoted to developing new molecules that are direct inhibitors of the enzymatic activity of COX-2, with the inference that these compounds would be less irritating to the stomach with chronic use.

The major problem associated with ascertaining COX-2 selectivity (i.e. low gastric irritancy) is that differences in assay methodology can have profound effects on the results obtained. Depicted in Table 1 are the categories of the numerous in vitro assays that have been developed for testing and comparing the relative inhibitory activities of NSAID and natural compounds against COX-1 and COX-2. These test systems can be classified into three groups: (1) systems using animal enzymes, animal cells or cell lines, (2) assays using human cell lines, or human platelets and monocytes, and (3) currently evolving models using human cells that are representative of the target cells for the anti-inflammatory and adverse effects of NSAID and dietary supplements. Generally, models using human cell lines or human platelets and monocytes are the current standard and validated target cell models have not been forthcoming. A human gastric cell line capable of assessing potential for gastric irritancy is a critical need.

The enzymes used can be of animal or human origin, they can be native or recombinant, and they can be used either as purified enzymes, in microsomal preparations, or in whole-cell assays. Other system variables include the source of arachidonic acid. PG synthesis can be measured from endogenously released arachidonic acid or exogenously added arachidonic acid. In the later case, different concentrations are used in different laboratories.

An ideal assay for COX-2 selectivity would have the following characteristics: (1) whole cells should be used that contain native human enzymes under normal physiological control regarding expression; (2) the cells should also be target cells for the anti-inflammatory and adverse effects of the compounds; (3) COX-2 should be induced, thereby simulating an inflammatory process, rather than being constitutively expressed; and (4) PG synthesis should be measured from arachidonic acid released from endogenous stores rather than from exogenously added arachidonic acid.

TABLE 1

Classification of test systems for in vitro assays assessing COX-2 selectivity of anti-inflammatory compounds†
I. TEST SYSTEMS

| A. ANIMAL | B. HUMAN | C. TARGET |
| --- | --- | --- |
| Enzymes | Enzymes | Human Gastric Mucosa Cells |
| Cells | Cells | Human Chondrocytes |
| Cell lines | Cell lines | Human Synoviocytes |

D. OTHER SYSTEM VARIABLES

1. Source of arachidonic acid - endogenous or exogenous;
2. Various expression systems for gene replication of COX-1 and COX-2;
3. The presence or absence of a COX-2 inducing agent;
4. COX-2 inducing agents are administered at different concentrations and for different periods of time;
5. Duration of incubation with the drug or with arachidonic acid;
6. Variation in the protein concentration in the medium.

†Adapted from Pairet, M. and van Ryn, J. (1998) Experimental models used to investigate the differential inhibition of cyclooxygenase-1 and cyclooxygenase-2 by non-steroidal anti-inflammatory drugs. Inflamm. Res 47, Supplement 2S93-S101 and incorporated herein by reference.

No laboratory has yet developed an ideal assay for COX-2 selectivity. The whole cell system most commonly used for prescription (Rx) and over the counter (OTC) products is the human whole blood assay developed by the William Harvey Institute [Warner, T. D. et al. (1999) *Nonsteroid drug selectivities for cyclo-oxygenase-1 rather than cyclo-oxygenase-2 are associated with human gastrointestinal toxicity: a full in vitro analysis. Proc Natl Acad Sci USA* 96, 7563-7568]. To date, this assay format has developed more data supporting clinical relevance than any other. However, new research in the role of constitutive expression of COX-2 in normal gastric mucosa necessitates revisiting the relevance of the use of platelets to model COX-1 inhibition in the absence of COX-2. The extrapolation of gastrotoxicity from platelet studies is no longer on a sound molecular basis. The validation of a human gastric mucosal cell line for establishing the potential target tissue toxicity of cyclooxygenase inhibitors represents a critical need for the development of safe and effective anti-inflammatory agents.

An ideal formulation for the treatment of inflammation would inhibit the induction and activity of COX-2 without inhibiting the synthesis of $PGE_2$ in gastric mucosal cells. However, conventional non-steroidal anti-inflammatory drugs lack the specificity of inhibiting COX-2 without affecting gastric $PGE_2$ synthesis and are at risk to cause damages on the gastrointestinal system, when used for extended periods. Indeed, even the newly developed, anti-inflammatory drugs such as rofecoxib (Vioxx®, Merck & Co., Inc.) and celecoxib (Celebrex®, Pfizer, Inc.) produce untoward gastric toxicity in the form of induced spontaneous bleeding and delay of gastric ulcer healing.

NSAID Toxicity

NSAIDs are known to cause serious health problems including gastric bleeding and kidney damage. In the United States, there are over 13 million regular users of NSAIDs, 70 million NSAID prescriptions written every year, and 30 billion over the counter NSAIDs tablets sold annually. NSAID-induced disease causes 103,000 hospitalizations per year and an estimated 16,500 deaths annually. Twenty percent of all chronic NSAID users will develop a peptic ulcer. NSAID users have a greater risk—three to four times higher—to upper gastrointestinal bleeding, perforation, or both. Eighty-one percent of patients hospitalized with serious NSAID-induced complications had no previous gastrointestinal symptoms. People over 60 years of age have a significantly higher probability of experiencing complications associated with NSAID use. Moreover, 21% of all adverse drug reaction in the United States are due to NSAID use.

The new selective COX-2 inhibitors such as celecoxib and rofecoxib have been shown to offer a safer alternative to most NSAIDs. However recent studies indicate that selective COX-2 inhibitors do not completely eliminate gastrointestinal toxicity. In fact in cases of inflammation or ulceration of the gastrointestinal tract, prescription COX-2 inhibitors may delay ulcer healing.

Thus, it would be useful to identify a natural formulation of compounds that would specifically inhibit or prevent the synthesis of prostaglandins by COX-2 with little or no effect on synthesis of $PGE_2$ in the gastric mucosa. Such a formulation, which would be useful for preserving the health of joint tissues, for treating arthritis or other inflammatory conditions, has not previously been discovered. The term "specific or selective COX-2 inhibitor" was coined to embrace compounds or mixtures of compounds that selectively inhibit COX-2 over COX-1. However, while the implication is that such a calculated selectivity will result in lower gastric irritancy, unless the test materials are evaluated in gastric cells, the term "selective COX-2 inhibitor" does not carry assurance of safety to gastrointestinal cells. Only testing of compound action in target tissues, inflammatory cells and gastric mucosal cells, will identify those agents with low potential for stomach irritation.

Therefore, it would be useful to identify a composition that would specifically inhibit or prevent the expression of COX-2 enzymatic activity in inflammatory cells, while having little or no effect on $PGE_2$ synthesis in gastric mucosal cells so that these formulations could be used with no gastrointestinal upset. Furthermore, such formulations should allow for healing of pre-existing ulcerative conditions in the stomach. The present invention satisfies this need and provides related advantages as well.

SUMMARY OF THE INVENTION

The invention provides compositions and methods using fractions isolated or derived from hops to ameliorate, inhibit or prevent gastropathy and/or gastroenteropathy associated with a gastrointestinal irritant. The compositions can be combined with other components to enhance desirable effects and inhibit undesirable effects of a second component, for example, non-steroidal anti-inflammatory drug, spices, or other gastrointestinal irritants. The invention also provides methods for reducing gastroenteropathy or gastric toxicity, including ulcerogenic-type disorders.

BRIEF DESCRIPTION OF THE DRAWINGS

FIG. 3A shows the alpha-acid genus (AA) and representative species humulone (R=—$CH_2CH(CH_3)_2$), cohumulone (R=—$CH(CH_3)_2$), and adhumulone (R=—$CH(CH_3)CH_2CH_3$); FIG. 3B shows the isoalpha acid genus (IAA) and representative species isohumulone (R=—$CH_2CH(CH_3)_2$), isocohumulone (R=—$CH(CH_3)_2$), and isoadhumulone (R=—$CH(CH_3)CH_2CH_3$); FIG. 3C shows the reduced isomerized isoalpha acid genus (RIAA) and representative species dihydro-isohumulone (R=—$CH_2CH(CH_3)_2$) dihydro-isocohumulone (R=—$CH(CH_3)_2$), and dihydro-isoadhumulone (R=—$CH(CH_3)CH_2CH_3$); FIG. 3D shows the tetrahydroisoalpha acid genus (THIAA) and representative species tetra-hydro-isohumulone (R=—$CH_2CH(CH_3)_2$), tetra-hydro-isocohumulone ((R=—$CH(CH_3)_2$), and tetra-hydro-isoadhumulone (R=—$CH(CH_3)CH_2CH_3$); FIG. 3E shows and the hexa-hydroisoalpha acid (HHIAA) genus with representative species hexa-hydro-isohumulone (R=—$CH_2CH(CH_3)_2$) hexa-hydro-isocohumulone (R=—$CH(CH_3)_2$), and hexa-hydro-isoadhumulone (R=—$CH(CH_3)CH_2CH_3$).

FIG. 6A shows ibuprofen and RIAA:ibuprofen combinations at 5 (gray bars) and 0.5 (white bars) µg test material/mL. FIG. 6B shows aspirin and RIAA:aspirin combinations at 5 (striped bars) and 0.5 (white bars) µg test material/mL.

FIG. 7A shows ibuprofen and THIAA:ibuprofen combinations at 5 (gray bars) and 0.5 (white bars) µg test material/mL. FIG. 7B shows aspirin and THIAA:aspirin combinations at 5 (striped bars) and 0.5 (white bars) µg test material/mL.

FIG. 8A shows ibuprofen, RIAA and a 1:1 combination of RIAA:ibuprofen. FIG. 8B shows aspirin, RIAA and a 1:1 combination of RIAA:aspirin. Values to the right of 0 indicate decreasing probability of gastrointestinal effects, while values to the left of 0 indicate increasing probability of gastrointestinal effects.

FIG. 9A shows ibuprofen, THIAA, a 1:100 combination of THIAA:ibuprofen and a 1:1 combination of THIAA:ibuprofen. FIG. 9B shows aspirin, THIAA, a 1:100 combination of THIAA:aprin, and a 1:1 combination of THIAA:aspirin. Values to the right of 0 indicate decreasing probability of gastrointestinal effects, while values to the left of 0 indicate increasing probability of gastrointestinal effects.

DETAILED DESCRIPTION OF THE INVENTION

Figure 1:
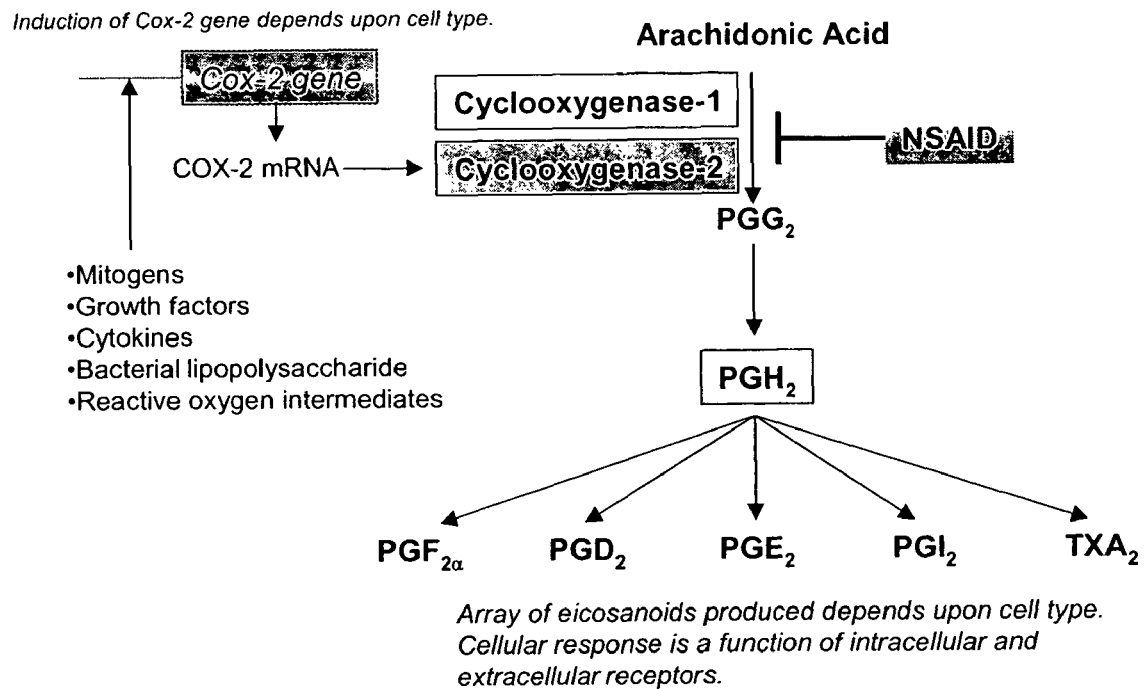
FIG. 1 depicts the induction of cyclooxygenase-2 and the metabolism of arachidonic acid to prostaglandins and other eicosanoids by the cyclooxygenase enzymes. The action of non-steroidal anti-inflammatory agents is through direct inhibition of the cyclooxygenase enzymes.

The present invention provides compositions and methods for modulating the gastrointestinal toxicity of non-steroidal anti-inflammatory drugs (NSAIDs). In particular, the invention provides a supragenus of components isolated or derived from hops (*Humulus lupulus*) that have a modulating effect on the gastrointestinal toxicity of NSAIDs. Specifically, hops derivatives decrease gastric $PGE_2$ inhibition of NSAIDs, producing a more favorable therapeutic index for NSAIDs. The compositions and methods of the invention are advantageous in that the hops derivatives increase the effect of NSAIDs on inflammatory, target cells, thereby further increasing the therapeutic index for NSAIDs. Hops derivatives can also be administered to treat, ameliorate or prevent gastric ulcers induced by the administration of NSAIDs.

The invention provides hops (*Humulus lupulus*) extracts or derivatives thereof for use in treating a patient prophylactically and/or therapeutically for ulcerogenic-type disorders of the stomach and/or intestines. The ulcerogenic disorders can be of the type chemically induced and/or stress-induced. The invention also provides a pharmaceutical composition comprising an active amount of hops extracts or derivatives thereof, in combination with an analgesic compound and/or an anti-inflammatory compound. The invention further provides for use of hops extracts or derivatives thereof, significantly reducing and/or therapeutically treating ulcerogenic-type disorders of the stomach and/or intestines.

As disclosed herein, hops derivatives are effective in decreasing the inhibiting effects of NSAIDs on $PGE_2$ synthesis in gastric mucosal cells, while maintaining or enhancing the $PGE_2$ inhibitory effect in inflammatory cells. In addition, it has been found that chemically induced ulceration, produced by analgesic and/or anti-inflammatory drugs such as ibuprofen, aspirin and indomethacin, or other chemical agents, is significantly reduced when these drugs are administered in conjunction with hop derivatives. Furthermore, it has been found that the toxicity of the organic acids, for example, salicylic acid and other analgesic and/or anti-inflammatory drugs, is reduced to a significant extent when administered in conjunction with hops derivatives. The compositions and methods of the invention are advantageous in that the intrinsic beneficial activity of the analgesic and/or anti-inflammatory drugs is not detrimentally influenced by their use in conjunction with hops derivatives.

As further disclosed herein, it has also been found that hops derivatives possess analgesic activity and that the combined use of hops derivatives with analgesic drugs results in an increased analgesic effect. It has furthermore been found that pharmaceutical preparations comprising hops derivatives are also significantly effective in the prevention or reduction of stress induced gastro-intestinal ulcerations. Additionally, it has also been found that hops derivatives are effective in the healing of ulcers. It will also be understood that, whenever hops derivatives are used for the treatment of ulcers, the aforesaid analgesic activity of hops derivatives may in addition be beneficial in relieving the pain associated with ulcers.

The acute toxicity of hops derivatives is very low. Therefore, relatively high doses of hops derivatives can be used, if desired, without toxic effects due to the hops. Toxic doses are considerably higher than the therapeutic doses contemplated in accordance with the present invention.

The invention provides hops extracts or derivatives thereof for use in treating a patient prophylactically and/or therapeutically for ulcerogenic-type disorders of the stomach and/or intestines. The ulcerogenic disorders can be of the type chemically induced and/or stress-induced. The invention also provides a pharmaceutical composition comprising an active amount of hops extracts or derivatives thereof, in combination with an analgesic compound and/or an anti-inflammatory compound. The invention further provides for use of hops extracts or derivatives thereof, significantly reducing and/or therapeutically treating ulcerogenic-type disorders of the stomach and/or intestines.

As used herein, the term "dietary supplement" refers to compositions consumed to affect structural or functional changes in physiology. The term "therapeutic composition" refers to compounds administered to treat or prevent a disease or to ameliorate a sign or symptom associated with a disease.

As used herein, the term "effective amount" means an amount necessary to achieve a selected result. Such an amount can be readily determined without undue experimentation by a person of ordinary skill in the art.

As used herein, the term "substantial" means being largely but not wholly that which is specified.

As used herein, the term "COX inhibitor" refers to a composition of compounds that is capable of inhibiting the activity or expression of COX-2 enzymes or is capable of inhibiting or reducing the severity, including pain and swelling, of a severe inflammatory response.

As used herein, the terms "derivatives" or a matter "derived" refer to a chemical substance related structurally to another substance and theoretically obtainable from it, that is, a substance that can be made from another substance. Derivatives can include compounds obtained via a chemical reaction. Methods of making derivatives of compounds are well known to those skilled in the art.

As used herein, the term "inflammatory cell" refers to those cellular members of the immune system, for example B and T lymphocytes, neutrophils or macrophages, involved in synthesis of prostaglandins in response to inflammatory signals such as interleukins, tumor necrosis factor, bradykinin, histamine or bacterial-derived components.

As used herein, the term "target cells" refers to that cell population in which the inhibition of $PGE_2$ or other prostaglandin synthesis is desired, such as inflammatory cells or tumor cells. Alternatively, "non-target cells" refers to that cell population in which the inhibition of $PGE_2$ or other prostaglandin synthesis is not desired, such as the gastric mucosal, neural or renal cells.

As used herein, the term "hop extract" refers to the solid material resulting from (1) exposing a hops plant product to a solvent, (2) separating the solvent from the hops plant products, and (3) eliminating the solvent.

As used herein, the term "solvent" refers to a liquid of aqueous or organic nature possessing the necessary characteristics to extract solid material from the hop plant product. Examples of solvents would include, but are not limited to, water, steam, superheated water, methanol, ethanol, hexane, chloroform, methylene chloride, liquid supercritical $CO_2$, liquid $N_2$, or combinations of such materials.

As used herein, the term "$CO_2$ extract" refers to the solid material resulting from exposing a hops plant product to a liquid or supercritical $CO_2$ preparation followed by the removing of the $CO_2$.

As used herein, the term "spent hops" refers to the solid and hydrophilic residue from extract of hops.

As used herein, the term "alpha acid" refers to compounds collectively known as humulones and can be isolated from hops plant products including, among others, humulone, cohumulone, adhumulone, hulupone, and isoprehumulone.

As used herein, the term "isoalpha acid" refers to compounds isolated from hops plant products and which subsequently have been isomerized. The isomerization of alpha acids can occur thermally, such as boiling. Examples of isoalpha acids include, but are not limited to, isohumulone, isocohumulone, and isoadhumulone.

As used herein, the term "reduced isoalpha acid" refers to alpha acids isolated from hops plant product and which subsequently have been isomerized and reduced, including cis and trans forms. Examples of reduced isoalpha acids (RIAA) include, but are not limited to, dihydro-isohumulone, dihydro-isocohumulone, and dihydro-isoadhumulone.

As used herein, the term "tetra-hydroisoalpha acid" refers to a certain class of reduced isoalpha acid. Examples of tetra-hydroisoalpha acid (THLAA) include, but are not limited to, tetra-hydro-isohumulone, tetra-hydro-isocohumulone and tetra-hydro-isoadhumulone.

As used herein, the term "hexa-hydroisoalpha acid" refers to a certain class of reduced isoalpha acid. Examples of hexa-hydroisoalpha acids (HHIAA) include, but are not limited to, hexa-hydro-isohumulone, hexa-hydro-isocohumulone and hexa-hydro-isoadhumulone.

As used herein, the term "beta-acid fraction" refers to compounds collectively known as lupulones including, among others, lupulone, colupulone, adlupulone, tetrahydroisohumulone, and hexahydrocolupulone.

As used herein, the term "essential oil fraction" refers to a complex mixture of components including, among others, myrcene, humulene, beta-caryophyllene, undecane-2-on, and 2-methyl-but-3-en-ol.

As used herein, "conjugates" of compounds means compounds covalently bound or conjugated to a member selected from the group consisting of mono- or di-saccharides, amino acids, sulfates, succinate, acetate, and glutathione. The mono- or di-saccharide can be a member selected from the group consisting of glucose, mannose, ribose, galactose, rhamnose, arabinose, maltose, and fructose.

The invention relates to using hops extracts to reduce toxicity associated with the administration of NSAIDs. Hop extraction in one form or another goes back over 150 years to the early nineteenth century when extraction in water and ethanol was first attempted. Even today, an ethanol extract is available in Europe, but by far the predominant extracts are organic solvent extracts (for example, hexane) and $CO_2$ extracts (supercritical and liquid). $CO_2$ (typically at 60 bars pressure and 50 to 10° C.) is in a liquid state and is a relatively mild, non-polar solvent highly specific for hop soft resins and oils. Beyond the critical point, typically at 300 bars pressure and 60° C., $CO_2$ has the properties of both a gas and a liquid and is a much stronger solvent. The composition of the various extracts is compared in Table 2.

At its simplest, hop extraction involves milling, pelleting and re-milling the hops to spread the lupulin, passing a solvent through a packed column to collect the resin components and finally, removal of the solvent to yield a whole or "pure" resin extract.

TABLE 2

| | Hop extracts (Percent w/w) | | | |
|---|---|---|---|---|
| Component | Hops | Organic Solvent | Super-Critical $CO_2$ | Liquid $CO_2$ |
| Total resins | 12-20 | 15-60 | 75-90 | 70-95 |
| Alpha-acids | 2-12 | 8-45 | 27-55 | 30-60 |
| Beta-acids | 2-10 | 8-20 | 23-33 | 15-45 |
| Essential oils | 0.5-1.5 | 0-5 | 1-5 | 2-10 |
| Hard resins | 2-4 | 2-10 | 5-11 | None |
| Tannins | 4-10 | 0.5-5 | 0.1-5 | None |
| Waxes | 1-5 | 1-20 | 4-13 | 0-10 |
| Water | 8-12 | 1-15 | 1-7 | 1-5 |

The main organic extractants are strong solvents and in addition to virtually all the lupulin components, they extract plant pigments, cuticular waxes, water and water-soluble materials.

Supercritical $CO_2$ is more selective than the organic solvents and extracts less of the tannins and waxes and less water and hence water-soluble components. It does extract some of the plant pigments like chlorophyll but rather less than the organic solvents do. Liquid $CO_2$ is the most selective solvent used commercially for hops and hence produces the most pure whole resin and oil extract. It extracts hardly the hard resins or tannins, much lower levels of plant waxes, no plant pigments and less water and water-soluble materials.

As a consequence of this selectivity and the milder solvent properties, the absolute yield of liquid $CO_2$, extract per unit weight of hops is less than when using the other mentioned solvents. Additionally, the yield of alpha acids with liquid $CO_2$ (89-93%) is lower than that of supercritical $CO_2$ (91-94%) or the organic solvents (93-96%). Following extraction, there is the process of solvent removal, which for organic solvents involves heating to cause volatilization. Despite this, trace amounts of solvent do remain in the extract. The removal of $CO_2$, however, simply involves a release of pressure to volatize the $CO_2$.

Figure 3:
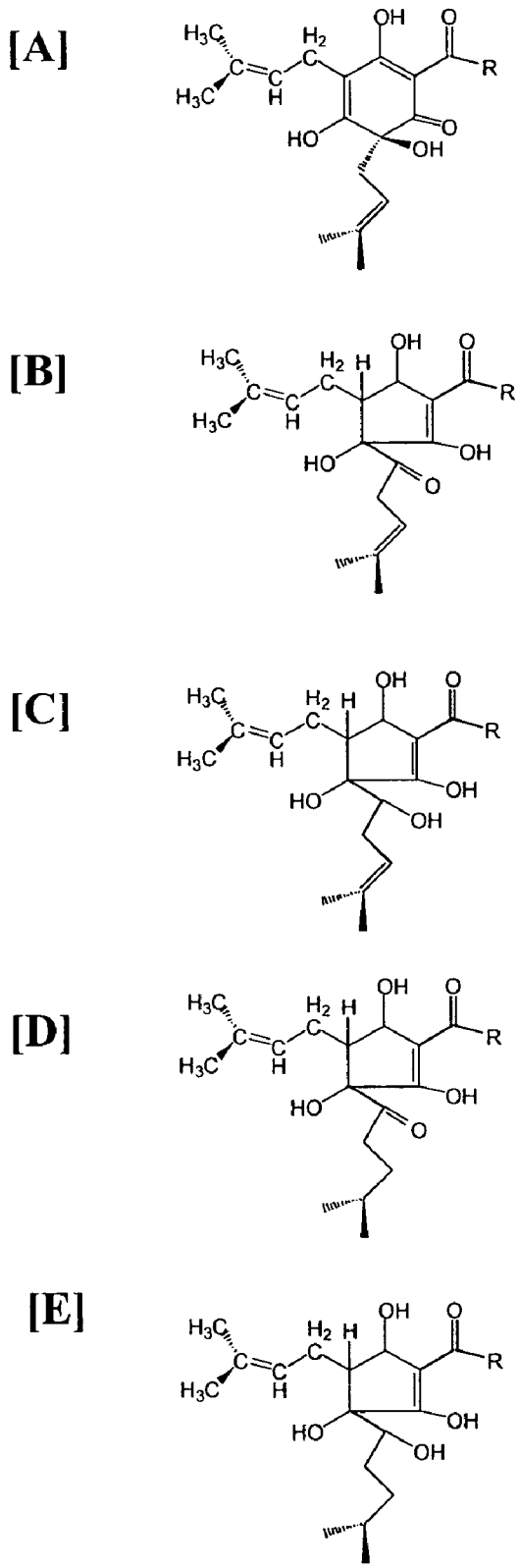
FIG. 3 illustrates exemplary fractions isolated or derived from hops.

As shown in FIG. 3, hops $CO_2$ extracts can be fractionated into components, including hops oils, beta acids, and alpha acids. Hops oils include, but are not limited to, humulene, beta-caryophyllene, mycrene, farnescene, gamma-cadinene, alpha-selinene, and alpha-cadinene. Beta acids include, but are not limited to, lupulone, colupulone, adlupulone, tetrahydroisohumulone, and hexahydrocolupulone, collectively known as lupulones. Beta acids can be isomerized and reduced. Beta acids are reduced to give tetra-beta acids. Alpha acids include, but are not limited to, humulone, cohumulone, adhumulone, hulupone, and isoprehumulone. Alpha acids can be isomerized to give isoalpha acids. Iso-alpha acids can be reduced to give reduced-isoalpha acids, tetra-hydroisoalpha acids, and hexa-hydroisoalpha acids.

The identification of humulone from hops extract as an inhibitor of bone resorption is reported in To be et al. (*Biosci. Biotech. Biochem* 61(1):158-159 (1997)). Later studies by the same group characterized the mechanism of action of humulone as inhibition of COX-2 gene transcription following TNFalpha stimulation of MC3T3, E1 cells (Yamamoto, *FEBS Letters* 465:103-106 (2000)). It was concluded that the action of humulone (also humulon) was similar to that of glucocorticoids, but that humulone did not function through the glucocorticoid receptor. While these results establish that humulone inhibits $PGE_2$ synthesis in MC3T3 cells (osteoblasts) at the gene level, one skilled in the art would not assume that these results would necessarily occur in immune inflammatory cells or other cell lines. As disclosed herein, hops compounds and derivatives exhibit a high degree of tissue selectivity in target and non-target cells. Furthermore, the hops derivatives described in the present invention are structurally distinct from the alpha acid humulone.

The invention provides compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Fractions isolated or derived from hops, include, but are not limited to, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters.

Compounds of the fractions isolated or derived from hops can be represented by a supragenus below:

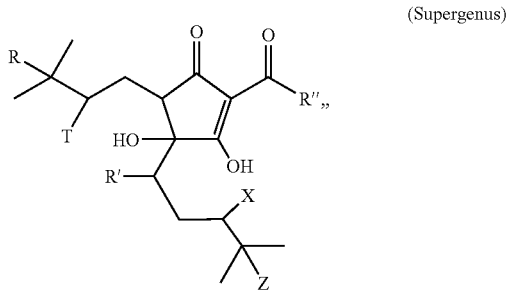

(Supergenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and p orbital, with the proviso that if one of R, T, X, or Z is a p orbital, then the adjacent R, T, X, or Z is also a p orbital, thereby forming a double bond.

In another embodiment, compounds of the fractions isolated or derived from hops can be represented by a genus below:

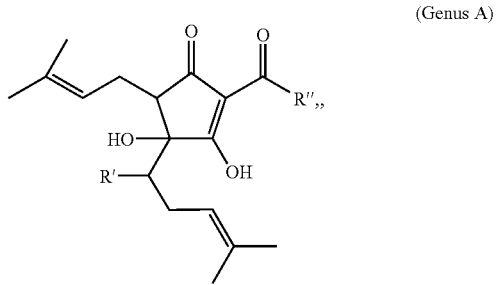

(Genus A)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus A structures include isoalpha acids such as isohumulone, isocohumulone, isoadhumulone, and the like, and reduced isoalpha acids such as dihydro-isohumulone, dihydro-isocohumulone, dihydro-isoadhumulone, and ether or ester conjugates or halogenated modifications of the double bond.

In yet another embodiment, compounds of the fractions isolated or derived from hops can be represented by a genus below:

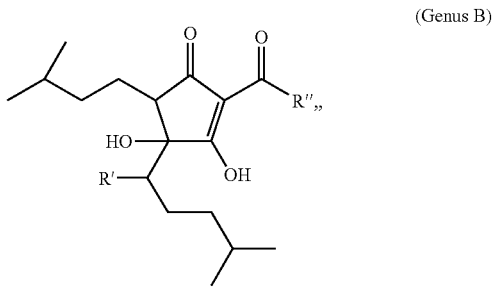

(Genus B)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$. Exemplary Genus B structures include tetra-hydroisoalpha acids such as tetra-hydro-isohumulone, tetra-hydro-isocohymulone and tetra-hydro-isoadhumulone, and the like, and hexa-hydroisoalpha acids such as hexa-hydro-isohumulone, hexa-hydro-isocohumulone and hexa-hydro-isoadhumulone, and ether or ester conjugates.

As shown in FIG. 3, examples of compounds of an ingredient isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. The preferred compounds can bear substituents, as shown in the formula above.

Hops derivatives are known compounds occurring naturally in plants and found in food products and beverages. They may be prepared by any of the extraction and processing methods known in the art. Hops derivatives can be prepared directly from plant material in any known manner. The hops derivatives may be purified by methods known in the art, for example, by recrystallization from aqueous organic solvents such as aqueous alcohols. Synthetic modifications of hops derivatives may be prepared according to methods known in the pharmaceutical art of drug modification.

The invention also provides compositions containing an analgesic and/or inflammatory compound or drug, for example, an NSAID, and a fraction or compounds isolated or derived from hops. For example, the invention provides compositions containing a fraction or compounds isolated or derived from hops, as disclosed herein, and one or more analgesic and/or inflammatory compounds or drugs such as NSAIDs. In a particular embodiment, the invention provides a composition comprising an isoalpha acid or reduced isoalpha acid isolated from hops and a non-steroidal anti-inflammatory drug. The isoalpha acid can be selected from isohumulone, isocohumulone, and isoadhumulone. In another embodiment of the invention, the reduced isoalpha acid can be selected from dihydro-isohumulone, dihydro-isocohumulone, and dihydro-isoadhumulone.

Exemplary analgesic and/or anti-inflammatory compounds or drugs include, but are not limited to, the following substances: the salicylates aspirin, salicylic acid, methyl salicylate, difulunisal, salsalate, olsalazine, and sulfasalazine; para-aminophenol derivatives acetanilide, acetaminophen, and phenacetin; the fenamates mefenamic acid, meclofenamate and sodium meclofenamate; the heteroaryl acetic acid derivatives tolmetin, ketorolac and diclofenac; the propionic acid derivatives ibuprofen, naproxen, sodium daproxen, fenoprofen, ketoprofen, flurbioprofen/flurbiprofen, and oxaprozin; the enolic acids represented by oxicam derivatives piroxicam, meloxicam, tenoxicam, ampiroxicam, droxicam and pivoxicam; the pyrazolon derivatives phenylbutazone, oxyphenbutazone, anitpyrine, aminopyrine and dipyrone; the coxibs celecoxib, and rofecoxib; nabumetone; apazone; nimensulide; indomethacin; sulindac; etodolac; diflunisal, isobutylphenyl propionic acid, and any other substances used in the treatment of pain and inflammatory conditions that cause or promote gastro-intestinal damage. As used herein, a non-aspirin, non-steroidal anti-inflammatory compound specifically excludes aspirin, acetylsalicylic acid.

Also in accordance with the present invention there are provided pharmaceutical compositions comprising an effective amount of hops derivatives optionally in combination with a pharmaceutical diluent or adjuvant. Further in accordance with the present invention, there are provided pharmaceutical compositions comprising an effective amount of hops derivatives in combination with one or more analgesic and/or anti-inflammatory compound(s) in an effective and tolerated amount and concentration.

The invention additionally provides pharmaceutical compositions comprising an effective amount of hops derivatives in combination with one or more compatible compound(s) effective in the treatment of stress conditions. Such compositions can be used, for example, for the treatment of ulcers, and to reduce the formation of gastro-intestinal ulcers whether chemically or stress-induced.

Dosage

Further in accordance with the present invention there are provided pharmaceutical formulations of oral dosage forms comprising an effective amount of hops derivatives for release of the active ingredient at a desired site in the gastro-intestinal tract, for instance either in the stomach and/or duodenum according to known formulation techniques, e.g. slow releasing tablets. Still further in accordance with the invention, there are provided pharmaceutical compositions comprising an effective tolerated amount of hops derivatives and a known compound effective in preventing ulcer formation and/or a known compound effective in thereapeutically treating ulcers and/or a known compound(s) effective in relieving the symptoms associated with ulcers, such as an antacid, e.g. aluminum hydroxide. Due to its low toxicity, high dosages of hops derivatives can be employed to produce useful results, depending upon the particular effect that is desired.

Hops derivatives are particularly suitable for oral administration. Therefore, hops derivatives can be formulated for oral use, namely: tablets, coated tablets, dragees, capsules, powders, granulates and soluble tablets, and liquid forms, for example, suspensions, dispersions or solutions, optionally together with an additional active ingredient, such as one or more analgesic and/or anti-inflammatory compound(s).

The invention extends to a method of preparing such pharmaceutical compositions as described herein and compositions when so prepared. The compositions may be manufactured by a method which comprises mixing hops derivatives with a pharmaceutically acceptable carrier or auxiliary, and optionally with an analgesic and/or anti-inflammatory substance and/or another compound(s). Methods for preparing a pharmaceutical composition are well known to those skilled in the art (see, for example, Genarro, ed., *Remington's Pharmaceutical Sciences*, 18th ed., Mack Publishing Co., Easton, Pa. (1990)).

The selected dosage level will depend upon the activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, for example, two to four separate doses per day. It will be understood, however, that the specific dose level for any particular patient will depend upon a variety of factors including body weight, general health, diet, time and route of administration, combination with other compositions and the severity of the particular condition being treated or prevented. The efficacious dose may be administered prior to, with, or subsequent to the NSAID that causes gastropathy.

The invention provides methods that include delivering an effective amount of hops fractions, hops compounds, or hops derivatives alone or in combination with one or more NSAID. For example, a daily dose of compositions of the invention can be formulated to deliver about 0.5 to about 10,000 mg of a hops fraction, for example, alpha acid, isoalpha acid, reduced isoalpha acid, tetra-hydroisoalpha acid, hexa-hydroisoalpha acid, beta acid, spent hops, or other hops fractions, per day. In particular, an effective daily dose of compositions can be formulated to deliver about 50 to about 7500 mg of hops fraction, for example, alpha acids, isoalpha acid, reduced isoalpha acid, tetra-hydroisoalpha acid, hexa-hydroisoalpha acid, beta acid, spent hops, or other hops fractions, per day. For example, an effective daily dose of compositions can be formulated to deliver about 100 mg to about 5000 mg, about 200 mg to about 3000 mg, about 300 mg to about 2000 mg, about 500 to about 1000 mg of hops fraction per day. In one embodiment, the effective daily dose is administered once or twice a day. A certain embodiment provides a composition comprising about 0.5 to about 500 mg of isoalpha acid or reduced isoalpha acid, for example, about 50 to about 300 mg or about 100 to about 200 mg of isoalpha acid or reduced isoalpha acid per day. In another embodiment, the invention provides a composition comprising about 10 to about 3000 mg of reduced isoalpha acid, tetra-hydroisoalpha acid, or hexa-hydroisoalpha acid per day, for example, about 50 to about 2000 mg, about 100 to about 1000 mg, about 200 to about 750 mg, or about 250 to about 500 mg of reduced isoalpha acid, tetra-hydroisoalpha acid, or hexa-hydroisoalpha acid per day. Yet another certain embodiment provides a composition comprising about 50 to about 7500 mg of spent hops per day, for example, about 100 to about 6000 mg, about 200 to about 5000 mg, about 300 to about 3000 mg, about 500 to about 2000 mg, or about 1000 to about 1500 mg of spent hops per day.

A composition of embodiments for topical application can contain about 0.001 to about 10 weight percent, for example, about 0.01 to about 5 weight percent, or about 0.1 to about 1 weight percent, of a hops derivative. Such compositions can produce serum concentrations in the range of about 0.0001 to about 10 $\mu$M, for example, about 0.001 to about 5 $\mu$M, about 0.01 to 1 $\mu$M, or about 0.1 to about 0.5 $\mu$M of a fraction isolated or derived from hops or conjugate thereof.

Formulations

Compositions of the invention can be administered in the form of a dietary supplement or therapeutic composition. The compositions may be administered orally, topically, transdermally, transmucosally, parenterally, and the like, in appropriate dosage units, as desired. Compositions for dietary application may include various additives such as other natural components of intermediary metabolism, vitamins and minerals, as well as inert ingredients such as talc and magnesium stearate that are standard excipients in the manufacture of tablets and capsules. For example, one embodiment comprises active ingredients of compositions of the invention in combination with glucosamine or chondrotin sulfate.

As used herein, "pharmaceutically acceptable carrier" includes solvents, dispersion media, coatings, isotonic and absorption delaying agents, sweeteners and the like, suitable for administration to an individual. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. It is understood that formulations contain components that are compatible with the active ingredients. In one embodiment, talc, and magnesium stearate are included in the formulation. Other ingredients known to affect the manufacture of a composition of the invention as a dietary bar or functional food can include flavorings, sugars, amino-sugars, proteins and/or modified starches, as well as fats and oils.

Dietary supplements, lotions or therapeutic compositions of embodiments of the invention can be formulated in any manner known by one of skill in the art. In one embodiment, the composition is formulated into a capsule or tablet using techniques available to one of skill in the art. In capsule or tablet form, the recommended daily dose for an adult human or animal can be contained in one to six capsules or tablets. The compositions can also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, compositions of the invention can be formulated into cereals, snack items such as chips, bars, gumdrops, chewable candies or slowly dissolving lozenges. Compositions of the invention can be used for the treatment of inflammation-based diseases, both acute and chronic. Particularly useful formulations of compositions of the invention can reduce the inflammatory response and thereby promote healing of, or prevent further damage to, the affected tissue. A pharmaceutically acceptable carrier can also be used in the compositions and formulations of the invention.

The invention also provides a method of treatment of patients suffering from, or susceptible to, ulcerogenic type disorders of the stomach and intestines, particularly acute and chronic gastric and duodenal ulcers and related conditions, which comprise administering to the patient an effective amount of hops derivatives optionally together with additional active ingredients such as analgesic and/or anti-inflammatory compounds or drugs.

Compositions of the invention can be used, for example, for the treatment of inflammation in a subject, and for treatment of other inflammation-associated disorders, such as an analgesic in the treatment of pain and headaches, or as an antipyretic for the treatment of fever. Compositions of the invention can be used to treat arthritis, including but not limited to rheumatoid arthritis, spondyloathopathies, gouty arthritis, osteoarthritis, systemic lupus erythematosis, and juvenile arthritis.

Compositions of the invention can be used to prevent or treat NSAID-induced gastropathy in a mammal. For example, chronic, oral dosing of aspirin is associated with the development of ulcers. When administered with the present invention, ulcer development can be ameliorated or averted.

As disclosed herein, NSAID inhibition of gastric $PGE_2$ biosynthesis is significantly attenuated with concomitant exposure to hops derivatives (see Examples 5 and 6). As further disclosed herein, the combination of hops derivatives and NSAIDS exhibit increased therapeutic indices (see Examples 7 and 8). Hops derivatives were also found to decrease ulcer formation and inhibit NSAID-induced gastric damage (see examples 9 and 10). Therefore, the formation of gastric ulceration can be ameliorated, prevented or halted without negatively affecting the anti-inflammatory activity of the NSAID. Since compositions of the invention can affect NSAID gastropathy, embodiments can also be useful for treating and preventing a variety of disorders including, but not limited to, autoimmune, inflammatory, neurological, infectious and cardiovascular diseases, and cancers.

The invention provides a composition containing a fraction isolated or derived from hops, as disclosed herein, in combination with a second component. In one embodiment, the invention provides a composition comprising a fraction isolated or derived from hops and a non-aspirin, non-steroidal anti-inflammatory compound. The fraction isolated or derived from hops can be selected from the group consisting of alpha acids, isoalpha acids, reduced isoalpha acids, tetrahydroisoalpha acids, hexa-hydroisoalpha acids, beta acids, and spent hops.

The fraction isolated or derived from hops can also be a compound of a supragenus having the formula:

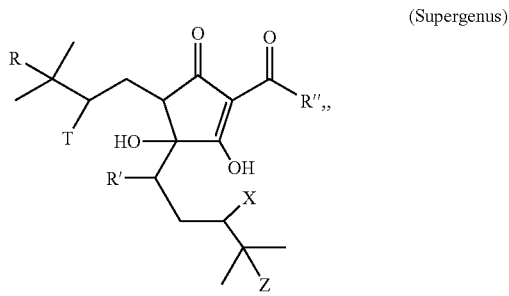

(Supergenus)

wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and p orbital, with the proviso that if one of R, T, X, or Z is a p orbital, then the adjacent R, T, X, or Z is also a p orbital, thereby forming a double bond.

In still another embodiment, the fraction isolated or derived from hops can contain a compound of Genus A having the formula:

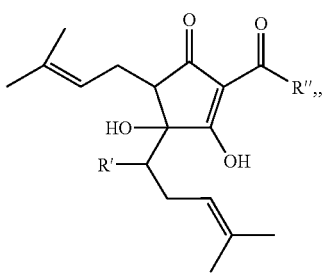

(Genus A)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In yet another embodiment of the invention, the fraction isolated or derived from hops can be a compound of Genus B having the formula:

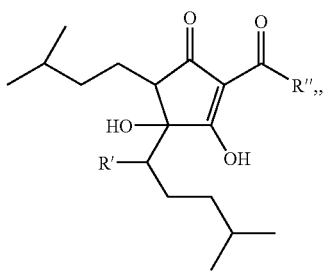

(Genus B)

wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

In an additional embodiment, the fraction isolated or derived from hops can be a compound selected from the group consisting of humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. A composition of the invention can contain specific ranges of the active components, as disclosed herein.

A composition of the invention that contains a fraction isolated or derived from hops can be combined with a non-aspirin, nonsteroidal anti-inflammatory compound. Such a compound can be selected from the group consisting of salicylic acid, methyl salicylate, difulunisal, salsalate, olsalazine, sulfasalazine, acetanilide, acetaminophen, phenacetin, mefenamic acid, sodium meclofenamate, tolmetin, ketorolac, diclofenac, ibuprofen, naproxen, sodium daproxen, fenoprofen, ketoprofen, flurbioprofen, oxaprozin, piroxicam, meloxicam, tenoxicam, ampiroxicam, droxicam, pivoxicam, phenylbutazone, oxyphenbutazone, anitpyrine, aminopyrine, dipyrone, celecoxib, rofecoxib, nabumetone, apazone, nimensulide, indomethacin, sulindac, and etodolac. A composition of the invention can further comprises a pharmaceutically acceptable carrier. Such a composition can be formulated for administration orally, topically, parenterally, or rectally.

In another embodiment, the invention provides a composition comprising a reduced isoalpha acid isolated from hops and a non-steroidal anti-inflammatory compound. The reduced isoalpha acid can be, for example, dihydro-isohumulone, dihydro-isocohumulone, and dihydro-isoadhumulone.

The invention additionally provides methods using the compositions of the invention disclosed herein. In one embodiment, the invention provides a method of producing an analgesic and an anti-ulcerogenic effect in a mammal, comprising administering to the mammal an amount of a fraction isolated or derived from hops sufficient to produce an analgesic and anti-ulcerogenic effect and a nonsteroidal anti-inflammatory compound, whereby administration of the fraction isolated or derived from hops reduces gastric toxicity associated with the non-steroidal anti-inflammatory compound. As disclosed herein, the fraction isolated or derived from hops can be administered concomitantly with the non-steroidal anti-inflammatory compound. Alternatively, the fraction isolated or derived from hops can be administered after the administration of the non-steroidal anti-inflammatory compound or before the administration of the non-steroidal anti-inflammatory compound.

In another embodiment, the invention provides a method of reducing gastric toxicity associated with a non-steroidal anti-inflammatory compound by administering a fraction isolated or derived from hops to an individual being treated with a non-steroidal anti-inflammatory compound. The invention additionally provides a method of reducing gastroenteropathy by administering a fraction isolated or derived from hops to an individual exhibiting a sign or symptom associated with gastroenteropathy The gastroenteropathy can, for example, involve ulceration. The ulceration can be induced, for example, by food, an herb, bacteria, fungi or a drug. It is understood that a method of the invention can be used to ameliorate a sign or symptom associated with gastropathy, gastroenteropathy, or gastric distress or discomfort associated with a gastrointestinal irritant, as disclosed herein.

In one embodiment, the invention provides a method of reducing gastric toxicity associated with a non-steroidal anti-inflammatory compound such as a NSAID by administering a fraction isolated or derived from hops to an individual being treated with a non-steroidal anti-inflammatory compound. A method can similarly be used to reduce gastric toxicity or gastroenteropathy associated with a gastrointestinal irritant. Various hops derivatives or a fraction isolated or derived from hops can be used to reduce gastric toxicity associated with a non-steroidal anti-inflammatory compound. The fraction isolated or derived from hops, for example, isoalpha acid or reduced isoalpha acid, can be administered concomitantly with a non-steroidal anti-inflammatory compound such as a NSAID. Such a concomitant administration can be in the same formulation or in different formulations. Alternatively, the hops derivatives or fraction isolated or derived from hops can be administered after a non-steroidal anti-inflammatory compound has been administered, for example, within a few minutes to a few hours to a few days of administration of a non-steroidal anti-inflammatory compound. The fraction isolated or derived from hops can also be administered after gastropathy from taking a non-steroidal anti-inflammatory compound has developed. In addition, a hops derivative or fraction isolated or derived from hops can be administered before a non-steroidal anti-inflammatory compound is administered, for example, as a prophylactic to prevent or reduce the severity of onset of non-steroidal anti-inflammatory compound-induced gastropathy. Such administration can be a few minutes to a few hours to a few days prior to administration of a non-steroidal anti-inflammatory compound. If the fraction isolated or derived from hops is administered prior to administration of a non-steroidal anti-inflammatory compound, it is understood that the administration is within a timeframe such that the administration of the fraction isolated or derived from hops is effective at ameliorating non-steroidal anti-inflammatory compound-induced gastropathy or reducing the severity of the onset of non-steroidal anti-inflammatory compound-induced gastropathy. The fraction isolated or derived from hops is generally administered less than 7 days prior to the initial administration of the non-steroidal anti-inflammatory compound, for example, less than 6 days, less than 5 days, less than 4 days, less than 3 days, or less than 2 days prior to administration of the non-steroidal anti-inflammatory compound. In particular, the fraction isolated or derived from hops can be administered within 24 hours of administration of the non-steroidal anti-inflammatory compound.

Besides being useful for human treatment, embodiments of the invention are also useful for treatment of other animals, including horses, dogs, cats, birds, sheep, pigs, and the like. Formulations for the treatment of inflammation can inhibit the induction and activity of COX-2 with little effect on the synthesis of $PGE_2$ in the gastric mucosa. Historically, the NSAIDs used for treatment of inflammation lacked the specificity of inhibiting COX-2 without affecting $PGE_2$ synthesis in gastric mucosal cells. Therefore, these drugs irritated and damaged the gastrointestinal system when used for extended periods. Such contraindications are not associated with the present invention and therefore, the formulations described may be used for extended periods with limited or no gastropathy. Administration can be by any method available to the skilled artisan, for example, by oral, topical, transdermal, transmucosal, or parenteral routes.

As used herein, "reducing inflammation" refers to decreasing, ameliorating or inhibiting an inflammatory response. One skilled in the art can readily recognize a reduction in a sign or symptom associated with an inflammatory response. Reducing inflammation can refer to decreasing the severity of a sign or symptom associated with inflammation as well as inhibiting inflammation so that few or no symptoms associated with inflammation are presented. As used herein, "gastropathy" refers to a disease of the stomach. As used herein, "gastroenteropathy" refers to a disorder of the alimentary canal, the tubular passage that extends from the mouth to the anus and functions in digestion and absorption of food and elimination of residual waste. As used herein, "ulcerogenic disorder" refers to a disorder involving a gastrointestinal ulcer. The gastrointestinal ulcer can, for example, result from exposure to an ulcerogenic substance such as an ulcerogenic chemical, an ulcerogenic environmental stimulus, an infection such as a bacterial infection, for example, *Helicobacter pylori*, or a stressed-induced ulcer. Such an ulcerogenic substance can be, for example, a drug or compound such as a non-steroidal anti-inflammatory compound or NSAID, food, an herb, bacteria, fungi, or other stimuli that induce ulcers. For example, the drug Fosmax is used to treat osteoporosis and causes adverse gastrointestinal effects. Therefore, a composition of the invention can be used to ameliorate gastroenteropathy caused by a gastrointestinal irritant such as a drug. Although the invention is exemplified with ameliorating gastropathy associated with NSAIDs, it is understood that the composition and methods disclosed herein can similarly be used for ameliorating gastropathy and/or gastroenteropathy associated with a variety of gastrointestinal irritants.

As disclosed herein, a composition of the invention containing a fraction isolated or derived from hops, and optionally in combination with other components, can ameliorate a sign or symptom associated with gastropathy and/or gastroenteropathy. It is understood by those skilled in the art that a composition of the invention can be advantageously used to ameliorate gastroenteropathy associated with chemical, environmental, infection and/or emotionally stressful insults. For example, a composition of the invention can be used to ameliorate gastropathy and/or gastroenteropathy associated with a gastrointestinal irritant. Such an irritant can include, for example, spices used for seasoning food, herbal preparations, alcohol, tobacco, stress, or other well known gastrointestinal irritants. A number of gastrointestinal irritants are well known to those skilled in the art, including, but not limited to, foods and herbal preparations, including spices; stress and lifestyle, drugs, bacteria such as *H. pylori* and ulcer formation, and the like, (see, for example, Myers et al., *Am. J. Gastroenterol.* 82:211-214 (1987); Pippa et al., *Scand. J. Gastroenterol. Suppl.* 167:32-35 (1989); Sivri, *Fundam. Clinic. Pharmacol.* 18:23-31 (2004); Bermejo et al., *Rev. Esp. Enferm. Dig.* 95: 621-624 and 625-628 (2003)).

As disclosed herein, various spices have been found to be inhibitory of $PGE_2$ in the AGS cell model (see Examples 14-16). In combination with RIAA or other hops derivatives, the spices are expected to be less gastrotoxic. For example, both ginger and capsasin analyzed in RAW and AGS cell models show inhibitory activity. Hence, RIAA, or other fractions isolated or derived from hops, can antagonize activity in non-target cells (for example, gastric cells) and synergize in target cells (for example inflammatory cells). Therefore, a composition of the invention containing a fraction isolated or derived from hops can be used to decrease gastric toxicity and/or gastric discomfort associated with a gastric irritant such as a spice. For example, an $IC_{50}$ of 4 was observed for rosemary, an IC50>25 was observed for RIAA, and an IC50>25 for the combination, which shows that RIAA can safen a spice. Thus, a composition of the invention can be ingested with a spice, or mixed with a spice prior to ingestion or addition to food. In addition, a composition of the invention can be administered in the form of chewing gum to alleviate gastric distress associated with ingestion of a spice. Such administration can similarly be applied to other gastric irritants that induce gastrotoxicity and/or gastropathy.

A composition of the invention containing a fraction isolated or derived from hops, which have antimicrobial activities, can be used to both eradicate a gastric ulcer and promote gastric healing. In another embodiment of the invention, a composition of the invention can be used in the form of an ointment or hypoallergenic paste or cream to treat ulcerations or wounds of the skin or tissues, including dental applications in mouth ulcers.

As disclosed herein, a fraction isolated or derived from hops can be used to ameliorate a sign or symptom associated with gastroenteropathy, for examples, ulcers formed in the stomach or intestine. For example, the invention provides a method of reducing a sign or symptom associated with gastroenteropathy by administering a fraction isolated or derived from hops to an individual exhibiting a sign or symptom associated with gastroenteropathy.

In addition to a fraction isolated or derived from hops, a composition of the invention can further comprise a second component. An example of such a second component is rosemary, an extract or compound derived from rosemary. A composition of the invention can thus contain a fraction isolated or derived from hops and can further comprise an effective amount of rosemary, rosemary extract, or compounds derived from rosemary. Thus, in addition to a fraction isolated or derived from hops, a composition of the invention can further contain rosemary, rosemary extract, or those compounds known to be found in rosemary or extracts of rosemary. These include 1,8-cineole, 19-alpha-hydroxyursolic acid, 2-β-hydroxyoleanolic acid, 3-O-acetyloleanolic acid, 3-O-acetylursolic acid, 6-methoxy-luteolin-7-glucoside, 6-methoxyluteolin, 6-methoxyluteolin-7-glucoside, methoxyluteolin-7-methylether, 7-ethoxy-rosmanol, 7-methoxyrosmanol, alpha-amyrin, alpha-humulene, alpha-hydroxyhydrocaffeic acid, alpha-pinene, alpha-terpinene, alpha-terpinenyl acetate, alpha-terpineol, alpha-thujone, apigenin, apigenin-7-glucoside, curcumene, benzyl-alcohol, β-amyrenone, β-amyrin, β-elemene, β-pinene, betulin, betulinic acid, borneol, bornyl-acetate, caffeic acid, camphene, camphor, carnosic acid, camosol, carvacrol, carvone, caryophyllene, caryophyllene-oxide, chlorogenic acid, diosmetin, gamma-terpinene, hesperidin, isoborneol, limonene, luteolin, luteolin-3'-O-(3"-O-acetyl)-β-D-glucuronide, luteolin-3'-O-(4"-O-acetyl)-β-D-glucuronide, luteolin-3'-O-β-D-glucuronide, luteolin-7-glucoside, methyl-eugenol, myrcene, neo-chlorogenic acid, nepetin, octanoic acid, oleanolic acid, p-cymene, piperitenone, rosmanol, rosmaric acid, rosmaricine, rosmaridiphenol, rosemarinic acid, rosmarinol, rosmariquinone, sabinene, sabinyl acetate, salicylates, salicylic acid-2-β-D-glucoside, squalene, terpinen-4-ol, terpinolene, thymol, trans-anethole, trans-carveol, ursolic acid, verbenone, and zingiberene.

In a composition containing a fraction isolated or derived from hops and rosemary or an extract or compound derived therefrom, the composition can be formulated to deliver about 0.5 to 5000 mg of rosemary, an extract of rosemary, or rosemary-derived compound per day. In particular, an effective daily dose can be formulated to deliver about 5 to 2000 mg of rosemary, an extract of rosemary, or rosemary-derived compound per day. For example, the composition can be formulated to provide an effective daily dose to be administered once or twice a day. In a particular embodiment, a composition can contain about 75 mg of rosemary extract or rosemary-derived compound or derivative, to be administered once or twice a day.

A composition of the invention can further include a triterpene, such as oleanolic acid. In a particular embodiment, the composition can contain about 0.01 to 500 mg of rosemary extract and about 0.01 to 500 mg of oleanolic acid. For example, a particular embodiment provides a composition capable of producing concentrations in target tissues of 0.1 to 10 µg/g tissue of rosemary extract and about 0.1 to 25 µg/g tissue of oleanolic acid.

In still a further embodiment, a composition of the invention can further contain a triterpene species that is selected from the group consisting of 18-a-glycyrrhetinic acid, 18-β-glycyrrhetinic acid, 2-a-3-a-dihydrooxyurs-12-3n-28-onic acid, 3-a-hydroxyursolic acid, 3-oxo-ursolic acid, betulin, betulinic acid, celastrol, eburicoic acid, friedelin, glycyrrhizin, gypsogenin, oleanolic acid, oleanolic acid-3-acetate, pachymic acid, pinicolic acid, sophoradiol, soyasapogenol A, soyasapogenol B, tripterin, triptophenolide, tumulosic acid, ursolic acid, ursolic acid-3-acetate, uvaol, and β-sitosterol. The triterpene species can optionally be conjugated to a member selected from the group consisting of mono- or di-saccharides, amino acids, sulfates, succinate, acetate, and glutathione.

In a particular embodiment, the composition can comprise about 0.5 to 10000 mg or about 50 to 7500 mg of the fraction isolated or derived from hops. Moreover, the composition can comprise, in addition to a fraction isolated or derived from hops, about 0.5 to 5000 mg of a second component, or about 5 to 2000 mg of a second component, wherein the second component is selected from the group consisting of rosemary, extract derived from rosemary, and a compound derived from rosemary. In addition, the composition can comprise about 0.001 to 10 weight percent of a first component containing a fraction isolated or derived from hops, or about 0.1 to 1 weight percent of the first component. Also, the composition can comprise about 0.001 to 10 weight percent of a second component selected from rosemary, a rosemary extract or a compound derived from rosemary, or about 0.1 to 1 weight percent of the second component. In another embodiment, a ratio of the first hops component to the second rosemary component can be in the range of about 100:1 to about 1:100, or in the range of about 50:1 to about 1:50

As disclosed herein (see Example 13), a composition containing a fraction isolated or derived from hops does not increase fecal calprotectin, in contrast to anti-inflammatory drugs such as NSAIDS which increase fecal calprotectin, an indicator of gastrointestinal inflammation. Such a composition containing a fraction isolated or derived from hops also contained rosemary extract and oleonolic acid in the particular embodiment examined (Example 13). Therefore, a composition containing a fraction isolated or derived from hops can be used to inhibit $PGE_2$ synthesis similar to NSAIDS while minimizing gastrointestinal inflammation.

Calprotectin is a calcium binding protein that has been found to have antimicrobial, antifungal, and antiproliferative properties and to promote apoptosis in transformed and normal cells (Yui et al., *Biol. Pharm. Bull.* 26:753-760 (2003); Poullis et al., *J. Gastroenterol. Hepatol.* 18:756-762 (2003)). At least some of its activity appears to involve the ability of calprotectin to sequester zinc, causing a localized zinc deficiency. However, data also indicate it has zinc-independent activities as well.

Calprotectin comprises 40% of the cytoplasmic protein in neutrophils, which infiltrate inflammatory sites, where they release the calprotectin (Yui et al., supra, 2003; Poullis et al., supra, 2003). It is also found in blood monocytes and tissue macrophages at sites of acute inflammation, whereas macrophages present in chronic inflammation and resident macrophages are negative for calprotectin (Yui et al., supra, 2003). Calprotectin has also been found in mucosal squamous epithelial cells and cytokine-stimulated cultured keratinocytes, suggesting that other cells may also produce this protein during inflammation (Schjerven et al., *Br. J. Dermatol.* 149:484-491 (2003)).

Calprotectin can be detected in plasma, urine, and several other bodily fluids. In normal individuals, neutrophils migrate through the mucosal membrane of the intestinal tract at the termination of their life and, therefore, a low level of fecal calprotectin is generally present. 4 4. Tibble and Bjarnason, *Drugs Today,* 37:85-96 (2001). Since it is resistant to degradation, calprotectin can also be reproducibly quantified in fecal samples (Røseth, A G. *Digest. Liver Dis.* 35:607-609 (2003).

Interest in fecal calprotectin as a diagnostic test has grown since it has been shown to be elevated in patients with gastrointestinal inflammation. For example, fecal calprotectin is significantly increased in Inflammatory Bowel Disease (IBD; >100 µg/g stool), and a positive association has also been observed between active IBD and increased calprotectin over quiescent disease (Costa et al., *Digest. Liver Dis.* 35:642-647 (2003). Research suggests that fecal calprotectin is also increased inflammation associated with colon cancer. Data comparing healthy subjects with those having Irritable Bowel Syndrome (non-inflammatory disease) and IBD suggest a cutoff indicating the presence of an organic disease is around 60 µg/g stool (Costa et al., supra, 2003; Carroccio et al., *Clin. Chem.* 49:861-867 (2003)).

Non-steroidal anti-inflammatory drugs NSAIDs can induce gastrointestinal damage, and long-term use causes inflammatory changes of the gastroduodenenal region in a high percentage of patients. Some studies suggest that up to 65% of patients taking NSAIDs regularly for more than 6 months will develop enteropathy (Tibble and Bjarnason, supra, 2001). Damage to the gastrointestinal tract appears to occur rapidly with NSAID use. For example, in one study, 19% of subjects developed gastroduodenal ulcers within 4 weeks of naproxen treatment (500 mg bid), and 41% of patients developed ulcers after 12 weeks of treatment (Goldstein et al., *Am. J. Gastroenterol.* 96:1019-1027 (2001)).

Since fecal calprotectin is an indicator of gastrointestinal inflammation, several reports have investigated the use of fecal calprotectin to detect damage from NSAIDs. In one study, fecal calprotectin was reproducibly increased over 2-fold after 7 days of naproxen treatment (Meling et al., *Scand. J. Gastroenterol.* 31:339-344 (1996)). These authors also reported that the increase in calprotectin was positively correlated to gastroduodenal mucosal inflammation as assessed by endoscopy; however, a subsequent study with naproxen reproduced the increase in calprotectin but not the endoscopy findings (Shah et al., *Gut* 48:339-346 (2001)). Fecal calprotectin has been found to be increased in 44% of subjects on chronic NSAID use, and this increase correlated significantly with 4-day excretion of $^{111}$In-labelled white cells (Tibble et al., *Gut* 45:362-366 (1999)). Taken together, these studies suggest fecal calprotectin may be a sensitive, early-stage marker of gastroduodenal damage from inflammation, such as seen with NSAIDs. Accordingly, a clinical trial was conducted to determine the effect of a composition containing a fraction isolated or derived from hops on calprotectin as a measure of gastrointestinal inflammation (see Example 13).

Assay Using AGS Cell Line

The discovery of COX-2 has made possible the design of drugs that reduce inflammation without removing the protective prostaglandins (PGs) in the stomach and kidney made by COX-1. As disclosed herein, compositions of the invention can be assessed using in vitro animal cells to assess COX-2 and COX-1 inhibitory activity employing $PGE_2$, which has cytoprotective actions and plays a role in maintaining the integrity of the gastrointestinal mucosa, as an endpoint. Secondarily, different cell types are used to confirm results. The screening process can be used to indicate compositions that have specific COX-2 activity and limited COX-1 inhibition. Compositions of embodiments of the invention can be tested in two cell types: 1) human pulmonary cells or other cell line to determine and identify optimal amounts and ratios for compositions comprising more than one component; and 2) human gastric epithelial cells (AGS cell line), a gastrointestinal tract cell line and a model system for assessing toxicity that is typically related to inhibition of COX-1, which is required for wound healing (such as ulcers). Hence, compositions of embodiments of the invention that can inhibit COX-2 or COX-2 induction can be screened by selecting compositions that have low or no activity in AGS cells and good activity in human pulmonary cells or other cell lines.

As disclosed herein, a variety of assays are available to show the effectiveness of one or more fractions isolated or derived from hops (see examples). It is understood by those skilled in the art that a fraction isolated or derived from hops, as disclosed herein, can be assayed for activity in ameliorating gastric toxicity and/or gastroenteropathy using a variety of assays well known to those skilled in the art, including those exemplified herein.

The following examples are intended to illustrate but are not intended to limit the scope of the invention.

EXAMPLE 1

AGS Gastric Mucosal Cells Constitutively Express Both Cyclooxygenase-1 and Cyclooxygenase-2

Summary—This example demonstrates that the AGS human gastric mucosal cell line, possessing constitutive expression of COX-1 and COX-2, is a model for assessing the gastrointestinal toxicity of cyclooxygenase-inhibiting compounds.

Equipment used in this example included: an OHAS Model #E01140 analytical balance, a Form a Model #F1214 biosafety cabinet (Marietta, Ohio), various pipettes to deliver 0.1 to 100 μL (VWR, Rochester, N.Y.), a cell hand tally counter (VWR Catalog #23609-102, Rochester, N.Y.), a Forma Model #F3210 $CO_2$ incubator (Marietta, Ohio), a hemacytometer (Hausser Model #1492, Horsham, Pa.), a Leica Model #DM IL inverted microscope (Wetzlar, Germany), a PURELAB Plus Water Polishing System (U.S. Filter, Lowell, Mass.), a 4° C. refrigerator (Forma Model #F3775, Marietta, Ohio), a vortex mixer (VWR Catalog #33994-306, Rochester, N.Y.), and a 37° C. water bath (Shel Lab Model #1203, Cornelius, Oreg.).

Chemicals and reagents—Prostaglandin $E_2$ EIA kit Monoclonal was purchased from Cayman Chemical (Ann Arbor, Mich.). Anti-COX-1 and anti-COX-2 rabbit polyclonal antisera were obtained from Upstate Biotechnology (CITY, NY); donkey anti-goat IgG-HRP was procured from Santa Cruz Biotechnology (City, CA). Heat inactivated Fetal Bovine Serum (FBS-HI Cat. #35-011CV), and Dulbeco's Modification of Eagle's Medium (DMEM Cat #10-013CV) was purchased from Mediatech (Herndon, Va.). All standard reagents were obtained from Sigma (St. Louis, Mo.) and were the purest commercially available.

Cell Culture—The human gastric mucosal cell line AGS was obtained from the American Type Culture Collection (ATCC number CRL-1739; Manassas, Va.) and sub-cultured according to the instructions of the supplier. The cells were routinely cultured at 37° C. with 5% $CO_2$ in RPMI 1640 containing 10% FBS, with 50 units penicillin/mL, 50 μg streptomycin/mL, 5% sodium pyruvate, and 5% L-glutamine. Exponentially growing cells were seeded into 6-well plates and grown to confluence. A 20 μL aliquot of the supernatant media was sampled for determination of $PGE_2$ content. Cells were then washed in PBS, scraped and lysed for immunoblotting.

Protein assay—Protein concentrations of cell lysates were determined using the NanoOrange Protein Quantitation Kit with bovine serum albumin as the standard (Molecular Probes, Eugene, Oreg.) according to the procedure supplied by the manufacturer. Fluorescence was determined using a Packard FluoroCount, Model BF 10000 fluorometer with the excitation filter set at 485 nm and emission filter set at 570 nm using Packard PlateReader version 3.0 software. The I-Smart program provided with the Packard PlateReader was used to calculate the protein concentration.

Immunoblotting—Western blotting of COX-1 and COX-2 was performed using PAGEr™ Gold Precast Gels (Bio Whittaker Molecular Applications (Rockland, Me.). AGS cell lysates containing approximately 60 μg protein were loaded with Laemmli Sample Buffer into the wells of the gel in a total volume of 30 μL. The vertical minigel electrophoresis chambers were made by Savant Instruments Inc. (Holbrook, N.Y.), model MV 120. Gels were run at 40 mA/plate (constant current) at room temperature until the bromophenol blue stain reached the bottom of the gel, about one hour. Gels were then blotted on the polyvinyl fluoride transfer membranes (Pall Corporation, Ann Arbor, Mich.), overnight, at 500 mA and 4° C. Precision Protein Standard molecular weight markers, unstained, broad range (BioRad, Hercules, Calif.) were used. The BioWest Extended duration chemiluminescent substrate, a non-isotopic, horseradish peroxidase substrate kit for Western blot detection (BioImaging Systems, Upland, Calif.) was used for protein visualization. Images of western blots were acquired using a UVP Epi Chemi II Darkroom (BioImaging Systems), analyzed and enhanced by LabWorks™ Image Acquisition and Analysis Software (BioImaging Systems).

$PGE_2$ assay—A commercial, non-radioactive procedure for quantification of $PGE_2$ was employed (Caymen Chemical, Ann Arbor, Mich.) and the recommended procedure of the manufacturer was used without modification. Briefly, 25 µL of the medium, along with a serial dilution of $PGE_2$ standard samples, were mixed with appropriate amounts of acetylcholinesterase-labeled tracer and $PGE_2$ antiserum, and incubated at room temperature for 18 h. After the wells were emptied and rinsed with wash buffer, 200 µL of Ellman's reagent containing substrate for acetylcholinesterase were added. The reaction was carried out on a slow shaker at room temperature for 1 h and the absorbance at 415 nm was determined. The $PGE_2$ concentration was represented as picograms per $10^5$ cells.

Figure 4:
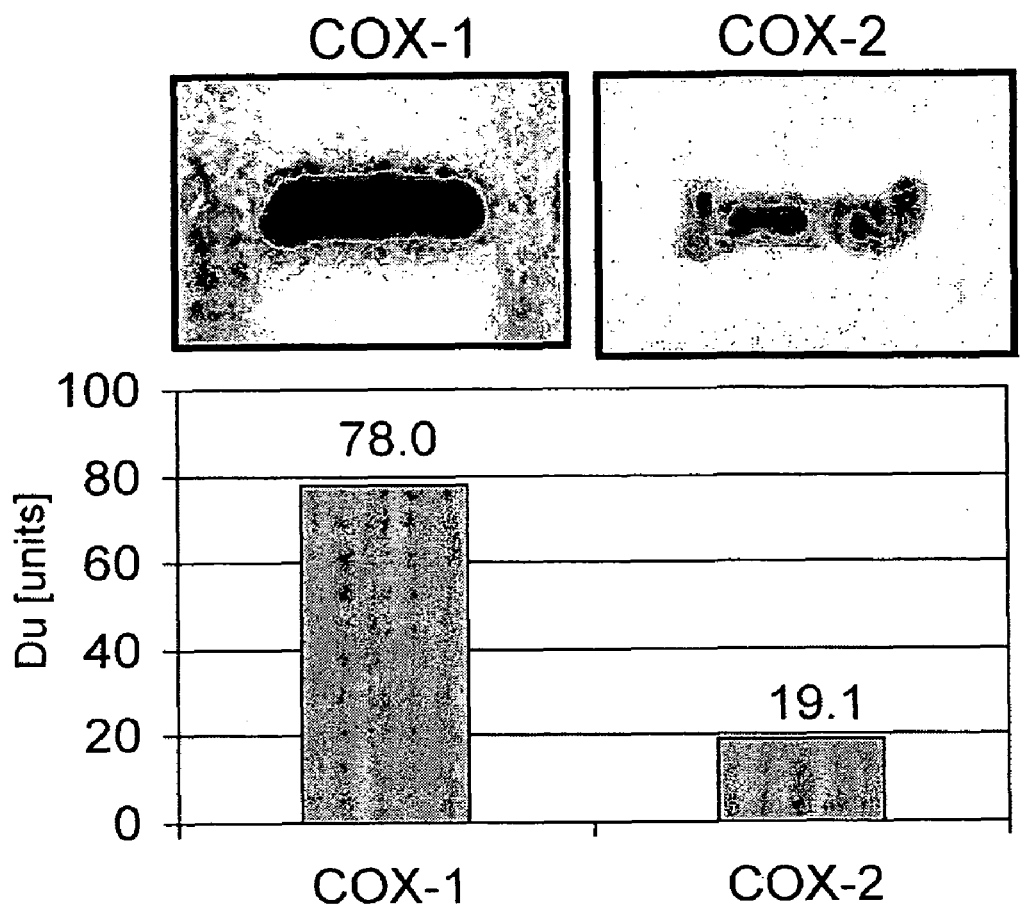
FIG. 4 depicts a representative immunoblots demonstrating constitutive COX-1 and COX-2 expression in AGS human gastric mucosal cells. The AGS human gastric cell line was cultured in 6-well plates at 37° C. with 5% $CO_2$ in a humidified incubator for 24 hours. Cells were lysed on ice in lysis buffer and protein concentration determined. Fifty µg of cell lysate were solubilized, fractionated on a 10% polyacrylamide gel containing sodium dodecylsulfate (SDS), and transferred onto a nitrocellulose membrane. The membranes were incubated in a blocking buffer and then incubated with the respective primary antibody for 1 h at room temperature. Following primary antibody incubation, the blots were washed three times with Tris-buffered saline and then incubated with the secondary antibody for 1 h. Protein bands were visualized using enhanced chemiluminescence.

Results—As seen in FIG. 4, the AGS cell line constitutively expresses both COX-1 and COX-2, with COX-1 expression approximately 4-times greater than COX-2 expression. $PGE_2$ synthesis in AGS cells over 18 h was 660 µg/$10^5$ cells. Thus, this example demonstrates that the AGS human gastric mucosal cell line, possessing constitutive expression of COX-1 and COX-2, can serve as a model for assessing the gastrointestinal toxicity of cyclooxygenase-inhibiting compounds.

In the past, the classical COX-2 hypothesis has downplayed the role of COX-2 expression in the gastrointestinal mucosa. While in normal gastric mucosa COX-1 is the predominant COX isozyme, as demonstrated in this example and in the literature, there is increasing evidence that detectable amount of COX-2 mRNA and protein are both constitutively expressed and inducible in specific locations of the gastric mucosa in both animals and humans (Halter et al. Gut 49:443-453 (2001)). Recent studies in rats have shown that whereas selective inhibition of COX-1 or COX-2 is not ulcerogenic, combined inhibition of both COX-1 and COX-2 induces severe lesions in the stomach and small intestine comparable with the effects of NSAID such as indomethacin. This observation suggests an important contribution of COX-2 to the maintenance of gastrointestinal mucosal integrity.

EXAMPLE 2

Inhibition of $PGE_2$ Synthesis in AGS Gastric Mucosal Cells and A549 Pulmonary Cells by Nonsteroidal Anti-Inflammatory Drugs Summary—This example illustrates that inhibition of $PGE_2$ synthesis in AGS gastric cells and A549 pulmonary cells by NSAIDs correlates with their observed relative clinical gastrictoxicity.

Chemicals—Commercial formulations of rofecoxib tablets and celecoxib capsules were used. $PGE_2$ EIA kits were obtained from Cayman Chemical (Ann Arbor, Mich.). Anti-COX-1 and anti-COX-2 rabbit polyclonal antisera were obtained from Upstate Biotechnology (Waltham, Mass.), and donkey anti-goat IgG-HRP was procured from Santa Cruz Biotechnology (Santa Cruz, Calif.). Heat Inactivated Fetal Bovine Serum (FBS-HI Cat. #35-011CV) and Dulbecco's Modification of Eagle's Medium (DMEM Cat #10-013CV) was purchased from Mediatech (Herndon, Va.). IL-1β and all standard chemicals and non-steroidal anti-inflammatory drugs (NSAIDs), unless noted, were obtained from Sigma (St Louis, Mo.) and were of the highest purity commercially available. All other chemicals were obtained from suppliers as described in EXAMPLE 1.

Cells—A549 (human pulmonary epithelial; ATCC number CCL-185) and AGS cells (human gastric mucosa; ATCC number CRL-1739) were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL, 50 µg streptomycin/mL, 5% sodium pyruvate, and 5% L-glutamine. On the day of the experiments, exponentially growing cells were harvested and washed with serum-free RPMI 1640.

The log phase A549 and AGS cells were plated at $8 \times 10^4$ cells per well in 0.2 mL growth medium per well in a 96-well tissue culture plate. For the determination of $PGE_2$ inhibition by the test compounds in A549 cells, the procedure of Warner et al., also known as the WHMA-COX-2 protocol (Warner et al. Proc. Natl. Acad. Sci. U.S.A. 96, 7563-7568 (1999)) was followed with no modifications. Briefly, 24 hours after plating of the A549 cells, interleukin-1β (10 ng/mL) was added to induce the expression of COX-2. After 24 hr, the cells were washed with serum-free RPMI 1640 and the test materials, dissolved in DMSO and serum-free RPMI, were added to the wells to achieve final concentrations of 25, 5.0, 0.5 and 0.05 µg/mL. Each concentration was run in duplicate. DMSO was added to the control wells in an equal volume to that contained in the test wells. Sixty minutes later, A23187 (50 µM) was added to the wells to release arachidonic acid. Twenty-five µL of media were sampled from the wells 30 minutes later for $PGE_2$ determination.

Non-stimulated AGS cells were used in these studies. Twenty-four hours after plating in the 96-well microtiter plates, the cells were washed with serum-free RPMI 1640 and the test materials, dissolved in DMSO and serum-free RPMI, were added to the wells to achieve final concentrations of 25, 5.0, 0.5 and 0.05 µg/mL. Each concentration was run in duplicate. DMSO was added to the control wells in an equal volume to that contained in the test wells. Sixty minutes later, the calcium ionophore A23187 was added to the wells to achieve a final concentration of 50 µM. Twenty-five 1L of media were sampled from the wells 30 minutes after the addition of A23187 for $PGE_2$ determination.

Cell viability—Cell viability was assessed by a 3-(4,5-dimethylthiazol-2-yl)-2,5-diphenyltetrazolium bromide (MTT)-based colorimetric assay (Sigma, St. Louis, Mo.). The MTT solution was added directly to the wells after sampling for $PGE_2$ determination. The absorbance of each well was read at 580 nm using an ELISA plate reader. No toxicity was observed at the highest concentrations tested for any of the compounds.

$PGE_2$ Assay—A commercial, non-radioactive procedure for quantification of $PGE_2$ was employed (Cayman Chemical, Ann Arbor, Mich.) for the determination of $PGE_2$ and the recommended procedure of the manufacturer was used without modification. Briefly, 50 µL of the supernatant culture medium, along with a serial dilution of $PGE_2$ standard samples, were mixed with appropriate amounts of acetylcholinesterase-labeled tracer and $PGE_2$ antiserum and incubated at room temperature for 18 h. Afterwards, the wells in the PGE$_2$-assay microtiter plate were emptied and rinsed with wash buffer, 200 μL of Ellman's reagent containing substrate for acetylcholinesterase were then added. The reaction was performed on a slow shaker at room temperature for 1 h, after which absorbance at 415 nm was determined in a Bio-Tek Instrument ELISA plate reader (Model #Elx800, Winooski, Vt.). The manufacturer's specifications for this assay include an intra-assay coefficient of variation of <10%, cross reactivity with PGD$_2$ and PGF$_{2\alpha}$ of less than 1%, and linearity over the range of 10-1000 pg/mL. The PGE$_2$ concentration was recorded as pg PGE$_2$ per $10^5$ cells.

Calculations—The median inhibitory concentration (IC$_{50}$) for PGE$_2$ synthesis was calculated using CalcuSyn (BIO-SOFT, Ferguson, Mo.). This statistical package performs multiple drug dose-effect calculations using the median effect methods described by Chou and Talaly, *Adv. Enzyme Regul.* 22:27-55. (1984), hereby incorporated by reference.

Briefly, the analysis correlates the "Dose" and the "Effect" in the simplest possible form: $fa/fu = (C/C_m)^m$, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve. It is estimated by the slope of the median-effect plot.

The median-effect plot is a graph of x=log(C) vs y=log(fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r>0.96, from tissue culture an r>0.90 and from animal systems an r>0.85. In the cell-based studies reported here, all linear correlation coefficients were greater than 0.90. Experiments were repeated three times on three different dates. The percent inhibition at each dose was averaged over the three independent experiments and used to calculate the median inhibitory concentrations reported. The therapeutic index (TI) for gastrointestinal safety was computed as the ratio AGS$_{(IC50)}$/A549$_{(IC50)}$. Spearman's rank correlation coefficient $r_s$ was computed to quantify the degree of association between in vitro ranking of TI by the AGS model and ranking of clinically assessed NSAID gastropathy. The probability of a type I error was set at the nominal five percent level.

Results—The highly specific COX-2 inhibitor diisofluorophosphate (DIFP) exhibited a median inhibitory concentration in A549 cells of 6.5 μg/mL and marginally inhibited PGE$_2$ synthesis in AGS cells at the highest concentration tested of 25 μg/mL. Extrapolation of the dose-response curve provided an estimate of the AGS IC$_{50}$ for DIFP of 359 μg/mL (Table 3). Of the three COX-2 selective agents, rofecoxib was the only compound to demonstrate target cell selectivity greater than unity (AGS IC$_{50}$/A549 IC$_{50}$>1). Celecoxib and nimensulide, both of which demonstrate high COX-2 selectivity in enzyme assays, surprisingly exhibited greater PGE$_2$ inhibition in the AGS gastric cells than in the A549 target cells.

Figure 5:
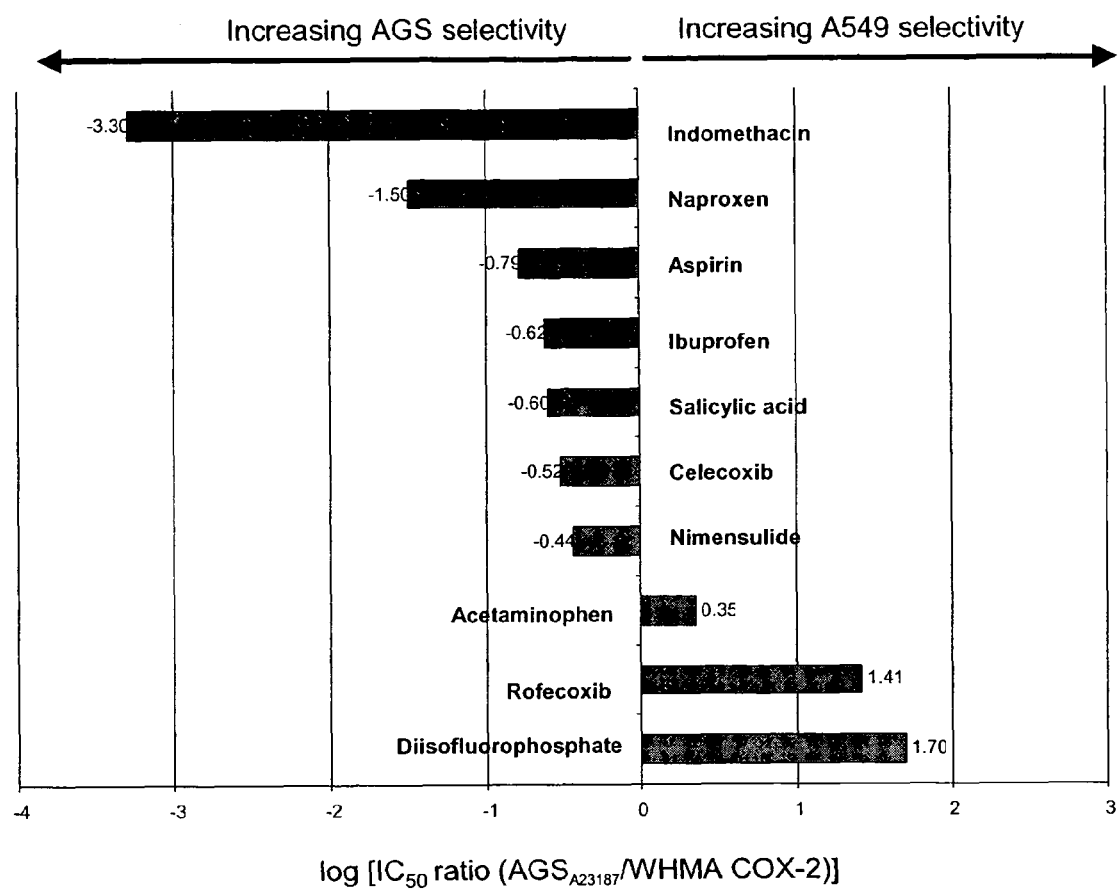
FIG. 5 depicts a comparison of Log $IC_{50}$ ratios (AGS/WHMA COX-2). Values to the right of 0 indicate decreasing probability of gastrointestinal effects, while values to the left of 0 indicate increasing probability of gastrointestinal effects.

Consistent with demonstrated clinical gastric toxicity, ibuprofen, aspirin and indomethacin all inhibited PGE$_2$ synthesis in the AGS cell line to a greater extent than in the target A549 cells. Salicylic acid and acetaminophen were relatively inactive in both cell models. FIG. 5 compares and ranks the log TI computed for the NSAIDs. Values to the right of 0 indicate decreasing probability of gastrointestinal effects, while values to the left of 0 indicate increasing probability of gastrointestinal effects. The AGS gastric cell model provided rank estimates of GI toxicity significantly associated with clinical rankings of NSAID gastropathy, respectively $r_s$=0.933, p<0.01; 0.783, p<0.01; 0.683, p=0.05. The ranking of NSAIDs from lowest to greatest potential for GI toxicity was
rofecoxib<acetaminophen<nimensulide<celecoxib<salicylic acid<ibuprofen<aspirin<naproxen<indomethacin.

These results validate the use of the AGS gastric mucosal cell line to evaluate potential gastrointestinal toxicity of anti-inflammatory agents capable of inhibiting the synthesis of PGE$_2$. They also demonstrate cellular specificity in the action of COX-inhibiting compounds. A ratio of 1 for IC$_{50}$ AGS/IC$_{50}$ A549 indicates IC$_{50}$'s that are the same for both the AGS cell and A549 cells. If the ratio is higher than 1 for IC$_{50}$ AGS/IC$_{50}$ A549, then the inhibition of PGE$_2$ is lower for the AGS cells. A lower inhibition of PGE$_2$ in AGS cells is favorable because AGS cell line expresses more COX-1, which maintains mucosal homeostasis.

TABLE 3

Median inhibitory concentrations for PGE$_2$ synthesis of select NSAID in the A549 (target) and AGS (nontarget) cell models†.

| Compounds | IC50 A549 [μM] | IC50 AGS [μM] | AGS/A549 |
|---|---|---|---|
| DIFP†† | 6.5 (1.5-28) | 359 (125-1022) | 55 |
| Rofecoxib | 0.24 (0.15-0.45) | 5.5 (2.7-11) | 23 |
| Celecoxib | 0.21 (0.01-4.2) | 0.063 (0.02-0.22) | 0.30 |
| Nimensulide | 0.32 (0.16-0.65) | 0.12 (0.0081-1.7) | 0.38 |
| Naproxen | 28 (1.3-600) | 0.83 (0.24-2.8) | 0.03 |
| Ibuprofen | 12 (6.8-19) | 2.8 (1.3-5.8) | 0.23 |
| Aspirin | 18 (3.0-106) | 2.9 (1.4-5.6) | 0.16 |
| Salicylic acid | 4246 (355-50971) | 1065 (94-12217) | 0.25 |
| Acetaminophen | 238 (6.62-9589) | 535 (179-1616) | 2.3 |
| Indomethacin | 8.1 (2.6-26) | 0.0042 (0.00042-0.039) | 0.00052 |

†Parenthetic values are 95% confidence intervals of the IC$_{50}$ estimate.
††DIFP = diisofluorophosphate.

EXAMPLE 3

Inhibition of PGE$_2$ Synthesis in Stimulated and Nonstimulated Murine Macrophages by HOPS (*Humulus lupulus*) Compounds and Derviatives Summary—This example illustrates that hops fractions and derivatives inhibit COX-2 synthesis of PGE$_2$ preferentially over COX-1 synthesis of PGE$_2$ in the RAW 264.7 murine macrophage model.

Chemicals and reagents—Bacterial lipopolysaccharide (LPS; B *E. coli* 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available. All other chemicals and equipment were as described in EXAMPLES 1 and 2.

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8 \times 10^4$ cells per well in 0.2 mL growth medium per well in a 96-well tissue culture plate in the morning. At the end of the day one (6 to 8 h post plating), 100 µL of growth medium from each well were removed and replaced with 100 µL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000× stock in DMSO. In 1.7 mL microfuge tubes, 1 mL DMEM without FBS was added for test concentrations of 0.05, 0.10, 0.5, and 1.0 µg/mL. Two µL of the 1000× DMSO stock of the test material was added to the 1 mL of medium without FBS. The tube contained the final concentration of the test material concentrated 2-fold and was placed in an incubator for 10 minutes to equilibrate to 37° C.

For COX-2 associated $PGE_2$ synthesis, 100 µL of medium were removed from each well of the cell plates prepared on day one and replaced with 100 µL of equilibrated 2× final concentration of the test compounds. Cells were then incubated for 90 minutes. Twenty µL of LPS were added to each well of cells to be stimulated to achieve a final concentration of 10 ng LPS/mL and the cells were incubated for 4 h. Following the LPS stimulation, the appearance of the cells was observed and viability was determined as described in EXAMPLE 2. No toxicity was observed at the highest concentrations tested for any of the compounds. Twenty-five µL of supernatant medium from each well was transferred to a clean microfuge tube for the determination of $PGE_2$ released into the medium. $PGE_2$ was assayed and reported as previously described in EXAMPLE 1.

For COX-1 associated $PGE_2$ synthesis, 100 µL of medium were removed from each well of the cell plates prepared on day one and replaced with 100 µL of equilibrated 2× final concentration of the test compounds. Cells were then incubated for 90 minutes. Next, instead of LPS stimulation, the cells were incubated with 100 µM arachidonic acid for 15 minutes. Twenty-five µL of supernatant medium from each well was transferred to a clean microfuge tube for the determination of $PGE_2$ released into the medium. The appearance of the cells was observed and viability was determined as described in EXAMPLE 2. No toxicity was observed at the highest concentrations tested for any of the compounds. Twenty-five µL of supernatant medium from each well was transferred to a clean microfuge tube for the determination of $PGE_2$ released into the medium. $PGE_2$ was determined and reported as previously described in EXAMPLE 1. The median inhibitory concentrations ($IC_{50}$) for $PGE_2$ synthesis from both COX-2 and COX-1 were calculated as described in EXAMPLE 2.

TABLE 4

COX-2 and COX-1 inhibition in RAW 264.7 cells by hop fractions and derviatives

| Test Material | COX-2 $IC_{50}$ [µg/mL] | COX-1 $IC_{50}$ [µg/mL] | COX-1 $IC_{50}$/COX-2 $IC_{50}$ |
|---|---|---|---|
| Genus A structures | | | |
| Isohop (IAA) | 0.13 | 18 | 144 |
| Redihop (RIAA) | 0.34 | 29 | 87 |
| Genus B structures | | | |
| Tetrahop (THIAA) | 0.20 | 4.0 | 21 |
| Hexahop (HHIAA) | 0.29 | 3.0 | 11 |
| Alpha acids | | | |
| Alpha hop (AA) | 0.21 | 6.2 | 30 |
| Others | | | |
| Aromahop OE | 1.6 | 4.1 | 2.6 |
| Beta acids (BA) | 0.54 | 29 | 54 |
| Spent hops (EtOH) | 0.88 | 21 | 24 |

As seen in Table 4, all hops fractions and derivatives selectively inhibited COX-2 over COX-1 in this target macrophage model. This was a novel and unexpected finding. The extent of COX-2 selectivity for the hops derivatives IAA and RIAA, respectively, 144- and 87-fold, was unanticipated. In this RAW 264.7 cell model, Genus A compounds exhibited a greater COX-2 selectivity than Genus B compounds, averaging 116-fold vs 16-fold, respectively, greater COX-2 inhibition. Alpha acid, beta acids and spent hops were also highly selective COX-2 inhibitors with COX-1/COX-2 ratios, respectively, 30, 54 and 24. Such high COX-2 selectivity combined with low median inhibitory concentrations, has not been previously reported for natural products from other sources. Aromahop was least COX-2 selective with a COX-1/COX-2 ratio of 2.6, similar to acetaminophen (EXAMPLE 2) a NSAID with demonstrated low clinical gastrotoxicity.

EXAMPLE 4

Lack of Inhibition of $PGE_2$ Synthesis in Gastric Mucosal Cells by HOPS (*Humulus lupulus*) Compounds and Derviatives Summary—This example illustrates the lack of $PGE_2$ inhibition by hops fractions and in the AGS human gastric mucosal cell line implying low gastric irritancy potential of these compounds.

Chemicals and reagents were used as described in EXAMPLE 3. AGS cells were grown and used for testing hops compounds and derivatives as described in EXAMPLE 2. $PGE_2$ was determined and reported as previously described in EXAMPLE 1. The median inhibitory concentrations ($IC_{50}$) for $PGE_2$ synthesis from AGS cells were calculated as described in EXAMPLE 2.

TABLE 5

Median inhibitory concentrations (IC$_{50}$) for PGE$_2$ synthesis of hops derivatives in the AGS cell model†

| Compound | AGS IC$_{50}$ [μg/mL] | 95% Confidence Interval [μg/mL] | r |
|---|---|---|---|
| Alpha Acids | | | |
| Alphahop | 17 | 2.4-124 | 0.927 |
| Genus A structures†† | | | |
| Iso-alpha acids | | | |
| Isohop (IAA) | 16 | 4.9-54 | 0.970 |
| Isorich | 9.2 | 1.1-81 | 0.894 |
| Reduced iso-alpha acids | | | |
| Redihop (RIAA) | 21 | 3.1-145 | 0.936 |
| Genus B structures††† | | | |
| Tetra-iso-alpha acids | | | |
| Tetrahop (THIAA) | 51 | 6.8-374 | 0.949 |
| Hexa-iso-alpha acids | | | |
| Hexahop (HHIAA) | 34 | 25-47 | 0.998 |
| Others | | | |
| BetaStab | 73 | 18-291 | 0.977 |
| Tannin extract #4411 | 59 | 11-324 | 0.963 |
| Aromahop | 43 | 21-85 | 0.992 |
| #1115 (Spent hops) | 35 | 8.5-141 | 0.970 |
| Positive Concurrent Control | | | |
| Aspirin | 1.2 | (0.37-4.1) | 0.950 |
| Historical Control | | | |
| Aspirin | 0.52 | (0.26-1.0) | — |
| Ibuprofen | 0.57 | (0.27-1.2) | — |
| Rofecoxib | 1.8 | (0.90-3.7) | — |
| Celcoxib | 0.024 | (0.0068-0.082) | — |

†IC$_{50}$ values are computed from the average of three independent assays; AGS cells were plated and allowed to reach 80% confluence. Cells were washed and test material was added 60 minutes prior to treatment with A23187. Thirty minutes later, media was removed for PGE2 determination.

Median inhibitory concentrations for PGE$_2$ synthesis of hops derivatives in the AGS cell model are presented in Table 3. Genus B structures, in general, were less inhibitory than Genus A structures and alpha acids. In the Genus B group, IC$_{50}$ values for THIAA and HHIAA were, respectively, 51 and 34 μg/mL. IC$_{50}$ values for IAA, Isorich and RIAA from the Genus A group were, respectively, 16, 9.2 and 21 μg/mL, on average 63% lower than IC$_{50}$ values from Genus B species. With relatively high IC$_{50}$ values, hops derivatives BetaStab (73 μg/mL), Tannin extract #4411 (59 μg/mL), Aromahop (43 μg/mL) and #1115 spent hops (35 μg/mL) would rank as non-irritating to the gastric mucosa. Unexpectedly, all hops derivatives were substantially less inhibitory to AGS gastric mucosal cells than any NSAID including the newer, highly selective COX-2 drugs rofecoxib and celecoxib.

EXAMPLE 5

Combinations of Genus A HOPS Derivatives and Ibuprofen or Aspirin Exhibit Decreased Inhibition of PGE$_2$ Synthesis in AGS Gastric Mucosal Cells Summary—This example illustrates an antagonistic effect of Genus A hops species on the inhibition of gastric PGE$_2$ by the NSAIDs ibuprofen and aspirin. The implication of this effect is that Genus A hops derivatives function to attenuate the gastropathy of NSAIDs.

Methods—Chemicals and reagents were used as described in EXAMPLES 2 and 3. AGS cells were grown and used for testing the Genus A hops derivative RIAA and combinations of RIAA:ibuprofen and RIAA:aspirin as described in EXAMPLE 2. RIAA:NSAID combinations were formulated to contain either 1, 9, 50, 91, or 99 percent RIAA. Concentrations of test material of 50, 5, 0.5 and 0.05 μg/mL were assayed in duplicate. PGE$_2$ was determined and reported as previously described in EXAMPLE 1. The median inhibitory concentrations (IC$_{50}$) for PGE$_2$ synthesis from AGS cells were calculated as described in EXAMPLE 2.

Synergy or antagonism of test formulations was quantified using the combination index (CI) parameter and CalcuSyn (BIOSOFT, Ferguson, Mo.) software. The CI of Chou-Talaly is based on the multiple drug-effect and is derived from enzyme kinetic models (Chou and Talalay, *Adv. Enzyme Regul.* 22:27-55 (1984)). The equation determines only the additive effect rather than synergism or antagonism. However, synergism, as used herein, is defined as a more than expected additive effect, and antagonism as a less than expected additive effect as proposed by Cho and Talalay Using the designation of CI=1 as the additive effect, for mutually exclusive compounds that have the same mode of action or for mutually non-exclusive drugs that have totally independent modes of action, the following relationships were obtained: CI<1, =1, and >1 indicating synergism, additivity and antagonism, respectively.

Results—FIG. 6A and FIG. 6B depict the percent PGE$_2$ inhibition in the AGS gastric mucosal cell, respectively, for ibuprofen, RIAA and combinations of RIAA:ibuprofen (FIG. 6A), and aspirin, RIAA and combinations of RIAA:aspirin (FIG. 6B). Unexpectedly, as little as one percent RIAA in combination with ibuprofen or aspirin reduces the PGE$_2$ inhibitory effect of either NSAID. Computation of the CI for RIAA and ibuprofen or aspirin indicates extremely strong synergy over the entire dose-response curve for RIAA:NSAID combinations of 100:1 to 1:10 (Table 6). With RIAA:NSAID combinations of 100:1, inhibition of PGE$_2$ biosynthesis was insufficient to compute a dose-response.

TABLE 6

Combination index† values for RIAA:ibuprofen and RIAA:aspirin combinations in the AGS gastric mucosal cell model

| Test Material | CI IC$_{50}$ | CI IC$_{75}$ | CI IC$_{90}$ | Average CI |
|---|---|---|---|---|
| Ibuprofen Combinations | | | | |
| RIAA:ibuprofen (1:100) | 170 | 16 | 1.5 | 63 |
| RIAA:ibuprofen (1:10) | 164 | 12 | 1.1 | 59 |
| RIAA:ibuprofen (1:1) | 210 | 60 | 43 | 104 |
| RIAA:ibuprofen (10:1) | 28 | 5.9 | 3.4 | 12 |
| RIAA:ibuprofen (100:1) | NDR†† | | | |
| Aspirin Combinations | | | | |
| RIAA:aspirin (1:100) | 24164 | 54835 | $4.0 \times 10^5$ | $1.3 \times 10^5$ |
| RIAA:aspirin (1:10) | 254 | 2.7 | 0.5 | 85 |
| RIAA:aspirin (1:1) | 697 | 1597 | 76808 | 26367 |
| RIAA:aspirin (10:1) | 455 | 128 | 170 | 251 |
| RIAA:aspirin (100:1) | | | NDR | |

†CI <1, =1, and >1 indicate synergism, additivity and antagonism, respectively.

††NDR = no dose-response to 50 μg test material/mL over doses of 50, 5, 0.5 and 0.05 μg test material/mL.

Similar experiments are performed with various fractions isolated or derived from hops and various non-steroidal anti-inflammatory compounds such as NSAIDs.

EXAMPLE 6

Combinations of Genus B HOPS Derivatives and Ibuprofen or Aspirin Exhibit Decreased Inhibition of $PGE_2$ Synthesis in AGS Gastric Mucosal Cells Summary—This example illustrates an antagonistic effect of Genus B hops species on the inhibition of gastric $PGE_2$ by the NSAIDs ibuprofen and aspirin. The implication of this effect is that Genus B hops derivatives function to attenuate the gastropathy of NSAIDs.

Methods—Chemicals, reagents and methods were as described in EXAMPLES 2, 3 AND 5. AGS cells were grown and used for testing the Genus B hops derivative THIAA and combinations of THIAA:ibuprofen and THIAA:aspirin as described in EXAMPLE 2. THIAA:NSAID combinations were formulated to contain either 1, 9, 50, 91, or 99 percent THIAA. Concentrations of test material of 50, 5, 0.5 and 0.05 μg/mL were assayed in duplicate. $PGE_2$ was determined and reported as previously described in EXAMPLE 1. The median inhibitory concentrations ($IC_{50}$) for $PGE_2$ synthesis from AGS cells were calculated as described in EXAMPLE 2. Synergy or antagonism of test formulations was quantified using the combination index (CI) parameter as described in EXAMPLE 5.

Results—FIGS. 7A and 7B depict the percent $PGE_2$ inhibition in the AGS gastric mucosal cell, respectively, for ibuprofen, THIAA and combinations of THIAA:ibuprofen (FIG. 7A), and aspirin, RIAA and combinations of RIAA:aspirin (FIG. 7B). THIAA combinations with ibuprofen were qualitatively similar to RIAA combinations with ibuprofen with respect to the attenuation of $PGE_2$ inhibition by the NSAID. CI for THIAA:ibuprofen combinations, however, indicated antagonism only at the portions of the dose-response curve below 50 percent inhibition. Graphically as seen in FIG. 7B, the THIAA:aspirin combinations appear to increase $PGE_2$ inhibition in AGS gastric mucosal cells at both the 5 and 0.5 test material concentrations. Computation of CI revealed that THIAA:aspirin combinations were antagonistic at the low end of the dose-response curve where inhibition of $PGE_2$ was less than 40 percent. Above the 40 percent level, strong synergy was seen with THIAA and aspirin combinations.

TABLE 7

Combination index† values for THIAA:ibuprofen and THIAA:aspirin combinations in the AGS gastric mucosal cell model

| Test Material | CI $IC_{50}$ | CI $IC_{75}$ | CI $IC_{90}$ | Average CI |
|---|---|---|---|---|
| Ibuprofen Combinations | | | | |
| THIAA:ibuprofen (1:100)[a] | 2.5 | 0.30 | 0.037 | 1.1 |
| THIAA:ibuprofen (1:10)[b] | 18 | 0.86 | 0.040 | 6.3 |
| THIAA:ibuprofen (1:1)[c] | 4.0 | 0.48 | 0.058 | 1.5 |
| THIAA:ibuprofen (10:1)[d] | 1.1 | 0.083 | 0.0065 | 0.40 |
| THIAA:ibuprofen (100:1)[d] | 1.3 | 0.067 | 0.0038 | 0.46 |
| Aspirin Combinations | | | | |
| THIAA:aspirin (1:100)[e] | 0.27 | 0.0033 | $4.1 \times 10^{-5}$ | $1 \times 10^{-5}$ |
| THIAA:aspirin (1:10)[f] | 0.16 | 0.0018 | $2.5 \times 10^{-5}$ | $1 \times 10^{-5}$ |
| THIAA:aspirin (1:1)[a] | 7.96 | 0.08 | 0.0020 | |

TABLE 7-continued

Combination index† values for THIAA:ibuprofen and THIAA:aspirin combinations in the AGS gastric mucosal cell model

| Test Material | CI $IC_{50}$ | CI $IC_{75}$ | CI $IC_{90}$ | Average CI |
|---|---|---|---|---|
| THIAA:aspirin (10:1)[e] | 0.24 | 0.0078 | 0.0011 | |
| THIAA:aspirin (100:1)[f] | 0.20 | 0.0086 | 0.00065 | |

†CI < 1, = 1, and > 1 indicate synergism, additivity and antagonism, respectively.
††NDR = no dose-response to 50 μg test material/mL over doses of 50, 5, 0.5 and 0.05 μg test material/mL.
[a]Antagonism to $IC_{60}$;
[b]Antagonism to $IC_{70}$;
[c]Antagonism to $IC_{65}$;
[d]Antagonism to $IC_{50}$.
[e]Antagonism to $IC_{40}$;
[f]Antagonism to $IC_{35}$.

Similar experiments are performed with various fractions isolated or derived from hops and various non-steroidal anti-inflammatory compounds such as NSAIDs.

EXAMPLE 7

Combinations of Genus A HOPS Derivatives and Ibuprofen or Aspirin Exhibit Increased Therapeutic Indicies Summary—This example illustrates that combinations of Genus A representative species RIAA increases the therapeutic index of both ibuprofen and aspirin.

Methods—Chemicals and reagents were used as described in EXAMPLES 2 and 3. RAW 264.7 and AGS cells were grown and used for testing the Genus A hops derivative RIAA and combinations of RIAA:ibuprofen and RIAA:aspirin as described in EXAMPLE 2 and 3. RIAA:NSAID combinations were formulated to contain either 50 percent RIAA. Concentrations of test material of 50, 5, 0.5 and 0.05 μg/mL were assayed in duplicate. $PGE_2$ was determined and reported as previously described in EXAMPLE 1. Plots of log $IC_{50}$ ratios (AGS/COX-2) were made as described in EXAMPLE 2.

Figure 8:
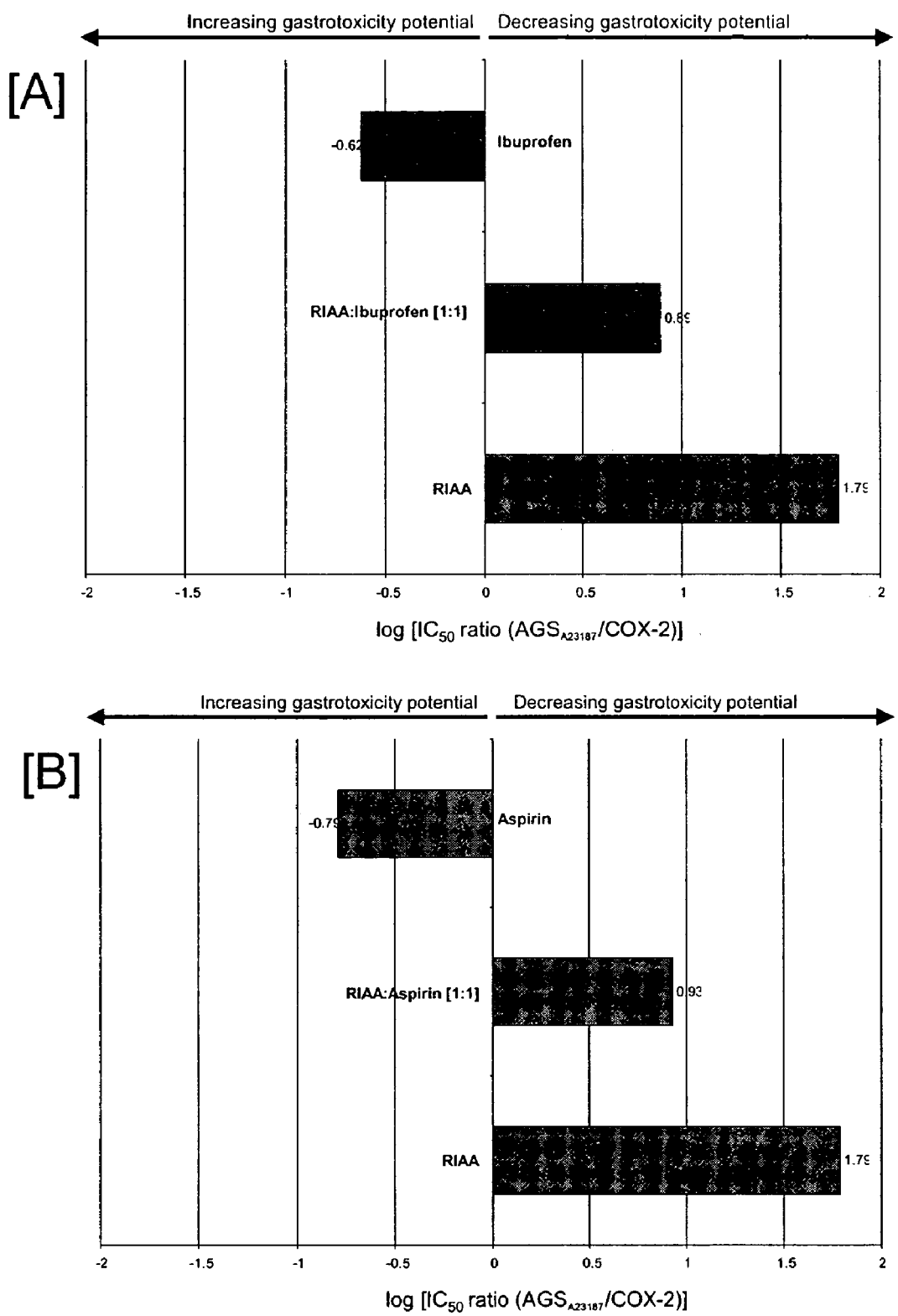
FIG. 8 depicts a comparison of Log $IC_{50}$ ratios (AGS/COX-2).

Results—As seen in FIG. 8, with increasing RIAA in the test formulation, the potential for inducing gastrotoxicity was decreased for both ibuprofen FIG. 8A and aspirin FIG. 8B.

Similar experiments are performed with various fractions isolated or derived from hops and various non-steroidal anti-inflammatory compounds such as NSAIDs.

EXAMPLE 8

Combinations of Genus A HOPS Derivatives and Ibuprofen or Aspirin Exhibit Increased Therapeutic Indicies Summary—This example illustrates that combinations of Genus B representative species THIAA increases the therapeutic index of both ibuprofen and aspirin. Thus, although THIAA species of hops derivatives were antagonistic only at portions of the dose-response curve below 40 percent, the overall effect was to increase the efficacy of NSAIDs in target cells to a greater extent resulting in an unexpectedly large, positive increase in the therapeutic index of NSAIDs.

Methods—Chemicals and reagents were used as described in EXAMPLES 2 and 3. RAW 264.7 and AGS cells were grown and used for testing the Genus B hops derivative THIAA and combinations of THIAA:ibuprofen and THIAA:aspirin as described in EXAMPLE 2 and 3. THIAA:NSAID combinations were formulated to contain either 1 or 50 percent THIAA. Concentrations of test material of 50, 5, 0.5 and 0.05 μg/mL were assayed in duplicate. $PGE_2$ was determined and reported as previously described in EXAMPLE 1. Plots of log $IC_{50}$ ratios (AGS/COX-2) were made as described in EXAMPLE 2.

Figure 9:
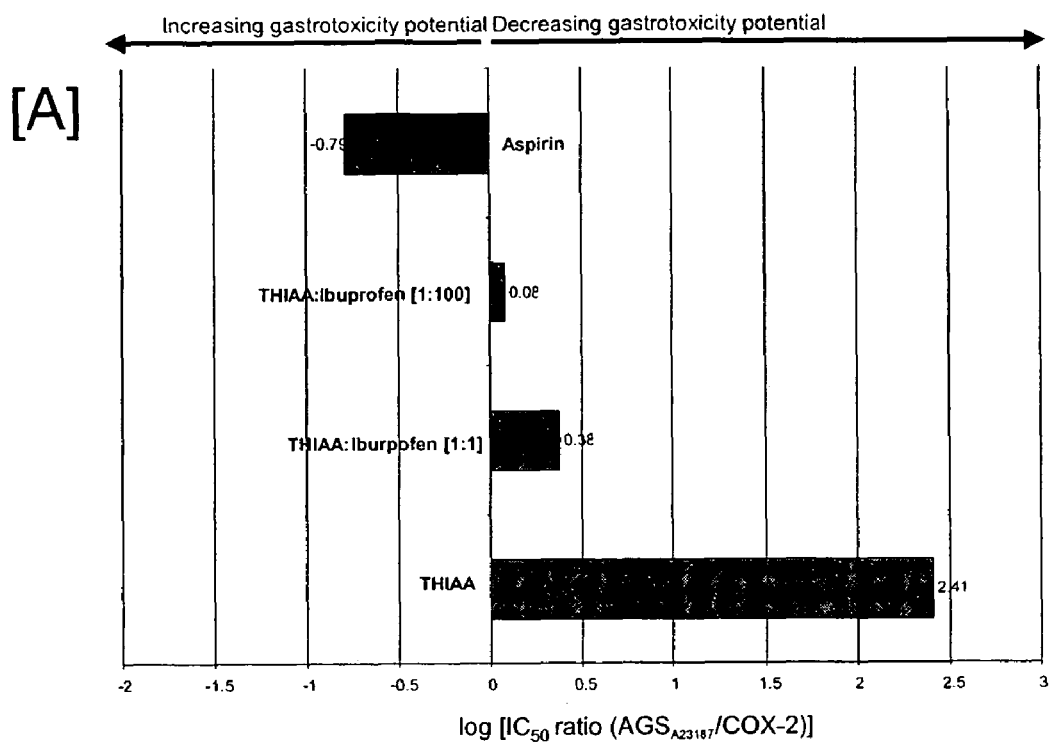
FIG. 9 depicts a comparison of Log $IC_{50}$ ratios (AGS/COX-2).
Figure 9:
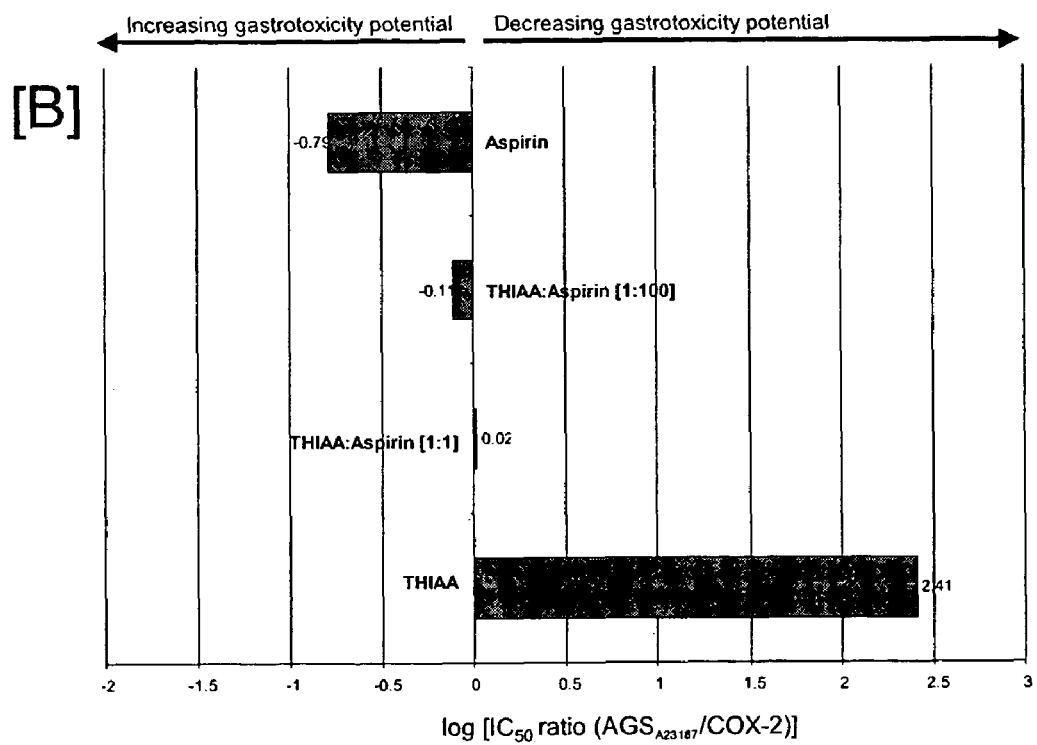
Figure 10:
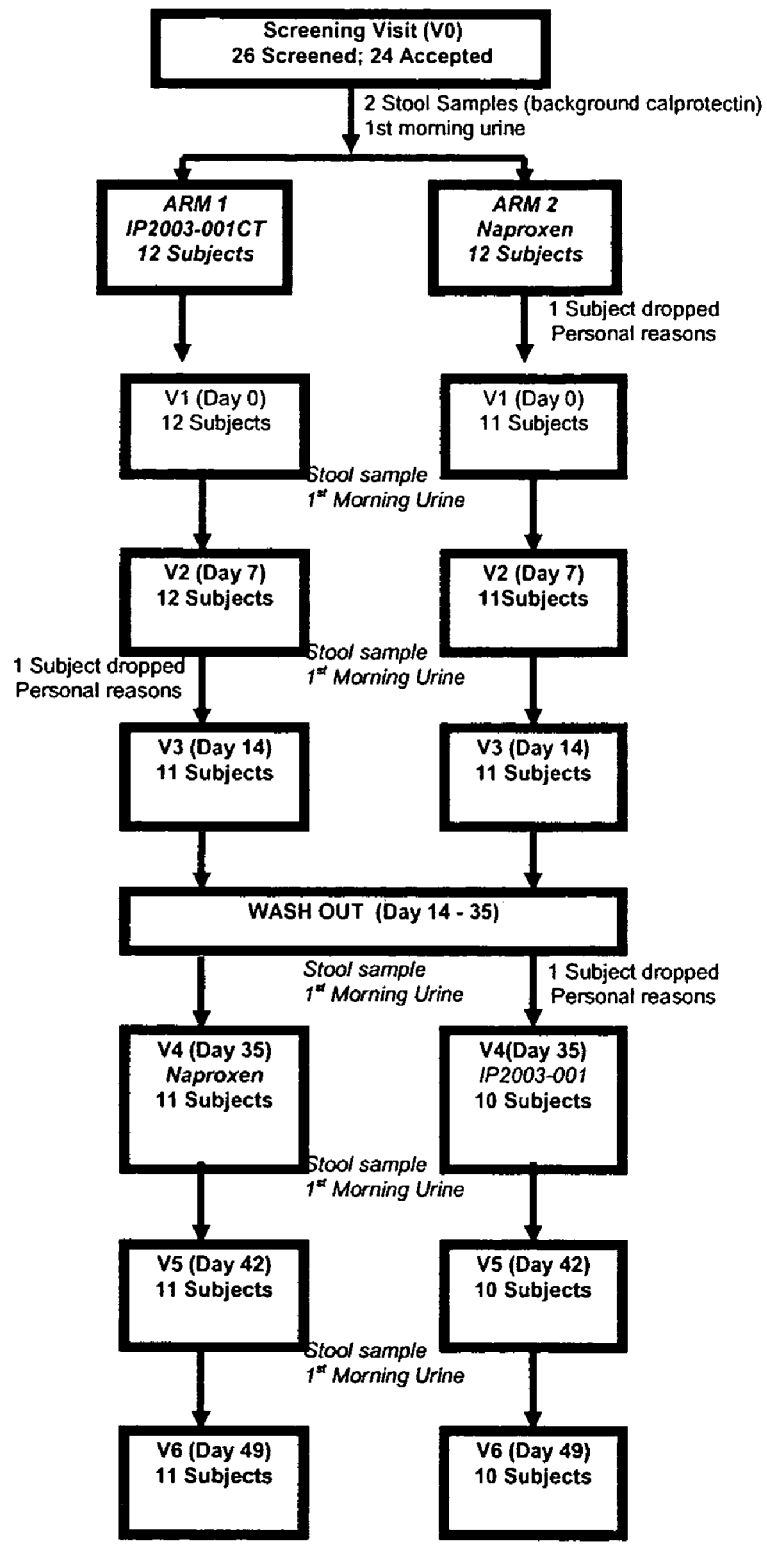
FIG. 10 shows a schematic of clinical trial comparing a composition comprising hops extract and anti-inflammatory medications. Twenty-six subjects were screened, 23 subjects entered the trial, and 21 subjects completed the trial. Of those who did not complete the trial, 3 withdrew for personal reasons, 2 from ARM 2 and 1 from ARM 1. Visits occurred as follows: visit 1 (V1), day 0 of treatment A; V2, 7±1 days of treatment A; V3, 14±1 days of treatment A; Washout, 21±1 days; V4, day 0 of treatment B; V5, 7±1 days of treatment B; V6, 14±1 days after treatment B.
Figure 11:
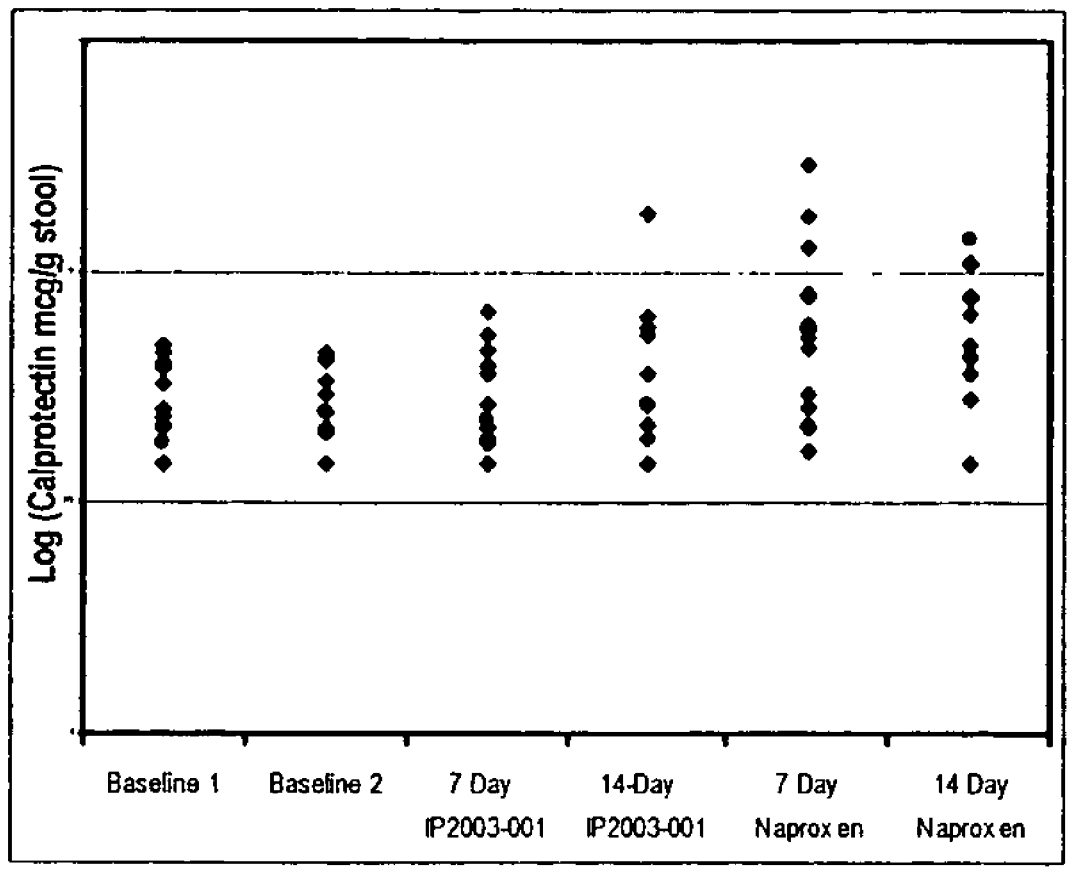
FIG. 11 shows individual calprotectin levels for the subjects who completed the clinical trial (N=21). Baseline 1 is the average V1 value and Baseline 2 is the value after the 21-day wash-out. The 7 day and 14 day data for IP2003-001CT and naproxen are shown. (Reference range<50 µg/g stool).
Figure 12:
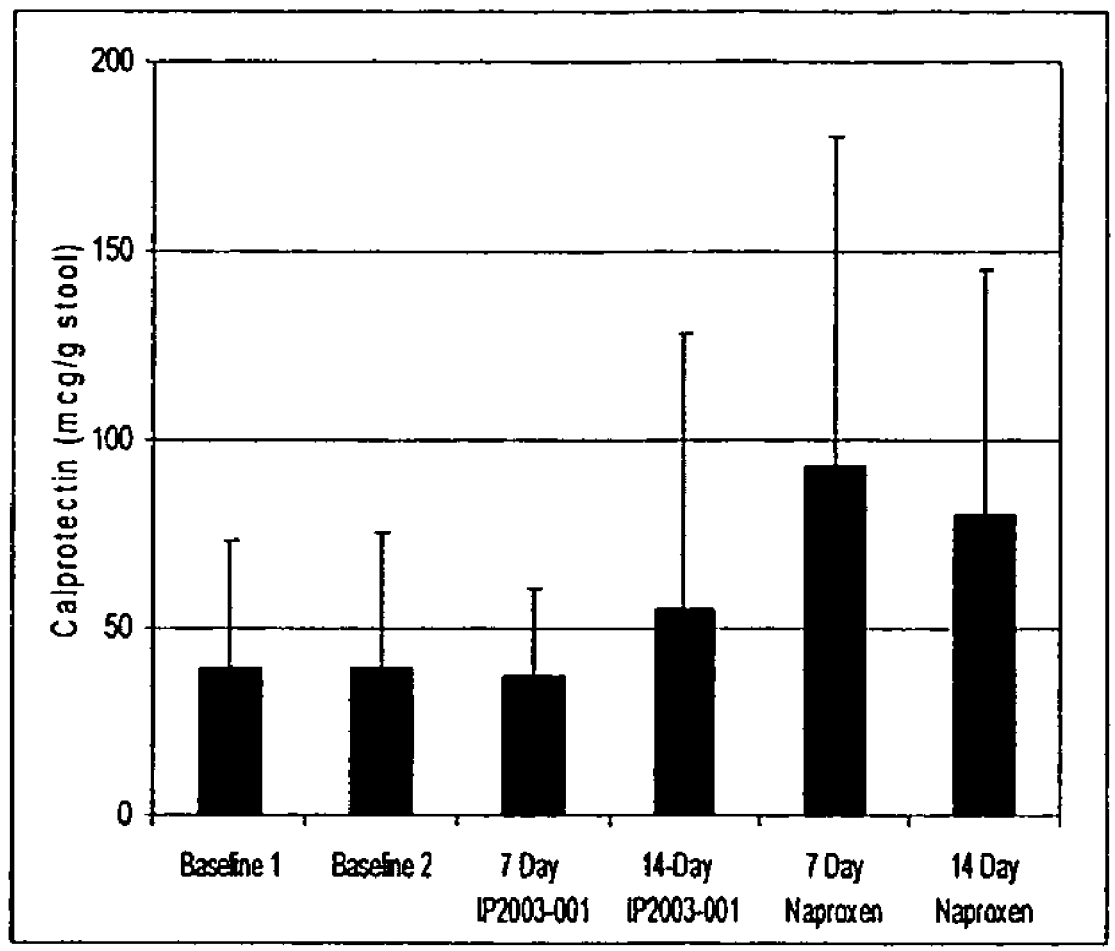
FIG. 12 shows the pooled mean (±sd) calprotectin for the subjects who completed the clinical trial (N=21). Baseline 1 is the average V1 value and Baseline 2 is the value after the 21-day wash-out. No significant difference was seen between Baseline 1 and Baseline 2. No significant difference was seen between Baseline 1 and either 7-day or 14-day IP2003-001CT treatment as well. However, both 7-day and 14-day naproxen values were significantly elevated from Baseline 1 ($p<0.05$). (Reference range<50 µg/g stool).
Figure 13:
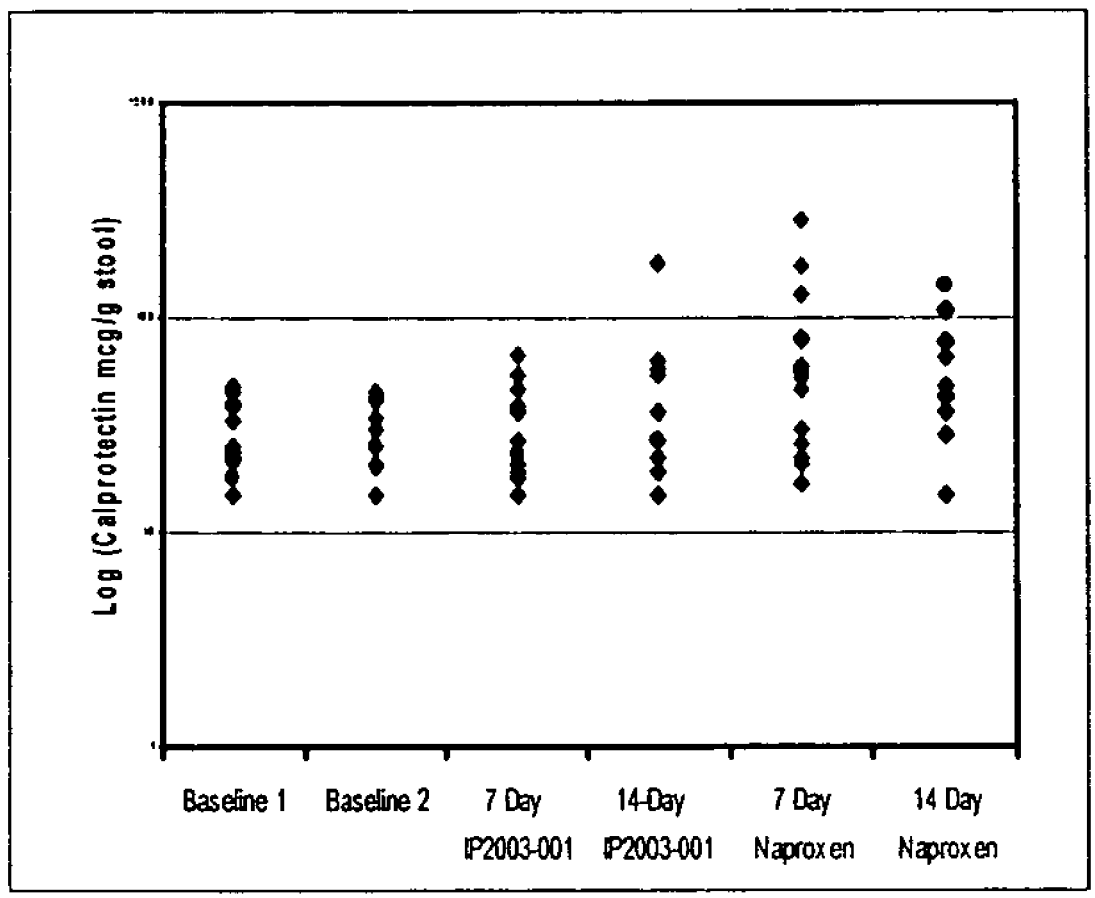
FIG. 13 shows individual calprotectin for the subjects who had baseline values within the reference range of <50 µg/g stool (N=15). Baseline 1 is the average V1 value and Baseline 2 is the value after the 21-day wash-out. The 7 day and 14 day data for IP2003-001CT and naproxen are also shown.
Figure 14:
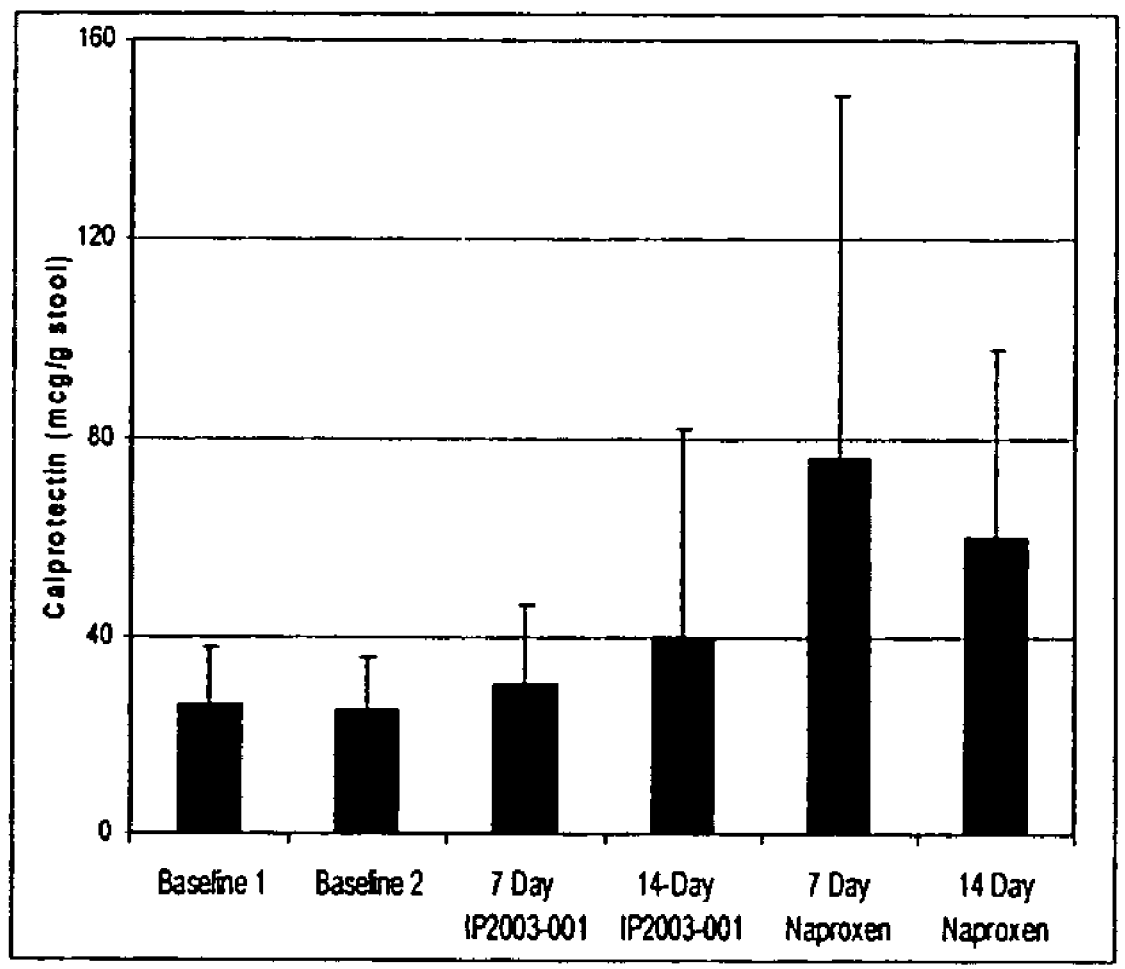
FIG. 14 shows mean (±sd) calprotectin levels for the subjects who had baseline values within the reference range of <50 µg/g stool (N=15). Baseline 1 is the average V1 value and Baseline 2 is the value after the 21-day wash-out. The 7 day and 14 day data for IP2003-001CT and naproxen are also shown.
Figure 15:
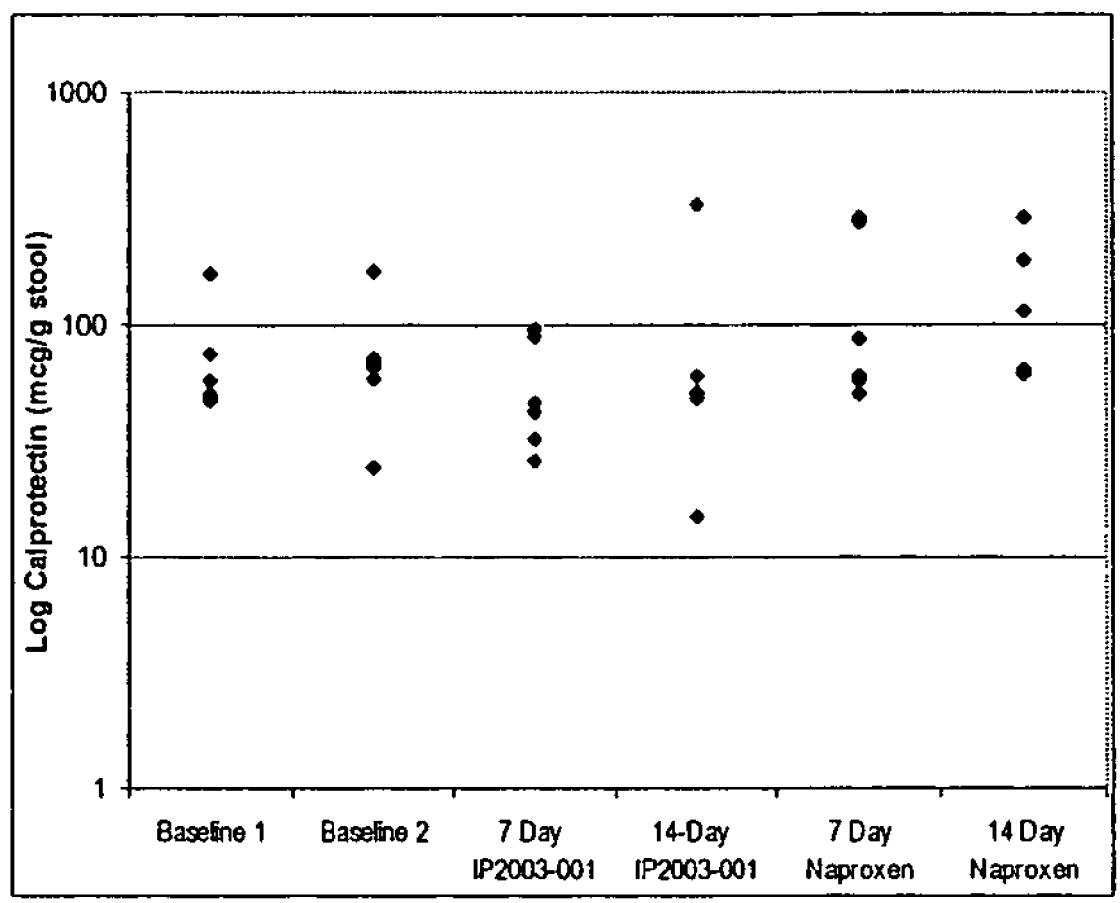
FIG. 15 shows individual calprotectin for the subjects who had baseline values above the reference range, or >50 µg/g stool (N=6). Baseline 1 is the average of both V1 values and Baseline 2 is the value after the 21-day wash-out. The 7 day and 14 day data for IP2003-001CT and naproxen are shown.
Figure 16:
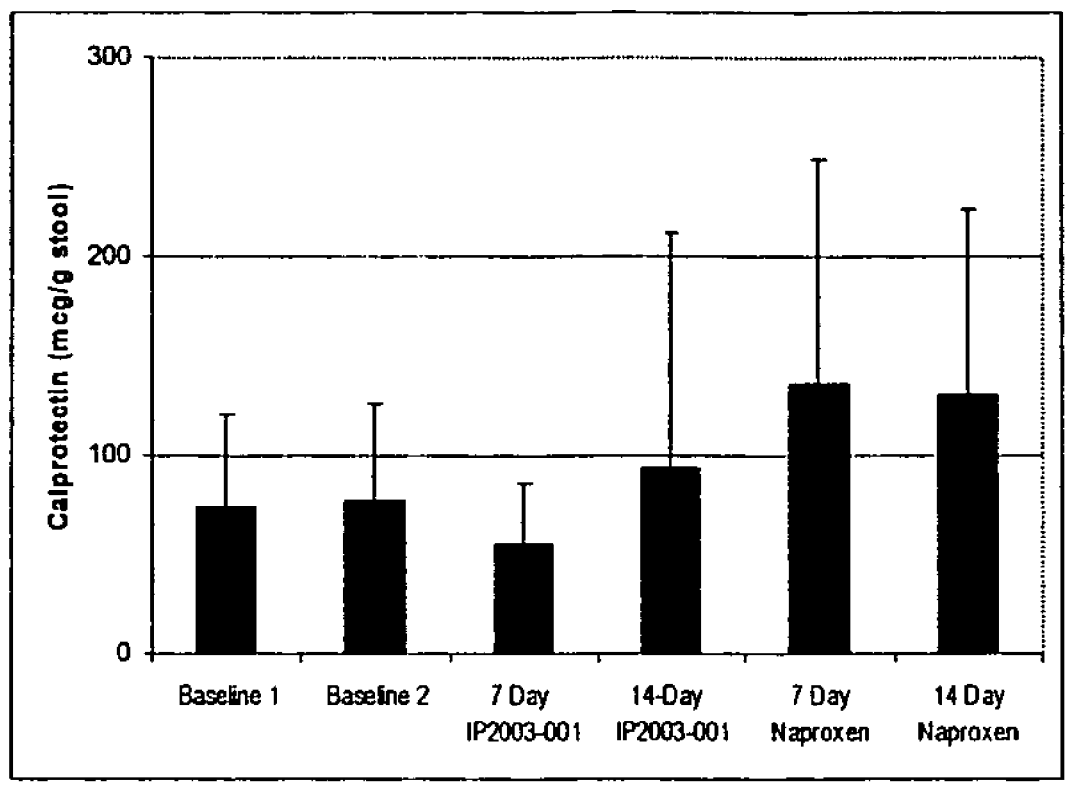
FIG. 16 shows mean fecal calprotectin for the subjects who had baseline values above the reference range, or >50 µg/g stool (N=6). Baseline 1 is the average of both V1 values and Baseline 2 is the value after the 21-day wash-out. The 7 day and 14 day data for IP2003-001CT and naproxen are shown.
Figure 17:
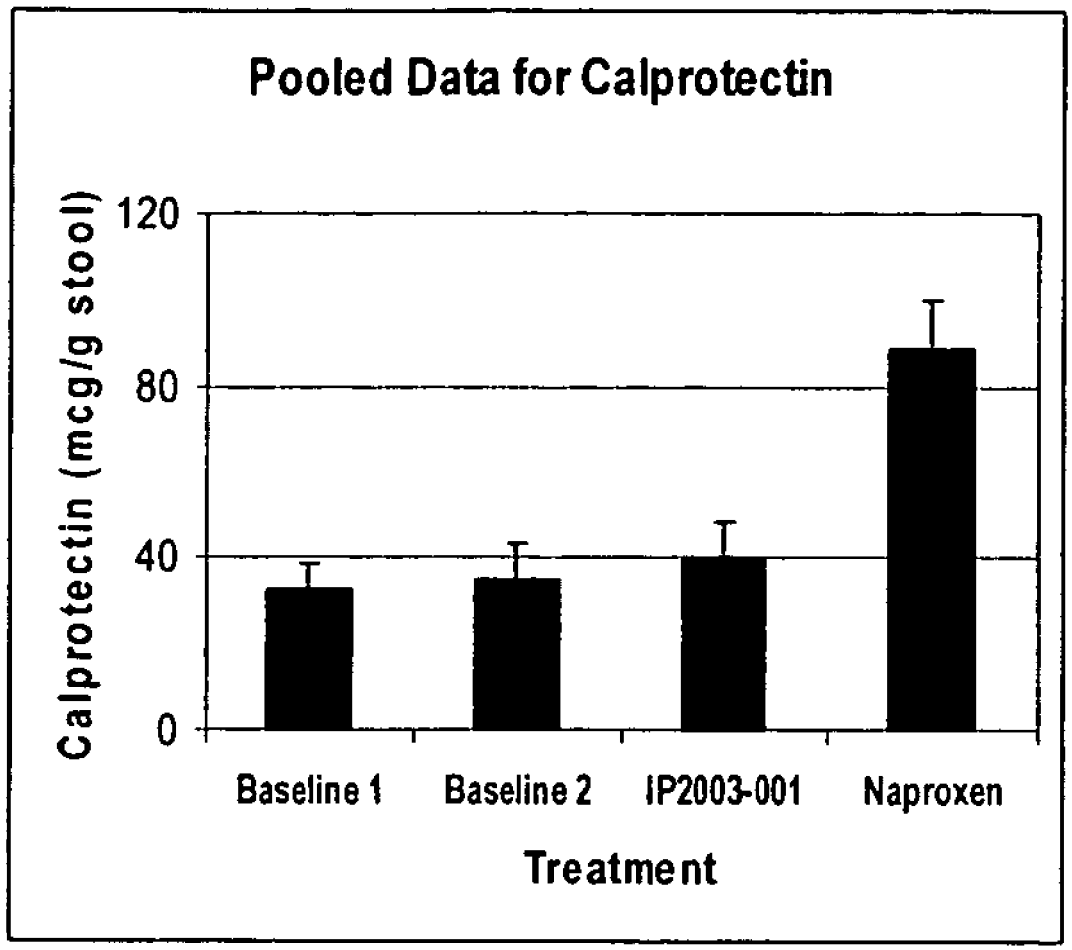
FIG. 17 shows pooled calprotectin data (mean±sem) for the subjects on the clinical trial. Baseline 1 is the average of all V1 baseline values. Baseline 2 is the average of all wash-out values. The 7 day and 14 day data for IP2003-001CT and naproxen were pooled for this analysis, respectively. No significant difference was observed between Baseline 1, Baseline 2, or IP2003-001; however, naproxen calprotectin levels were significantly elevated after treatment ($p<0.05$; Wilcoxon/Kruskal-Wallis ranked sums).

Results—As seen in FIG. 9, with increasing THIAA in the test formulation, the potential for inducing gastrotoxicity was decreased for both ibuprofen FIG. 9A and aspirin FIG. 9B.

Similar experiments are performed with various fractions isolated or derived from hops and various non-steroidal anti-inflammatory compounds such as NSAIDs.

EXAMPLE 9

Activity of Genus A and Genus B HOPS Derivates Against Stress-Induced Ulcers Stress-induced ulcers are experimentally induced in rats by encasing the animals in plaster of Paris bandages for 24 hours. The effect of compounds on formation of stress-induced ulcers is assessed by dosing the test compound one hour before encasing the rats in the bandage and again six hours after encasing the rats. After 24 hours, the bandage is removed and the gastric damage is assessed compared to untreated rats. Hops derivatives used were as previously described in EXAMPLE 3.

Treating the rats with 100 mg of test material/kg results in inhibition of the mean total ulcer score.

EXAMPLE 10

Influence of Genus A and Genus B HOPS Derivates on Gastric Damage Caused by Administration of Nonsteroidal Anti-Inflammatory Drugs in Rats Gastric damage caused by nonsteroidal, anti-inflammatory drugs is assessed by administering a dose of the test material followed later by a relatively high dose of the NSAID. After a further five hours, the extent of gastric damage is determined and percent inhibition is calculated. Hops derivatives used were as previously described in EXAMPLE 3.

Substantial inhibition of NSAID-induced gastric damage is observed with all hops derivatives.

EXAMPLE 11

Acute Toxicity of Genus A and Genus B HOPS Derivates in Rats

The acute toxicity of hops derivatives is examined in rats. Ten, young, Fisher 344 male rats averaging 100 g are orally dosed with 5000 mg test material/kg body weight and observed for 14 days; the number of dead rats is determined. The low acute toxicity of hops derivatives is illustrated by lack of lethality when administered to rats orally at 5,000 mg test material/kg body weight.

EXAMPLE 12

Reduction of Acute Toxicity of Aspirin when Administered in Conjunction with HOPS Derivatives The ability of hops derivatives to reduce acute toxicity of aspirin is examined in mice. Ten, young, male and female mice per group averaging 12 g are orally dosed with 50, 100, 500, 1000, or 5000 mg test material/kg body weight and observed for 14 days; the median lethal dose is computed as described in EXAMPLE 2. Oral administration of aspirin or a combination of aspirin and hops derivatives in a 1:1 ratio to male and female mice indicates a strong protective effect of the hops derivatives. Hops combinations with aspirin decrease or prevent lethality at all doses of aspirin.

Thus, among the various formulations taught there has been disclosed a formulation containing, as a first active component, a hops derivative described by the supragenus disclosed and as a second component a NSAID. It will be readily apparent to those skilled in the art that various changes and modifications of an obvious nature may be made without departing from the spirit of the invention. Such changes and modifications would include, but not be limited to, the incipient ingredients added to affect the capsule, tablet, powder, lotion, food or bar manufacturing process as well as vitamins, flavorings and carriers. Other such changes or modifications would include the use of herbs or other botanical products containing the combinations of the preferred embodiments disclosed herein. Many additional modifications and variations of the embodiments described herein may be made without departing from the scope, as is apparent to those skilled in the art. The specific embodiments described herein are offered by way of example only.

In conclusion, one embodiment is a composition for treating or preventing NSAID-induced gastropathy. The composition contains at least one hops derivative and a NSAID. The administration may be enteral or parenteral.

EXAMPLE 13

Comparison of the Effects of a Composition Containing HOPS Extract Versus Anti-Inflammatory Medication This example describes a randomized cross-over study to assess the effect of a composition containing hopes extract and a non-steroidal anti-inflammatory (NSAID), naproxen, on fecal calprotectin.

Trial Design—The trial was a randomized, cross-over study to compare the effects of IP2003-001CT and naproxen on fecal calprotectin. Subjects were screened for participation at Visit 0 (V0). If selected for participation in the trial, subjects returned for the first visit (V1). Two background fecal calprotectin samples were obtained between V0 and V1. Subjects were randomized and placed on either Arm 1 or Arm 2 of the trial. All subjects were instructed to abstain from alcohol ingestion from 1 week before trial initiation to the end of the entire trial.

Arm 1 subjects were assigned IP2003-001CT at 2 tablets bid (twice daily) at V1, which was taken for 14 days total. Visit 2 (V2) occurred at 1 days after V1 and Visit 3 (V3) occurred at day 14 days after V1. After a 21 day washout, subjects returned for Visit 4 (V4) and were assigned naproxen 500 mg bid for 14 days. Subjects returned for Visit 5 after 7 days (V5; 42 days total) and the final visit, Visit 6 (V6) at 49 days total.

Arm 2 subjects were assigned naproxen 500 mg bid at V1, which was taken for 14 days total. Visit 2 (V2) occurred at 7 days after V1, and Visit 3 (V3) occurred 14 days after V1. After a 21 day washout, subjects returned for Visit 4 (V4) and were assigned IP2003-001CT at 2 tablets bid for 14 days. Subjects returned for Visit 5 after 7 days (V5; 42 days total) and the final visit, Visit 6 (V6) at 49 days total.

Randomization was performed using a computer-generated randomization table (Microsoft Excel). Subjects were assigned to each arm on trial entry (V1).

Subjects were recruited through newspaper and radio advertisements. Men between ages 18 and 45 were initially screened by phone or e-mail. Inclusion criteria included body mass index (BMI) between 20 and 29 kg/m² and no indication of recent or past gastrointestinal disease and healthy as determined by normal standard blood tests.

Subjects were excluded if screening laboratory showed abnormal complete blood count (CBC), kidney or liver function markers, or blood glucose values. Subjects currently on prescriptive medications, and subjects who had used NSAIDs or aspirin in the 2 weeks preceding or oral corticosteroids in 4 weeks preceding trial initiation were excluded. Exclusion criteria also included allergy to any of the ingredients in the supplement, naproxen, NSAIDs, or aspirin; a history of peptic ulcer disease, gastritis, esophagitis, or liver, kidney, or heart disease; history of bleeding disorders; uncontrolled hypertension (blood pressure (BP)>140/90); diabetes; HIV; history of or active cancer (except skin cancer); history of untreated endocrine, neurological, or infectious disorder; history of serious mental illness or episode of attempted suicide within preceding 10 years.

Investigational Product—Each tablet of IP2003-001 contained: 200 mg reduced iso-alpha acids (as magnesium salt from *Humulus lupulus* cone extract), 200 mg rosemary extract (*Rosmarinus officinalis*), and 40 mg oleanolic acid (from olive leaf extract *Olea europaea*) with excipients of microcrystalline cellulose, silica, stearic acid, magnesium stearate, calcium silicate. Two of the ingredients in the tablets, rosemary and oleanolic acid, are included in the generally regarded as safe (GRAS) list by the United States Food and Drug Administration (FDA). Reduced iso-alpha acids from hops (RIAA) are food grade substances that are used as natural, foam-stabilizing and bittering compounds in beer making and have a history of safe use.

Naproxen (2-naphthaleneacetic acid, 5 methoxy-α-methyl-(+)) is a NSAID with analgesic and antipyretic properties. Naproxen is rapidly and completely absorbed from the gastrointestinal tract; peak plasma levels of naproxen are attained in 2 to 4 hours after administration, with steady-state conditions normally achieved after 4 to 5 doses. In clinical studies in arthritis patients, naproxen has been shown to be comparable to aspirin and indomethacin in controlling pain and joint stiffness. Adverse reactions of 3% or more occurrence with naproxen include: constipation, heartburn, abdominal pain, nausea, dyspepsia, diarrhea, stomatitis, headache, dizziness, drowsiness, lightheadedness, vertigo, itching (pruritus), skin eruption, ecchymoses, sweating, purpura, tinnitus, hearing disturbances, visual disturbances, edema, dyspnea, palpitations, and thirst.

Clinical and Laboratory Analysis—Blood was drawn at V0 for screening laboratories, and at V1, V3, V4, and V6 for high sensitivity C-reactive protein (hsCRP). Follow-up CBC and comprehensive metabolic panel/complete metabolic profile (CMP) were performed at V3 and V6 for monitoring of subject baseline laboratories. General laboratory, including CBC and chemistry panels during screening and hsCRP, were performed by Laboratories Northwest (Tacoma, Wash.).

Fecal calprotectin assays were performed using the PhiCal enzyme immunoassay (Great Smokies Diagnostic Laboratory, Asheville, N.C.). The test sensitivity is 15 µg/g stool (equivalent to 6.25 ng/mL) and the test is linear to 250 µg/g stool (equivalent to 100.00 ng/mL). Within run variation is 6% coefficient of variation (CV), and day-to-day variation is 14% CV.

Subjects were provided kits to obtain stool samples at home and bring them to each visit. Collection of stool samples was performed as described in literature provided by the manufacturer (Great Smokies Diagnostic Laboratory). Two stool samples were collected from the subjects at V1 for intra-individual variation and baseline determination. One stool sample was collected at V2, V3, V4, V5, and V6.

First morning urine was collected at home by each subject before V1, V2, V3, V4, V5, and V6. Urine was frozen for assessment of inflammatory mediators.

Vital signs and general physical exam was performed at each visit. At V2, V3, V4, V5, and V6, a general Tolerance Questionnaire was also obtained to assess for tolerance to the IP2003-001 and naproxen.

Statistical Methods—Data were analyzed by a one-way analysis of variance (ANOVA) using JMP Statistical Package (SAS Institute, Cary, N.C.). Significance was determined as $p<0.05$. Vitals and general laboratory data are presented as mean±standard error of the mean (sem) unless otherwise noted.

Calprotectin data were analyzed as follows: entries that were below the limit of detection (<15 µg/g stool) were converted to 15. Data were analyzed by ANOVA (Wilcoxon/Kruskal-Wallis ranked sums test). Data were also transformed logarithmically to insure homoscendasticity and all statistical tests were confirmed on the transformed data. Grubb's test for outliers was performed. Tukey's HSD test was used for post-hoc comparisons.

Results—Subjects—Twenty-six subjects were screened for the trial, and 24 subjects were selected for participation (FIG. 1). All subjects entered the trial voluntarily and signed informed consents. Of these subjects, 12 were assigned to Arm 1, and 11 subjects completed Arm 1. Twelve subjects were assigned to Arm 2, and 10 subjects completed Arm 2. Three subjects withdrew from the study, 1 from Arm 1 and 2 from Arm 2. Reasons for withdrawal were personal (schedule conflicts and personal interferences). No adverse events were reported during the trial.

The subjects on Arm 1 ranged in age from 19 years to 44 years, and ranged in BMI from 20 to 27 kg/m². The subjects on Arm 2 ranged in age from 25 years to 45 years, and ranged in BMI from 24 to 31 kg/m². Subject demographics are summarized in Table 8.

TABLE 8

Mean (±sd) age, BMI, and baseline calprotectin for the subjects completing the trial.

| | ARM 1 (N = 11) | ARM 2 (N = 10) |
|---|---|---|
| Age (years) | 33 ± 7 | 33 ± 9 |
| BMI (kg/m²) | 22.5 ± 3.5 | 27.3 ± 3.0 |
| Calprotectin (µg/g stool) | 44 ± 45 | 22 ± 24 |

Clinical observations—No significant changes were observed in vitals (BP or pulse) in subjects on either Arm 1 or Arm 2. BP readings for Arm 1 subjects were 125/68±9/8 (N=12) at V1 and 123/68±12/8 (N=10; 1 subject's data was not reported) at V6, with no significant changes at the visit in—between V1 and V6. BP readings for Arm 2 subjects were 123/72±7/12 (N=12) at V1 and 119/68±7/9 (N=10) at V6, with no significant changes at the visit in-between V1 and V6. No clinically significant change in weight was noted either, although 5 of the 11 subjects completing Arm 1 showed a gain of around 5 lb between V1 and V6 for an average increase of 3 lb (Table 9).

TABLE 9

Mean (±sd) weight for the subjects completing Arm 1 (N = 11) and Arm 2 (N = 10) of the trial.

| | Weight (lb) | | | |
|---|---|---|---|---|
| | V1 | V3 | V4 | V6 |
| Arm 1 | 168 (25) | 168 (24) | 169 (24) | 171 (25) |
| Arm 2 | 189 (27) | 190 (28) | 190 (26) | 190 (29) |

CRP—All subjects—The acute phase reactant, high sensitivity c-reactive protein (CRP), has been considered a marker for inflammation. Values of CRP at <1 mg/L are considered optimal, whereas values of >3.9 mg/L CRP are considered to be elevated. CRP values between 1.1 mg/L and 3.9 mg/L are considered moderately elevated.

The CRP values at V1 for subjects completing the trial ranged from <0.2 mg/L to 2.8 mg/L. Only 7 subjects had values higher than 1 mg/L. Little change was seen in CRP values (Table 10) except for 2 subjects on Arm 1, who showed elevated values at V6 only (19.8 mg/L and 23.4 mg/L).

TABLE 10

Mean (±sd) CRP (mg/L) for the subjects completing Arm 1 (N = 11) and Arm 2 (N = 10) of the trial.

| | hs-CRP (mg/L) | | | |
|---|---|---|---|---|
| | V1 | V3 | V4 | V6 |
| Arm 1 | 0.74 (0.82) | 0.65 (0.44) | 0.45 (0.30) | 3.19 (6.83) |
| Arm 2 | 0.87 (0.58) | 0.97 (0.66) | 1.02 (0.96) | 2.96 (5.96) |

Fecal Calprotectin—Two fecal calprotectin samples were obtained from the subjects prior to the consumption of the test substances. These baseline samples were obtained within 4 days of each other. The baseline fecal calprotectin values are shown in Table 11. Average baseline fecal calprotectin for all subjects was 37±8 μg/g stool. Ten subjects had average baseline values above 40 μg/g stool, and several subjects had values below the levels of detection (15 μg/g stool).

TABLE 11

Baseline calprotectin baseline data (μg/g stool) for subjects before V1. Independent stool samples taken within 4 days (V1.1 and V1.2) are shown. Data reported as <17 or <16 were converted to 15 (indicating below detection).

| PT# | V1.1 | V1.2 | Ave. | Variance |
|---|---|---|---|---|
| 1538 | 18 | 18 | 18 | 0 |
| 1516 | 36 | 41 | 39 | 5 |
| 1526 | 48 | 32 | 40 | 16 |
| 1527 | 50 | 46 | 48 | 4 |
| 1537 | 50 | 44 | 47 | 6 |
| 1539 | 58 | 57 | 58 | 1 |
| 1520 | 61 | 39 | 50 | 22 |
| 1224 | 212 | 120 | 166 | 92 |
| 1521 | 15 | 32 | 23 | 17 |
| 1530 | 15 | 15 | 15 | 0 |
| 1533 | 15 | 15 | 15 | 0 |
| 1535 | 15 | 15 | 15 | 0 |
| 1029 | 33 | 56 | 44 | 12 |
| 1532 | 22 | 22 | 22 | 0 |
| 1528 | 32 | 34 | 33 | 1 |
| 1531 | 32 | 19 | 26 | 13 |
| 1517 | 69 | 80 | 74 | 11 |
| 1536 | 72 | 25 | 48 | 47 |
| 1522 | 15 | 15 | 15 | 0 |
| 1529 | 15 | 15 | 15 | 0 |
| 1518 | 15 | 28 | 21 | 13 |
| 1525 | 15 | 15 | 15 | 0 |
| 1524 | 212 | ND | ND | ND |
| 1540 | 34 | 21 | 28 | 13 |
| Average | 48 | 35 | 41 | 21 |
| sem | 11 | 5.1 | 7.1 | 9.3 |

ND indicates not done.

Fecal calprotectin data for Arm 1 subjects during the trial are shown in Table 12. No significant difference was seen between Baseline 1 (47±13 μg/g stool) and V2 and V3 (36±7 μg/g and 36±6 μg/g stool, respectively), when the subjects were consuming IP2003-001. The wash-out value between the cross-over was also consistent with the initial baseline, at 46±14 μg/g stool. During the naproxen treatment, however, the fecal calprotectin value increased to 93±24 μg/g stool and 77±14 μg/g stool for V5 and V6, respectively.

TABLE 12

Individual calprotectin data (μg/g stool) for subjects completing Arm 1 of the trial. V1 is the average of the 2 baseline values. V2 and V3 occurred during treatment with IP2003-001. V4 is the calprotectin value after the 21-day wash-out. V5 and V6 occurred during treatment with naproxen. Data reported as <17 or <16 were converted to 15 (indicating the lowest level of detection).

| PT# | V1 | V2 | V3 | V4 | V5 | V6 |
|---|---|---|---|---|---|---|
| 1538 | 18 | 23 | 27 | 25 | 58 | 139 |
| 1516 | 39 | 21 | 15 | 15 | 129 | 44 |
| 1526 | 40 | 54 | 64 | 45 | 81 | 109 |
| 1527 | 48 | 39 | 22 | 20 | 22 | 144 |
| 1537 | 47 | 26 | 50 | 66 | 87 | 62 |
| 1539 | 58 | 32 | 15 | 24 | 57 | 62 |
| 1520 | 50 | 96 | 60 | 171 | 50 | 64 |
| 1224 | 166 | 46 | 51 | 72 | 60 | 115 |
| 1521 | 23 | 27 | 54 | 42 | 175 | 15 |
| 1530 | 15 | 15 | 15 | 15 | 21 | 15 |
| 1535 | 15 | 19 | 19 | 66 | 87 | 62 |
| AVE | 47 | 36 | 36 | 46 | 93 | 77 |
| sem | 13 | 7.0 | 6.0 | 14 | 24 | 14 |

Figure 2:
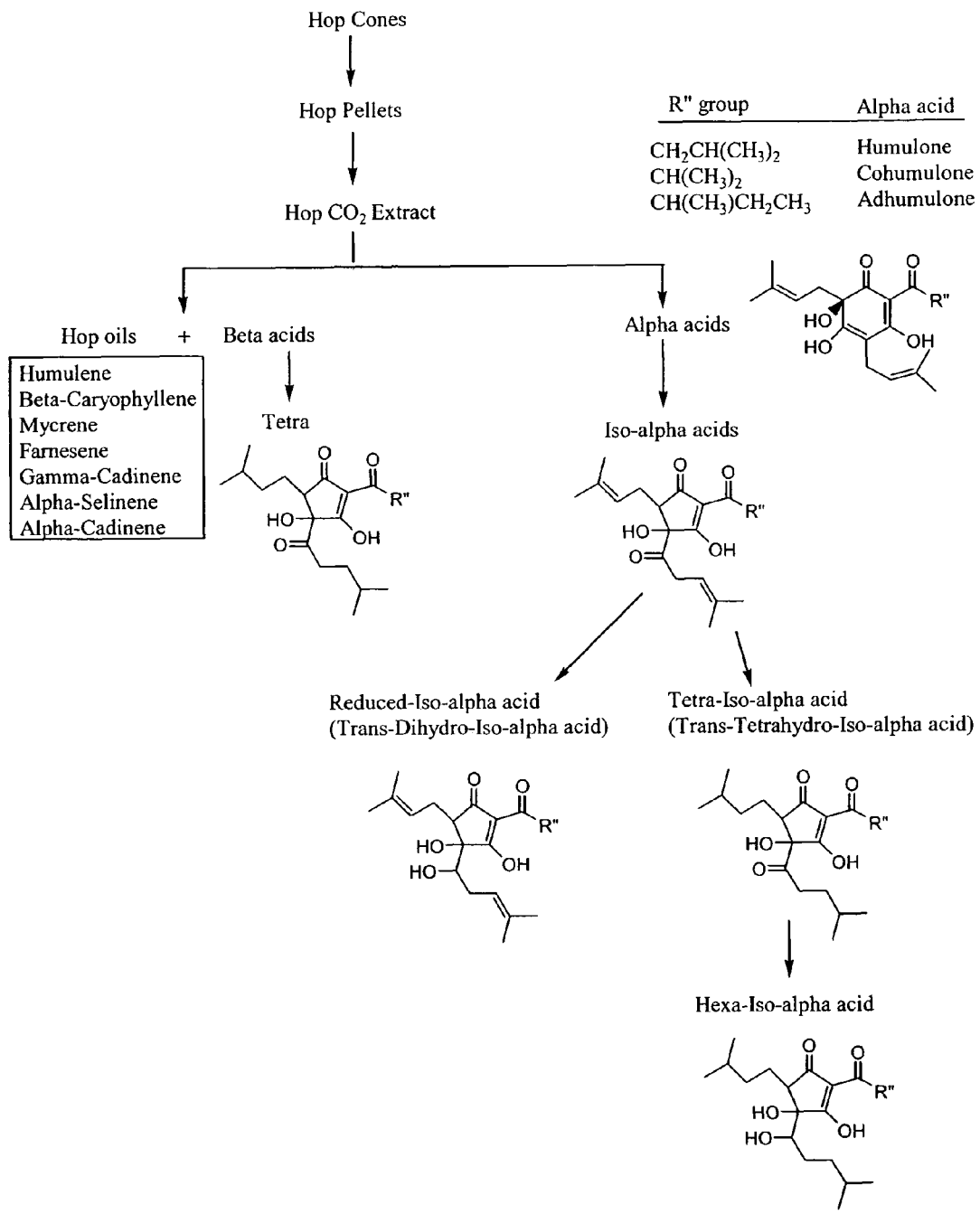
FIG. 2 shows an outline of fractions and compounds that can be obtained from hops.

Fecal calprotectin data for Arm 2 subjects during the trial are shown in Table 13. Baseline 1 for these subjects was 27±6.4 μg/g stool. The fecal calprotectin values during the naproxen treatment, V2 and V3, were increased to 93±32 μg/g stool and 96±26 μg/g stool, respectively. The fecal calprotectin value decreased to approximately Baseline 1 values after the wash-out (32±5.9 μg/g stool), and remained around this value at V4, during the IP1003-001 treatment (39±7.8 μg/g stool). Some increase was noted after 14 days on IP2003-001 for these subjects (64±30 μg/g stool), although this value was still below those observed during the naproxen treatment phase of the trial and was primarily due to 1 subject's data (#1517; see FIG. 2). The average fecal calprotectin of these subjects at V6 without subject #1417 was 48±17 μg/g stool.

TABLE 13

Individual calprotectin data (μg/g stool) for subjects completing Arm 2 of the trial. V1 is the average of the 2 baseline values. V2 and V3 occurred during treatment with naproxen. V4 is the calprotectin value after the 21-day wash-out. V5 and V6 occurred during treatment with IP2003-001. Data reported as <17 or <16 were converted to 15 (indicating below detection).

| PT# | V1 | V2 | V3 | V4 | V5 | V6 |
|---|---|---|---|---|---|---|
| 1029 | 44 | 56 | 107 | 25 | 36 | 27 |
| 1532 | 22 | 79 | 77 | 30 | 18 | 36 |
| 1528 | 33 | 60 | 78 | 34 | 39 | 57 |
| 1531 | 26 | 47 | 48 | 21 | 18 | 15 |
| 1517 | 74 | 287 | 292 | 68 | 90 | 334 |
| 1536 | 48 | 274 | 189 | 59 | 42 | 48 |
| 1522 | 15 | 17 | 28 | 15 | 15 | 15 |
| 1529 | 15 | 30 | 66 | 15 | 67 | 15 |
| 1518 | 21 | 52 | 42 | 41 | 46 | 36 |
| 1525 | 15 | 26 | 36 | 15 | 15 | 58 |
| AVE | 27 | 93 | 96 | 32 | 39 | 64 |
| sem | 6.4 | 32 | 26 | 5.9 | 7.8 | 30 |

Data for each treatment per each Arm were analyzed using paired T-Test ($V_i$ with $V_{i+1}$) and fecal calprotectin values were shown to increase significantly (p<0.05) for both the 7-day and 14-day naproxen treatment, whereas the IP2003-001 treatment resulted in no significant difference from Baseline 1. Baseline 1 and Baseline 2 also did not differ significantly. Pooled data and are shown graphically in FIGS. 2 and 3.

Review of the data showed that some subjects had baseline calprotectin levels above the reference range. Some literature suggests this could occur from temporary upper respiratory infections (URIs), alcohol consumption, consumption of other drugs that may influence the mucosa, or presence of previously undetected gastrointestinal inflammation (Tibble and Bjarnason, supra, 2001; Meling et al., supra, 1996; Tibble et al., supra, 1999). Therefore, the data were stratified by those subjects with both baselines below the reference range (<50 μg/g stool), and those with at least one baseline above the reference range (=50 μg/g stool).

Of the 21 subjects completing the trial, 15 had both baselines below the reference range. As shown in FIGS. 4 and 5, no significant difference was seen after 7- and 14-days of IP2003-001, which showed 30±4 μg/g stool and 40±11 μg/g stool, respectively. In this data set, only 1 subject had noticeably elevated calprotectin at day 14. In contrast, fecal calprotectin after the naproxen treatment was significantly elevated (p<0.05) at both 7- and 14-days, at 76±19 μg/g stool and 60±10 μg/g stool, respectively. (Note, data are graphed as mean±sd in FIG. 5.)

Figure 6:
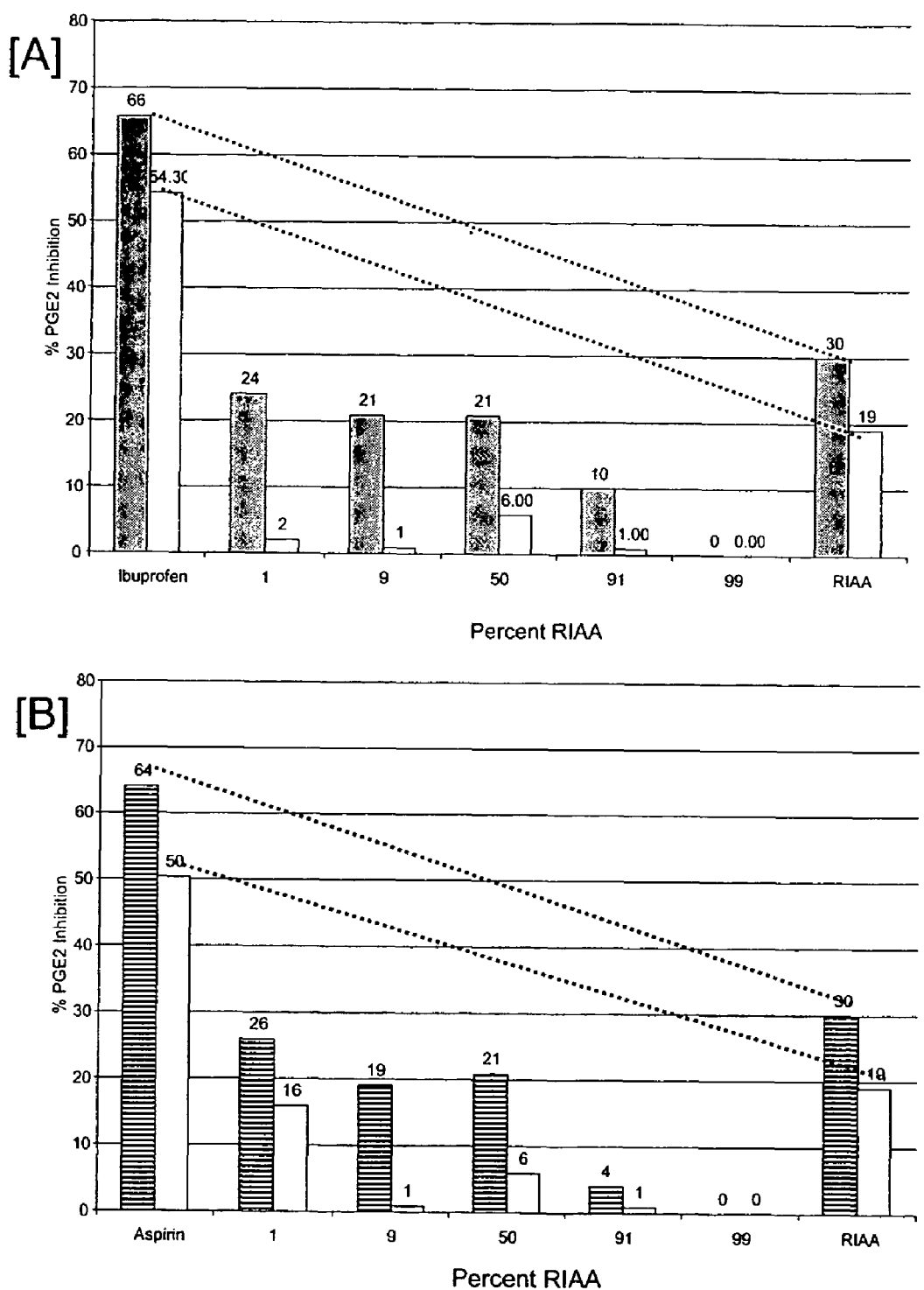
FIG. 6 illustrates percent inhibition of $PGE_2$ biosynthesis in AGS gastric mucosal cells by representative Genus A reduced isomerized alpha acid (RIAA) species.
Figure 7:
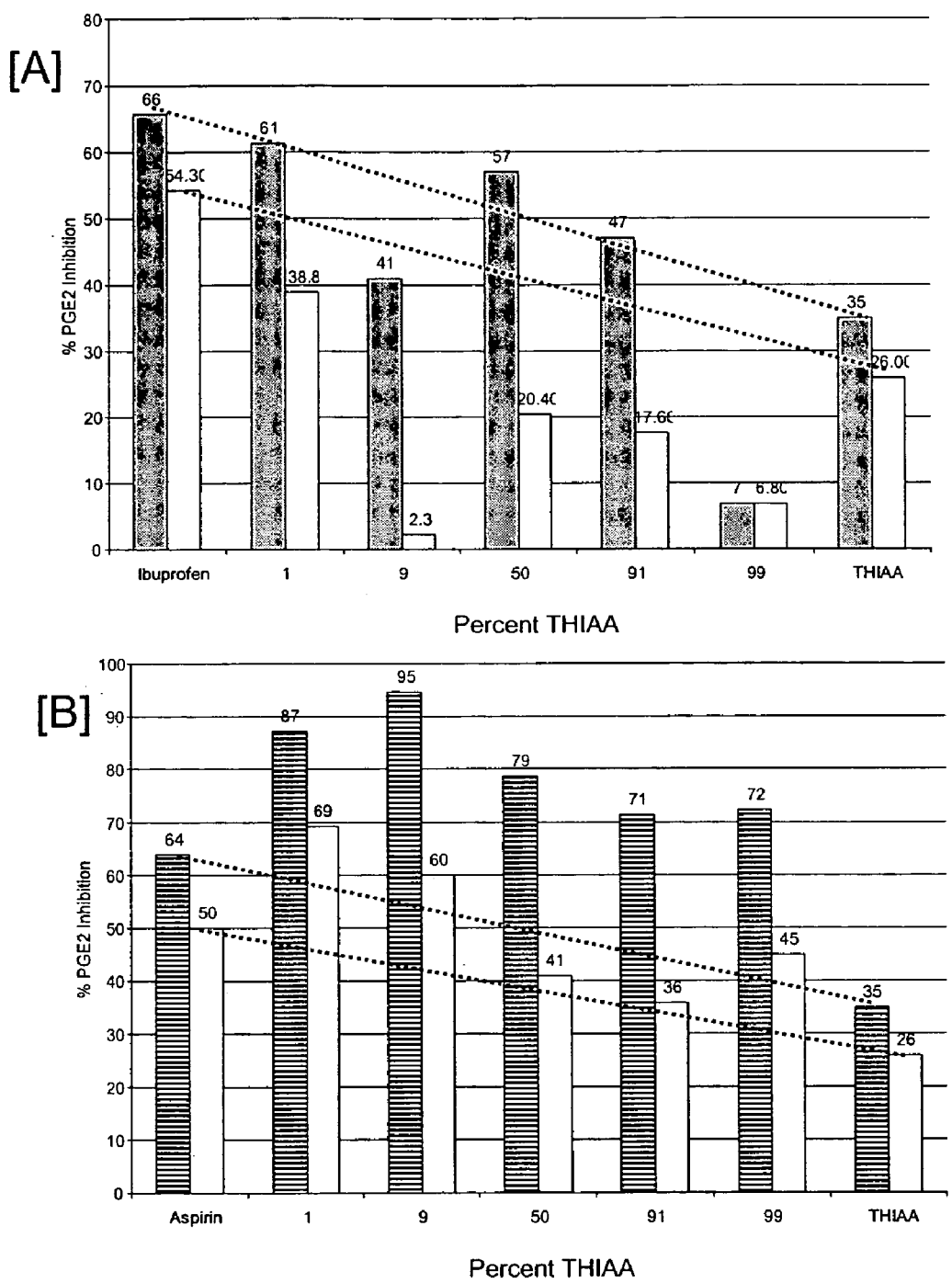
FIG. 7 illustrates percent inhibition of $PGE_2$ biosynthesis in AGS gastric mucosal cells by representative Genus B tetrahydroisoalpha acid (THIAA) species and NSAIDS.

Six of the 21 subjects completing the trial had at least 1 baseline above the reference range. In these subjects, the baseline calprotectin levels (V1 and V4) were 74±19 Og/g stool and 77±20 μg/g stool. As shown in FIGS. 6 and 7, fecal calprotectin after IP2003-001 remained relatively stable with baseline in these subjects as well, with 7- and 14-day values at 55±12 μg/g stool and 93±49 μg/g stool, respectively. Only 1 subject showed a noticeably elevated calprotectin level at day 4, and this subject's data was the main contributor to the elevation in the 14-day calprotectin level after IP2003-001 for this data set. As observed with the previous group, however, the fecal calprotectin after naproxen treatment was elevated at both 7- and 14-days, at 136±46 μg/g stool and 131±38 μg/g stool, respectively, however these changes were not significant. (Note, data are graphed as mean±sd in FIG. 7.)

Finally, since the 7-day and 14-day treatment data were consistent within specific treatments, the 7-day and 14-day data were pooled for analysis. As shown in Table 14, no difference was noted between baselines. However, fecal calprotectin after the naproxen treatment was significantly elevated from baseline (89±11 μg/g stool; p<0.05), whereas the fecal calprotectin values after IP2003-001 was not significantly elevated (40±8.2 μg/g stool; ns).

TABLE 14

Pooled calprotectin data (mean ± sem) for the subjects on the trial. The number in parentheses indicates the number of data points per each condition. Baseline 1 is the average of all V1 baseline values. Baseline 2 is the average of all wash-out values. The 7 day and 14 day data for IP2003-001CT and naproxen were pooled for this analysis, respectively.

| | Calprotectin (μg/g stool) | Significance (p) |
|---|---|---|
| Baseline 1 (42) | 33 ± 5.9 | ns |
| Baseline 2 (21) | 35 ± 8.5 | ns |
| IP2003-001CT (42) | 40 ± 8.2 | ns |
| Naproxen (42) | 89 ± 11* | <0.05 |

The * indicates data that are significantly different from Baseline 1 by Wilcoxon/Kruskal-Wallis ranked sums.

Summary—A marker of gastrointestinal inflammation, namely assessment by fecal calprotectin, has been used to investigate the effect of IP2003-001 on gastrointestinal integrity. In this randomized, cross-over study, 21 healthy subjects were treated with IP2003-001 (2 tablets bid), or a control substance that has been reported to lead to gastrointestinal inflammation and increased fecal calprotectin levels, naproxen (500 mg bid) for 14 days. A 21-day washout occurred between the crossover treatments and no significant difference in calprotectin levels was observed between the two baselines. Fecal calprotectin assessment was performed at 7- and 14-days during treatment for each arm of the trial and compared to the baselines.

The treatment with IP2003-001 resulted in no significant increase after 7 or 14 days. Only 2 subjects showed noticeably elevated calprotectin values after the IP2003-001 treatment. In contrast, the naproxen treatment resulted in a noticeable elevation in fecal calprotectin at both the 7- and 14-day assessments in more than 50% of the subjects. (Note: The increase observed after naproxen is of the same order of magnitude as the ~2-fold increase that has been reported after 7- and 14-days of treatment with 500 mg bid; Meling et al., supra, 1996).

Since calprotectin is a marker for gastrointestinal inflammation, these data indicate that IP2003-001 leads to little or no gastrointestinal inflammation, as compared to a standard NSAID, and suggest calprotectin may not carry the risk of ulcers that NSAIDs commonly produce.

EXAMPLE 14

Testing of UltraInflamX™ Anti-Inflammatory Components in the AGS Gastric Mucosal Cell Model UltraInflamX™ is a low-allergy potential, nutritionally fortified, vegetarian beverage drink mix designed for nutritional support of chronic inflammatory conditions of the lungs, joints and intestinal tract. UltraInflamX™ can be used as part of a comprehensive elimination or diet program, as well as nutritional support for patients involved in an anti-inflammatory lifestyle program. As UltraInflamX™ is designed for use on a chronic basis and several of its components have anti-inflammatory properties, it was of interest to assess the potential of these components to induce gastrointestinal toxicity characteristic of non-steroidal anti-inflammatory compounds. The objective of this study was to test the anti-inflammatory components of UltraInflamX™, in combination and individually, for inhibition of $PGE_2$ biosynthesis in the recently developed AGS human gastric mucosal cell line assay.

The test materials included the active anti-inflammatory components of UltraInflamX™, curcumin, ginger root, rosemary extract and rutin, and a composite of these components formulated in the ratio of 2:1:1:2 respectively. A minimum of four concentrations, 50, 5, 0.5 and 0.05 µg test material/mL, with two replicates per concentration over three independent experiments were used to compute dose-response curves of $PGE_2$ inhibition in AGS cells. The calcium ionophore A23187 was used to induce arachidonic acid release and was added 60 minutes after exposing the AGS cells to the test material. Medium inhibitory concentrations ($IC_{50s}$) with their 95% confidence intervals were computed from the average of the three independent experiments. Synergy or antagonism of test components was quantified using the combination index (CI) parameter. This is discussed in more detail below.

Test Materials and Chemicals—The anti-inflammatory components of UltraInflamX™, which included curcumin, ginger root, rosemary extract and rutin, were supplied by Metagenics (Gig Harbor, Wash.). A composite of these materials that was formulated in the ratio present in commercial UltraInflam™ (2:1:1:2 respectively) was also provided by Metagenics.

$PGE_2$ EIA kits were obtained from Cayman Chemicals (Ann Arbor, Mich.). Heat inactivated Fetal Bovine Serum (FBS-HI Cat. #35-011CV), and Dulbecco's Modification of Eagle's Medium (DMEM Cat #10-013CV) was purchased from Mediatech (Herndon, Va.). IL-113, aspirin and all standard chemicals, unless noted, were obtained from Sigma (St Louis, Mo.) and were of the highest purity commercially available. A detailed listing of suppliers is presented with each standard operating procedure in the attached appendices.

Cell Culture—The AGS human gastric mucosal cell line (American Type Culture Collection, Manassas, Va.) was cultured and maintained according to recommended ATTC methodology. Subcultured AGS cells were grown in IMDM with 20% FBS, 50 units penicillin/mL, 50 µg streptomycin/mL and maintained in log phase prior to each experiment. For $PGE_2$ assays, approximately $10^5$ cells per well were plated into 96-well plates in 200 µL growth medium per well. Cells were grown to 80% confluence and washed three times with IMDA media prior to addition of test agent. Test materials were added in 200 µL of IMDA media containing no FBS or penicillin/streptomycin. Sixty minutes following addition of the test materials, arachidonic acid was induced with the addition of the calcium ionophore A23187 in DMSO. Incubation at 37° C. was carried out for an additional 30 minutes. Fifty microliters of media were sampled for $PGE_2$ determination.

Determination of $PGE_2$—A commercial, non-radioactive procedure for quantification of $PGE_2$ was employed (Caymen Chemical, Ann Arbor, Mich.) for the determination of $PGE_2$ and the recommended procedure of the manufacturer will be used without modification. In summary, 50 µL of the supernatant culture medium, along with a serial dilution of $PGE_2$ standard samples, were mixed with appropriate amounts of acetylcholinesterase-labeled tracer and $PGE_2$ antiserum, and incubated at room temperature for 18 h. Afterwards, the wells in the $PGE_2$-assay microtiter plate were emptied and rinsed with wash buffer, 200 µL of Ellman's reagent containing substrate for acetylcholinesterase were then added. The reaction was performed on a slow shaker at room temperature for 1 h and the absorbance at 415 nm was determined in a Bio-tek Instruments (Model #Elx800, Winooski, Vt.) ELISA plate reader. The manufacturer's specifications for this assay include an intra-assay coefficient of variation of <10%, cross reactivity with $PGD_2$ and $PGF_{2\alpha}$ of less than 1% and linearity over the range of 10-1000 µg mL$^{-1}$. The $PGE_2$ concentration is reported as µg $PGE_2$/mL.

Cell viability—Cell viability was assessed by visual inspection. None of the test materials affected cell viability at the concentrations tested.

Calculations—A minimum of four concentrations, 50, 5, 0.5 and 0.05 µg material/mL, with two replicates per concentration over three independent experiments were used to compute dose-response curves and medium inhibitory concentrations ($IC_{50s}$) with their 95% confidence intervals using CalcuSyn (BIOSOFT, Ferguson, Mo.). This statistical package performs multiple drug dose-effect calculations using the Median Effect methods described by T-C Chou and P. Talalay (Chou, *J. Theor. Biol.* 35:285-297 (1972); Chou, *J. Theor. Biol.* 59:253-276 (1976); Chou an Talalay, *J. Biol. Chem.* 252:6438-6442 (1977); Chou and Talalay, *Eur. J. Biochem.* 115:207-216 (1981); Chou and Talalay, *Adv. Enzymol.* 22:27-55 (1984)). The fractional inhibition at each dose was averaged over the three independent experiments and used to calculate dose-response curves and the median inhibitory concentrations reported. Aspirin was used as a positive control in all experiments. Complete dose-response curves with coefficients of determination equal to or greater than 0.95 were obtained for all test materials.

Synergy or antagonism of test components was quantified using the combination index (CI) parameter. The CI of Chou-Talaly is based on the multiple drug-effect and is derived from enzyme kinetic models (Chou, supra, 1972; Chou, supra, 1976; Chou and Talalay, supra, 1977; Chou and Talalay, supra, 1981; Chou and Talalay, supra, 1984). The equation determines only the additive effect rather than synergism or antagonism. However, synergism is defined as a more than expected additive effect, and antagonism as a less than expected additive effect. Using the designation of CI=1 as the additive effect, for mutually exclusive compounds that have the same mode of action or for mutually non-exclusive drugs that have totally independent modes of action the following relationships were obtained: CI<1, =1, and >1 indicating synergism, additivity and antagonism, respectively. Additionally, an estimate of the expected median inhibitory concentration of the composite was made using the relationship: $1/IC_{50} = A/IC_{50A} + B/IC_{50B} + \ldots + N/IC_{50N}$, where A, B and N were the relative fractions of each component and $A+B+ \ldots +N=1$.

Results—COX-2 inhibitory activity of UltraInflamX™ components—Median inhibitory concentrations of $PGE_2$ synthesis of the test materials in the AGS cell model are presented in Table 15 Aspirin, the positive control yielded an $IC_{50}$ of 1.2 µg/mL (95% Confidence Interval=0.37-4.1), consistent with the previously reported value in AGS cells with A23187 of 2.9 µg/mL. Of the UltraInflamX™ anti-inflammatory components, curcumin and ginger root exhibited the lowest $IC_{50}$ values, respectively, 2.9 and 4.1 µg/mL. At the other end of the response spectrum, rutin and rosemary extract were least inhibitory to $PGE_2$ synthesis in AGS cells with $IC_{50}$ values of 20 and 43 µg/mL, respectively.

TABLE 15

Median inhibitory concentrations (IC50) for PGE$_2$ synthesis of UltraInflamX ™ components in the AGS cell model.†

| Compound | AGS IC$_{50}$ [μM] | 95% Confidence Interval [μM] | r |
|---|---|---|---|
| Composite | 14 | (7.0-30) | 0.984 |
| Curcumin | 2.9 | (1.2-7.2) | 0.959 |
| Ginger root | 4.1 | (1.7-10) | 0.974 |
| Rosemary extract | 43 | (8-226) | 0.999 |
| Rutin | 20 | (10-22) | 0.973 |
| Aspirin - positive control | 1.2 | (0.37-4.1) | 0.950 |

†Values are computed from the average of three independent assays; AGS cells were plated and allowed to reach 80% confluence. Cells were washed and test material was added 60 minutes prior to treatment with A23187. Thirty minutes later, media was removed for PGE$_2$ determination.

Experiments were also performed with a composite of 4 actives. Observed and expected IC$_{50}$ values for composites was based on weight of whole sample (nine components): observed, 14 μg/mL; expected 11 μg/mL. Observed and estimated IC$_{50}$ values for composite actives is based upon the percent weight of the four actives in the composite sample (45.3%): observed, 6.5 μg/mL; expected 5.7 μg/mL.

Figure 18:
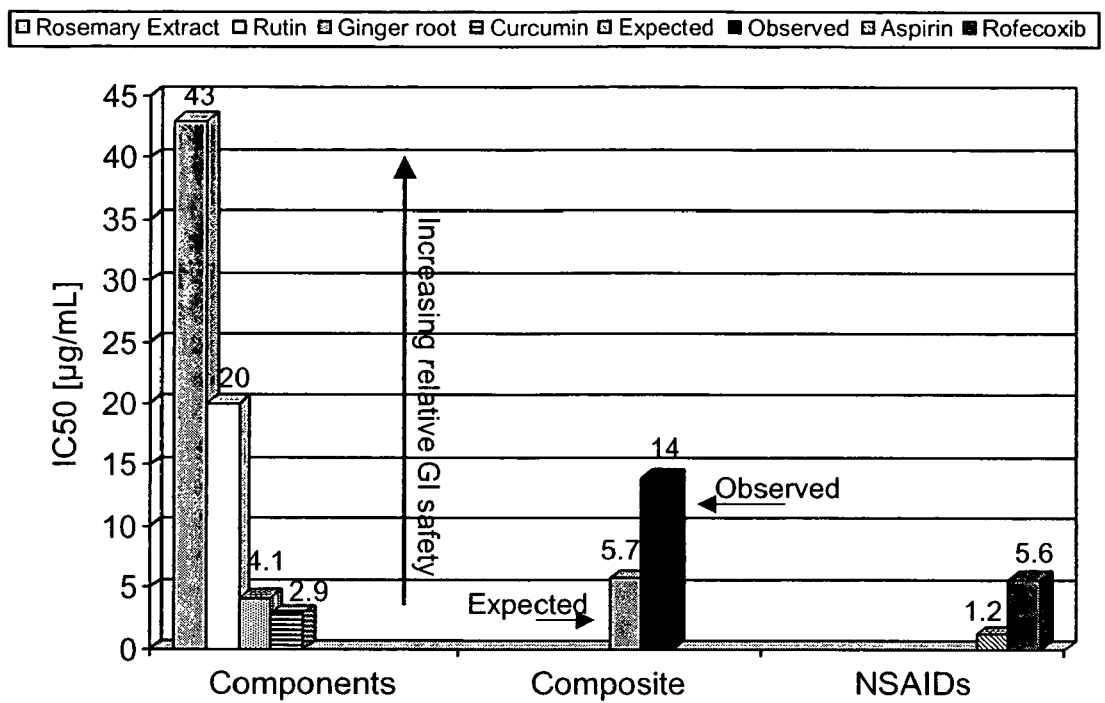
FIG. 18 shows median inhibitory concentrations for $PGE_2$ synthesis of UltraInflamX™ components in the AGS cell model.

The composite of anti-inflammatory ingredients produced an IC$_{50}$ of 14 μg/mL. The CI for the composite formulation, computed at 50, 75 and 90 percent inhibition were 7.3, 127 and 2250 (Table 16). These high CI values indicate extremely strong antagonism among the ingredients. Such an antagonistic effect is highly desirable, since it indicates a decrease in the expected gastrointestinal toxicity of the composition relative to its ingredients. Based upon the IC$_{50}$ values of each component and their relative amounts, the expected IC$_{50}$ of the composite was estimated at 5.7 μg/mL. This predicted value is below the lower estimate of the 95% confidence value of 7.0 μg/mL for the composite, supporting the antagonism calculation and CI values (see FIG. 18).

TABLE 16

Computed combination Index (CI) for the dose-response curves curcumin, ginger root, rosemary extract, rutin and the UltraInflamX ™ composite in a ratio of 2:1:1:2.

| Test Material | CI$_{50}$ | CI$_{75}$ | CI$_{90}$ | Mean CI | r |
|---|---|---|---|---|---|
| UltraInflamX ™ anti-inflammatory composite | 7.3 | 127 | 2250 | 795 | 0.984 |

CIs were computed for 50, 75 and 90 percent inhibition of PGE$_2$ biosynthesis in AGS human gastric mucosal cells.

Curcumin with an IC$_{50}$ of 2.9 μg/mL and ginger root with an IC$_{50}$ of 4.1 μg/mL were similar to aspirin in their inhibitory effects on PGE$_2$ synthesis in the AGS gastric mucosal cell model. Rutin and rosemary extract were least inhibitory to PGE$_2$ synthesis with IC$_{50}$ values of 20 and 43 μg/mL, respectively. This combination of ingredients exhibited exceptionally strong antagonism indicating a decrease in the expected gastrointestinal toxicity of the composition relative to its components.

As a composite, the anti-inflammatory ingredients of UltraInflamX™, with an AGS IC$_{50}$ of 14 μg/mL, would be classified as possessing relatively low gastrotoxic potential. For perspective, this value represents a potential for gastrotoxicity as estimated by the AGS model that is 12-times lower than aspirin or 2.5-times lower than rofecoxib.

Based upon the IC$_{50}$ values of each component and their relative amounts, the expected IC$_{50}$ of the composite was estimated at 5.7 μg/mL. The CI for the composite formulation, computed at 50, 75 and 90 percent inhibition were 7.3, 127 and 2250. These high CI values indicate extremely strong antagonism among the ingredients. Such an antagonistic effect is highly desirable, since it indicates a decrease in the expected gastrointestinal toxicity of the composition relative to its ingredients.

The components of the test materials are shown in Table 17.

TABLE 17

Highlighted ingredients in composite test materials.

| Highlighted Ingredient | gms/serving | Ratio | Percent Composite |
|---|---|---|---|
| Curcumin† | 0.2105 | 2 | 15.3 |
| Ginger root† | 0.1000 | 1 | 7.3 |
| Rosemary extract† | 0.1000 | 1 | 7.3 |
| Rutin† | 0.2109 | 2 | 15.4 |
| Quercetin | 0.2300 | 2 | 16.8 |
| Hespiridin Powder | 0.2040 | 2 | 14.9 |
| D-Limonene | 0.1110 | 1 | 8.0 |
| N-Acetylcysteine | 0.1070 | 1 | 7.8 |
| L-Citrulline | 0.1000 | 1 | 7.3 |

†Potential anti-inflammatory components

Figure 19:
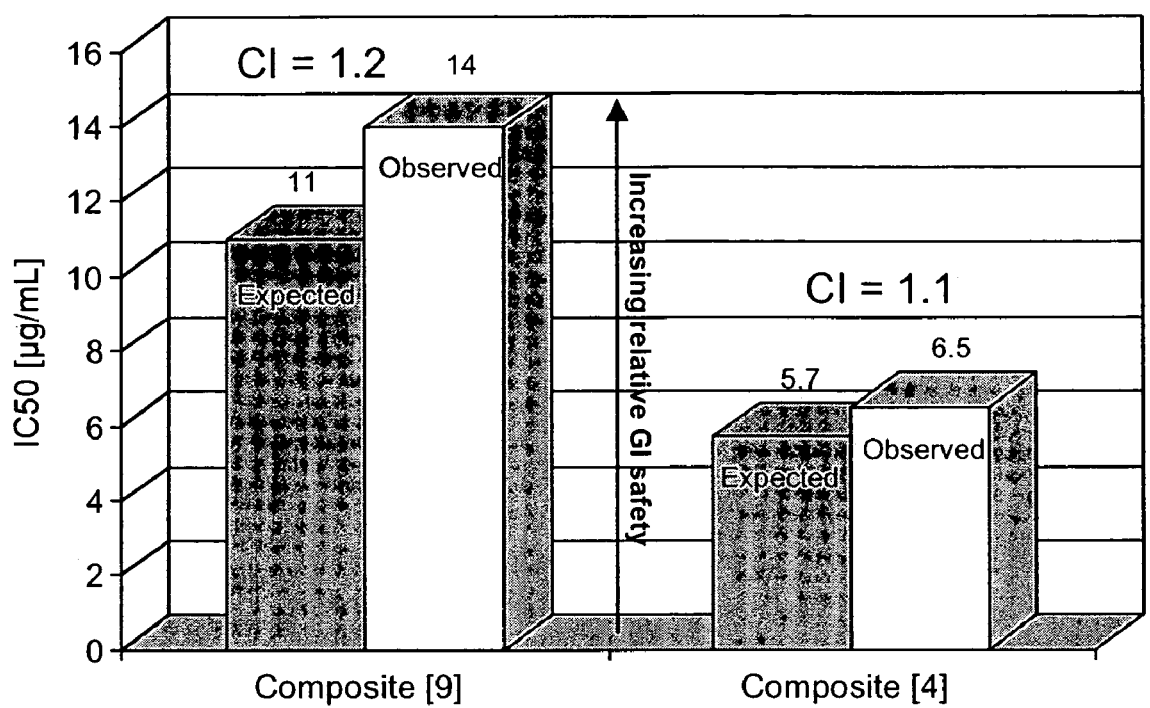
FIG. 19 shows expected and observed median inhibitory concentrations for $PGE_2$ synthesis of UltraInflamX™ components in the AGS cell model. $IC_{50}$ values were computed from the average of three independent assays; AGS cells were plated and allowed to reach 80% confluence. Cells were washed and test material was added 60 minutes prior to treatment with A23187. Thirty minutes later, media was removed for $PGE_2$ determination. Observed and expected $IC_{50}$ value for composite is based on weight of whole sample (nine components) and the observed and estimated $IC_{50}$ value for composite actives is based upon the percent weight of the four actives in the composite sample (45.3%).

The composite sample produced an observed IC$_{50}$ of 14 μg/mL based upon total weight of test material, all nine components. This value was greater than the expected IC$_{50}$ for the combination of all nine components estimated at 11 μg/mL. When the IC$_{50}$ was computed based on only the four, individually-tested components the observed value was 6.5 μg/mL with an expected IC$_{50}$ of 5.7 μg/mL (see FIG. 19).

The computed combination index (CI) for the composites are shown in Table 18.

TABLE 18

Computed combination Index (CI) values for the dose-response curves of the complete composite sample (9 components) and the four putative, anti-inflammatory components curcumin, ginger root, rosemary extract, and rutin.

| Test Material | CI$_{50}$ | CI$_{75}$ | CI$_{90}$ | Mean CI | r |
|---|---|---|---|---|---|
| UltraInflamX ™ total composite [9] | 1.2 | 22 | 401 | 141 | 0.985 |
| UltraInflamX ™ anti-inflammatory composite [4] | 1.1 | 19 | 341 | 120 | 0.984 |

CIs were computed for 50, 75 and 90 percent inhibition of PGE$_2$ biosynthesis in AGS human gastric mucosal cells. CI values for both sets of calculations indicate synergy beginning at the IC$_{50}$ and increasing dramatically with increasing dose.

Table 19 shows fractional amounts of herbs in a natural product-based anti-inflammatory.

TABLE 19

Fractional amounts of herbs in a natural products based anti-inflammatory.

| E. DIETARY SUPPLEMENT (INFLAVONOID IC INGREDIENTS) | Amount in Formulation [mg] | Relative Amount [Fraction†] |
|---|---|---|
| Ascorbic acid (RM07453) | 119 | 0.094 |
| Lemon Bioflavonoid (RM07150) | 100 | 0.079 |
| Boswellin (RM07781) | 211 | 0.166 |
| Cayenne Pepper (RM06572) | 25 | 0.020 |
| Quercetin (RM07671) | 57 | 0.045 |

TABLE 19-continued

Fractional amounts of herbs in a natural products based anti-inflammatory.

| E. DIETARY SUPPLEMENT (INFLAVONOID IC INGREDIENTS) | Amount in Formulation [mg] | Relative Amount [Fraction†] |
|---|---|---|
| Ginger (RM07782) | 100 | 0.079 |
| Curcumin Granular (RM06656) | 150 | 0.118 |
| Total of supplements = | 762 | 0.601 |
| Complete formulation††† | 1267 | 1.00 |

†Represents supplement fraction of complete formulation (1267 mg) including excipient ingredients listed below.
††NA = no activity; parenthetic values are 95% confidence intervals of the IC50 calculations.
†††Also contained the inert, excipient ingredients dihydrous calcium phosphate (456 mg), magnesium stearate (75 mg), Cabosil (5 mg), Syloid (245 mg) and stearic acid (149 mg).

Figure 20:
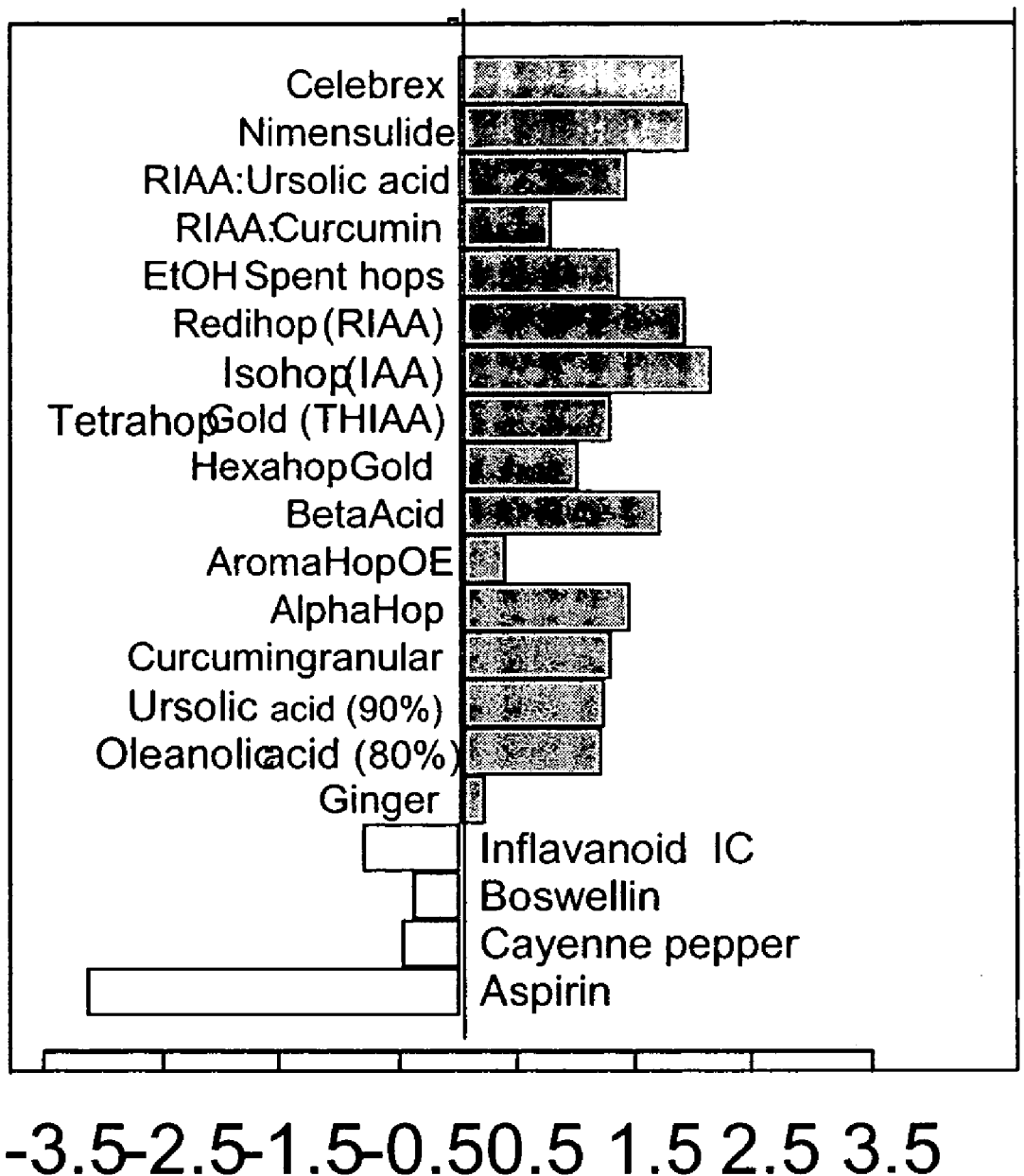
FIG. 20 shows COX-2 selectivity of prescription (Rx), over the counter (OTC), and dietary supplement health and education act (DSHEA) compounds.

Spice ingredients from a commercial anti-inflammatory product were tested individually and in combination in a RAW264.7 cell system under conditions assaying COX1 or COX2 activity. As shown in FIG. 20, bars with more gastrotoxic activity (favoring COX1) are to the left of zero, and bars depicting less gastrotoxic (favoring COX2 activity) activity are to the right. These data show that spices such as cayenne pepper, boswellin, and ginger individually have unexpectedly more predicted COX1 activity individually than in the fractional combination above (Inflavonoid IC), and demonstrate that combinational effects can exist among various spice ingredients resulting in greater COX2 selectivity and less predicted gastrotoxicity.

Tables 20 and 21 show decreased potential gastropathy of RIAA:rosemary combinations.

TABLE 20

Median inhibitory concentrations ($IC_{50}$) for $PGE_2$ synthesis of selected natural components in the RAW and AGS cell models†.

| Compound | RAW COX-2 [μg/mL] | AGS $IC_{50}$ [μg/mL] | COX-2 Selectivity AGS/RAW |
|---|---|---|---|
| Curcumin | 2.8 | 2.9 | 1.0 |
| Ginger root | 0.98 | 4.1 | 4.2 |
| Rosemary extract | 0.51 | 4.0 | 7.8 |
| RIAA | 0.45 | 21 | 47 |
| Aspirin - positive control | 1.1 | 0.52 | 0.48 |

†Values are computed from the average of three independent assays; AGS cells were plated and allowed to reach 80% confluence. Cells were washed and test material was added 60 minutes prior to treatment with A23187. Thirty minutes later, media was removed for $PGE_2$ determination.

TABLE 21

Median inhibitory concentrations ($IC_{50}$) for $PGE_2$ synthesis of selected combinations of RIAA and rosemary in the AGS cell model†.

| Compound | RAW COX-2 [μg/mL] | AGS $IC_{50}$ [μg/mL] | COX-2 Selectivity AGS/RAW |
|---|---|---|---|
| Rosemary | 0.51 | 4.0 | 7.8 |
| RIAA | 0.98 | 21 | 47 |
| RIAA:Rosemary [2:1]†† | 0.61 | >50 | >82 |
| RIAA:Rosemary [1:1]†† | 0.67 | >50 | >74 |
| Aspirin - positive control | 1.1 | 0.52 | 0.48 |

†Values are computed from the average of three independent assays; AGS cells were plated and allowed to reach 80% confluence. Cells were washed and test material was added 60 minutes prior to treatment with A23187. Thirty minutes later, media was removed for $PGE_2$ determination.
††Estimated from harmonic mean of individual components, assumes no interaction for RAW cells.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A method of producing an analgesic and an anti-ulcerogenic effect in a mammal, comprising administering to the mammal an amount of a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone sufficient to produce an analgesic and anti-ulcerogenic effect in the mammal and a nonsteroidal anti-inflammatory compound selected from the group consisting of salicylic acid, methyl salicylate, difulunisal, salsalate, olsalazine, sulfasalazine, acetanilide, acetaminophen, phenacetin; mefenamic acid, sodium meclofenamate, tolmetin, ketorolac, diclofenac; ibuprofen, naproxen, sodium daproxen, fenoprofen, ketoprofen, flurbioprofen, oxaprozin, piroxicam, meloxicam, tenoxicam, ampiroxicam, droxicam, pivoxicam, phenylbutazone, oxyphenbutazone, anitpyrine, aminopyrine, dipyrone; celecoxib, rofecoxib; nabumetone; apazone; nimensulide; indomethacin; sulindac; and etodolac, whereby administration of said compound reduces gastric toxicity associated with said non-steroidal anti-inflammatory compound.

2. The method of claim 1, wherein said compound is derived from hops.

3. The method of claim 1, wherein the composition comprises about 0.5 to 10000 mg of said first compound.

4. The method of claim 3, wherein the composition comprises about 50 to 7500 mg of the first compound.

5. The method of claim 1, wherein the composition comprises about 0.001 to 10 weight percent of the first compound.

6. The method of claim 5, wherein the composition comprises about 0.1 to 1 weight percent of the first compound.

7. The method of claim 1, wherein the nonsteroidal anti-inflammatory compound is selected from the group consisting of salicylic acid, methyl salicylate, ibuprofen, naproxen, sodium daproxen, fenoprofen, ketoprofen, flurbioprofen, and oxaprozin.

8. The method of claim 1, wherein the composition further comprises a pharmaceutically acceptable carrier.

9. The method of claim 1, wherein the composition is administered orally, topically, parenterally, or rectally.

10. The method of claim 1, wherein the compound is administered concomitantly with said non-steroidal anti-inflammatory compound.

11. The method of claim 1, wherein said compound is administered after the administration of said non-steroidal anti-inflammatory compound.

12. The method of claim 1, wherein said compound is administered before the administration of said non-steroidal anti-inflammatory compound.

* * * * *